Figure 4A:
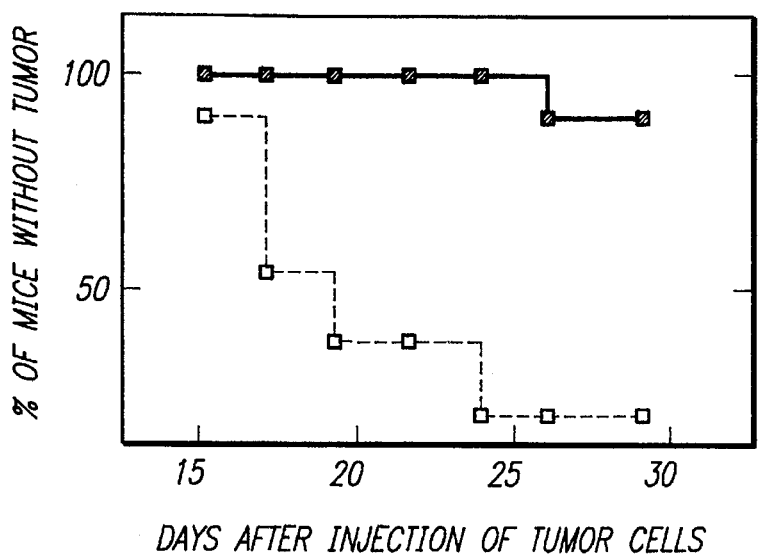

US005614610A

United States Patent [19]
Hellstrom et al.

[11] Patent Number: 5,614,610
[45] Date of Patent: Mar. 25, 1997

[54] TUMOR IMMUNOTHERAPY USING ANTI-IDIOTYPIC ANTIBODIES

[75] Inventors: Ingegerd Hellstrom; Karl E. Hellstrom; Maria S. Kahn; Donna F. Beaton, all of Seattle, Wash.

[73] Assignee: Oncogen, Seattle, Wash.

[21] Appl. No.: 225,446

[22] Filed: Jul. 28, 1988

Related U.S. Application Data

[63] Continuation-in-part of Ser. No. 116,802, Nov. 4, 1987, Pat. No. 4,918,164, Ser. No. 96,095, Sep. 10, 1987, abandoned, Ser. No. 901,856, Aug. 28, 1986, abandoned, Ser. No. 776,321, Oct. 18, 1985, Pat. No. 4,906,562, and Ser. No. 684,759, Dec. 21, 1984, Pat. No. 4,935,495.

[51] Int. Cl.$^6$ ........................................ C07K 16/42
[52] U.S. Cl. ............................ 530/387.2; 530/388.25
[58] Field of Search ..................... 530/387.2, 387.1, 530/388.25; 435/240.27

[56] References Cited

U.S. PATENT DOCUMENTS

| 4,699,880 | 10/1987 | Goldstein | 435/172.2 |
| 4,906,562 | 3/1990 | Hellstrom et al. | 435/7.2 |
| 4,918,164 | 4/1990 | Hellstrom et al. | 530/387.1 |

OTHER PUBLICATIONS

Jerne, N. K., 1974 "Towards a Network Theory of the Immune System," *Ann. Immunol. (Paris)* 125c:373–389.
Jerne et al., 1982, "Recurrent Idiotopes and Internal Images," *The EMBO Journal* 1(2):243–247.
Nepom et al., 1984, "Induction of immunity to a human tumor marker by in vivo administration of anti–idiotypic antibodies in mice," *Proc. Natl. Acad. Sci. U.S.A.* 81:2864–2867.
Forstrom et al., 1983, "Immunization to a Syngeneic Sarcoma by a Monoclonal Auto–Anti–Idiotypic Antibody," *Nature* 303:627–629.
Flood et al., 1980, "Suppression of Tumor Rejection by Autologous Anti–Idiotypic Immunity," *Proc. Natl. Acad. Sci. U.S.A.* 77:2209–2213.
Binz et al., 1982, "Induction or Elimination of Tumor–Specific Immunity Against a Chemically–Induced Rat Tumor Using Auto–Anti–Idiotypic Immunity," *Int. J. Cancer* 29:417–423.
Tilkin et al., 1981, "Reduced Tumor Growth After Low–Dose Irradiation or Immunization Against Blastic Suppressor T Cells," *Proc. Natl. Acad. Sci. U.S.A.* 78:1809–1812.

Kennedy et al., 1985, "Suppression of In Vivo Tumor Formation Induced By Simian Virus 40–Transformed Cells in Mice Receiving Antiidiotypic Antibodies," *J. Exp. Med.* 161:1432–1449.
Koprowski et al., 1984, "Human Anti–Idiotype Antibodies in Cancer Patients: Is the Modulation of the Immune Response Beneficial for the Patient?" *Proc. Natl. Acad. Sci. U.S.A.* 81:216–219.
Brown et al., 1981, "Structural Characterization of Human Melanoma–Associated Antigen p97 with Monoclonal Antibodies," *J. Immunol.* 127:539–546.
Hellstrom et al., 1986, "Monoclonal Mouse Antibodies Raised against Human Lung Carcinoma," *Cancer Res.* 46:3917–3923.
Hellstrom et al., 1986, "Antitumor Effects of L6, and IgG2a Antibody That Reacts with Most Human Carcinomas," *Proc. Natl. Acad. Sci. U.S.A.* 83:7059–7063.
Perosa and Ferrone, 1987, "Syngeneic Anti–Idiotypic Antisera to Murine Anti–HLA Class II Monoclonal Antibodies," *J. Immunol.* 139:1232–1239.
Tsujisaki et al., 1986, "A sandwich assay to detect and characterize syngeneic anti–idiotypic antibodies to murine anti–HLA and tumor associated antigen monoclonal antibodies," *J. of Immunological Methods* 95:47–55.

*Primary Examiner*—Lila Feisee
*Attorney, Agent, or Firm*—Pennie & Edmonds

[57] ABSTRACT

The present invention relates to methods which utilize anti-idiotypic antibodies, or fragments thereof, for tumor immunotherapy or immunoprophylaxis. Monoclonal anti-idiotypic antibodies which recognize an idiotype present on a second antibody or on a T lymphocyte or on an immune suppressor factor which is directed against a defined tumor antigen, can be used for immunization against a tumor, for immune anti-tumor activation or inhibition of suppression, or for in vitro activation of lymphocytes to be used in adoptive immunotherapy. The anti-idiotypic antibodies, or fragments thereof, can also be used to monitor anti-antibody induction in patients undergoing passive immunization to a tumor antigen by administration of anti-tumor antibody. In another embodiment, administration of T lymphocytes which express an idiotype directed against a defined tumor antigen can be used to transfer delayed-type hypersensitivity to the tumor. In another method of the invention, the induction of anti-idiotypic antibodies in vivo by administration of anti-tumor antibody or immune cells or factors exhibiting an anti-tumor idiotype can be therapeutically valuable.

5 Claims, 19 Drawing Sheets

FIG. 1
　　　　　　　　　　　　　Id⁺　　　　ANTI-id
1A
1B
1C
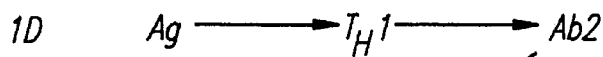
1D
FIG. 2
　　　　　　　　　　　　　Id⁺　　　　α-id
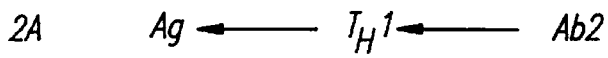
2A
2B
2C
FIG. 3
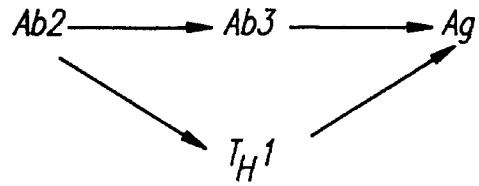

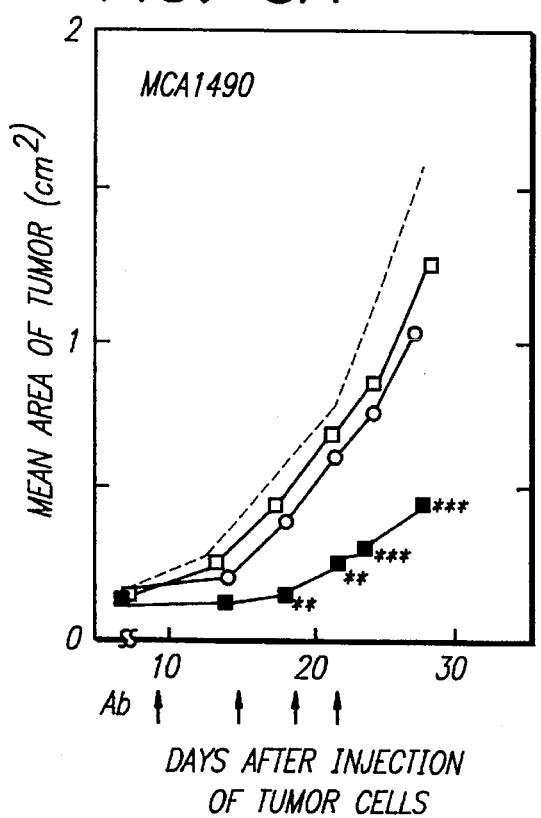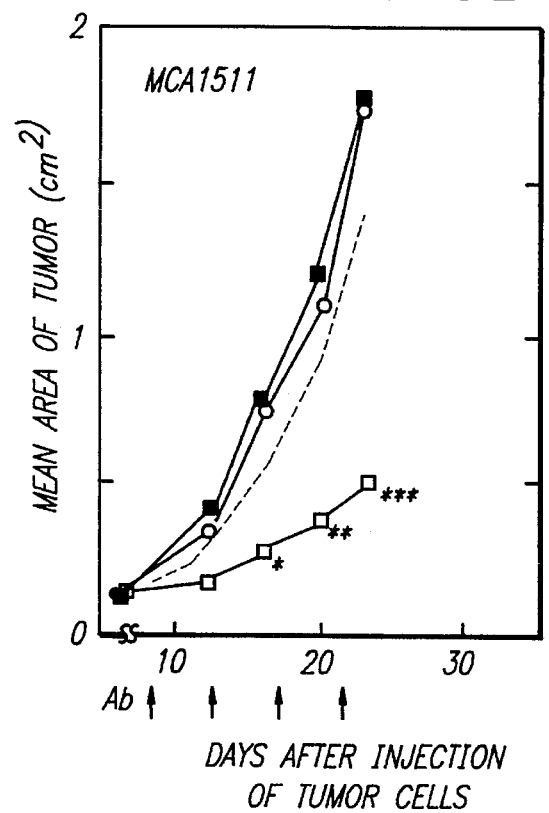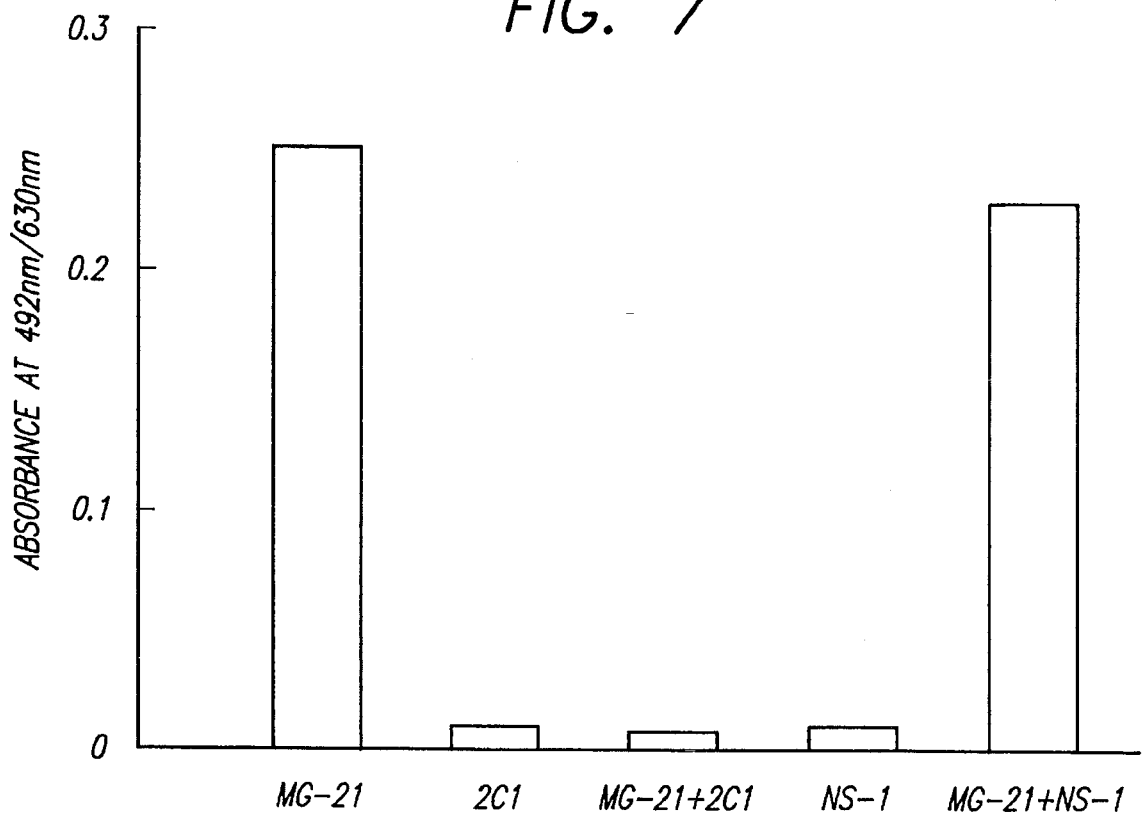

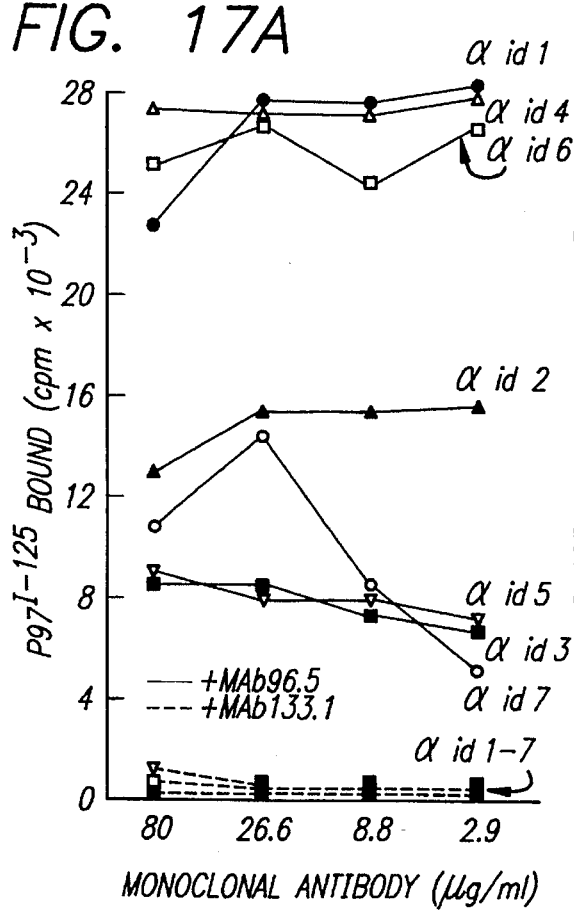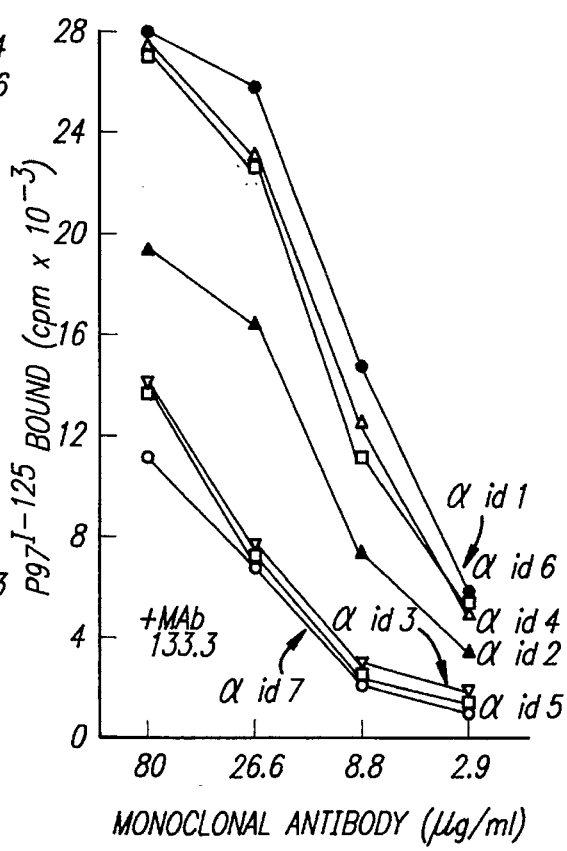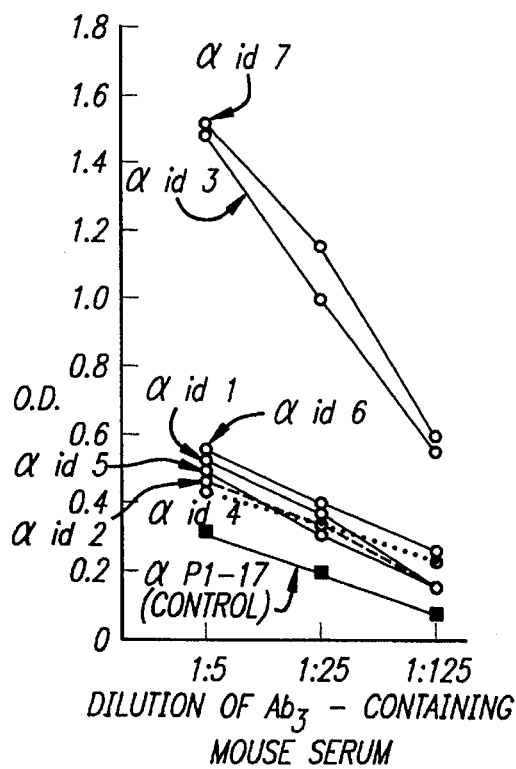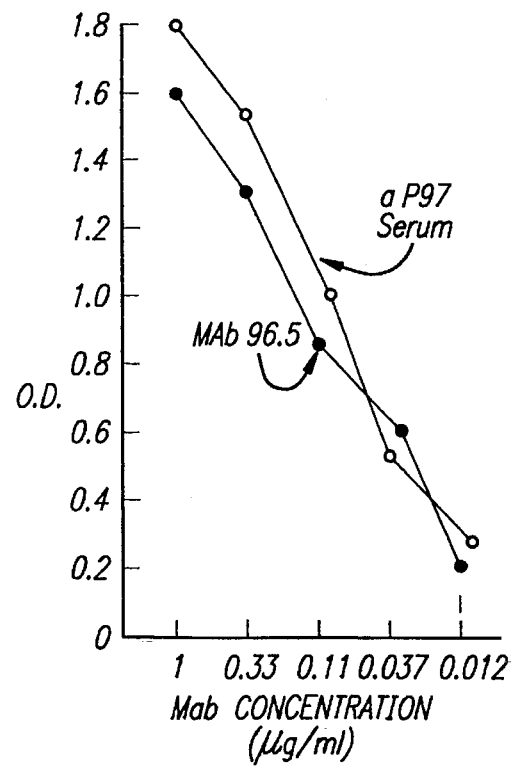

TUMOR IMMUNOTHERAPY USING ANTI-IDIOTYPIC ANTIBODIES

The present application is a continuation-in-part of applications U.S. application Ser. No. 116,802, filed Nov. 4, 1987, which issued as U.S. Pat. No. 4,918,164, on Apr. 17, 1990; U.S. application Ser. No. 096,095, filed Sep. 10, 1987; U.S. application Ser. No. 901,856, filed Aug. 28, 1986, now abandoned; U.S. application Ser. No. 776,321, filed Oct. 18, 1985, which issued as U.S. Pat. No. 4,906,562, on March 6, 1990; and U.S. application Ser. No. 684,759, filed Dec. 21, 1984, which issued as U.S. Pat. No. 4,935,495, on Jun. 19, 1990.

1. FIELD OF THE INVENTION

The present invention is directed to methods which utilize anti-idiotypic antibodies for tumor immunotherapy and immunoprophylaxis. The invention relates to the manipulation of the idiotypic network of the immune system for therapeutic advantage, e.g. by use of anti-idiotypic antibody for immunization against tumor, for inhibition of immune suppression mediated by suppressor T cells or suppressor factors expressing an idiotope directed against a tumor antigen, for activation of lymphocytes used in adoptive immunotherapy, etc. In a specific embodiment, monoclonal anti-idiotypic antibodies which were raised against the idiotype of an antibody that defines a self-differentiation antigen, such as an oncofetal, or differentiation antigen, can be used in vivo to induce an immune response against tumors bearing the oncofetal antigen.

The anti-idiotypic monoclonal antibodies of the present invention are valuable in tumor immunotherapy and immunoprophylaxis, and of general importance in human medicine. The molecules of the present invention may also be used as reagents in immunoassays such as ELISA tests and radioimmunoassays which are useful as diagnostic tools for the detection of antitumor antibodies or tumor antigens, and in immunoabsorption assays which are useful for the isolation and identification of anti-tumor antibodies. In addition, these reagents will be valuable tools in understanding the development and growth of neoplasia.

2. BACKGROUND OF THE INVENTION

2.1. Anti-Idiotypic Antibodies

Anti-idiotypic antibodies or anti-idiotypes are antibodies directed against the antigen-combining region or variable region (called the idiotype) of another antibody molecule. In theory, based on Jerne's network model of idiotypic relationships (Jerne, N. K., 1974, Ann. Immunol. (Paris) 125c:373; Jerne, N. K., et al., 1982, EMBO 1:234), immunization with an antibody molecule expressing a paratope (antigen-combining site) for a given antigen should produce a group of anti-antibodies, some of which share with the antigen a complementary structure to the paratope. Immunization with a subpopulation of the anti-idiotypic antibodies should in turn produce a subpopulation of antibodies or immune cell subsets that are reactive to the initial antigen.

A network of idiotopes and anti-idiotopes has been invoked to explain immune regulation, with common or related idiotopes of antibodies, B lymphocytes, and various subsets of T lymphocytes and their soluble products interacting with anti-idiotopes (Jerne, N. K., 1974, Supra; Urbain, J., et al., 1977, Proc. Natl. Acad. Sci. U.S.A. 74:5126; Rajewski, R. and Takemori, T., 1983, Ann. Rev. Immunol. 1:569). Studies which have been done on immunity to both haptens and vital antigens indicate that B cell derived anti-idiotypic antibodies can induce T cell responses (RaJewski, R. and Takemori, T., Supra; Urbain, J., et al., supra; Binz, H. and Wigzell, H., 1978, J. Exp. Med. 147:63). For example, Ertl et al. immunized mice with a Sendal virus-specific T cell clone and produced an anti-idiotypic mAb which regulated the DTH response to Sendai virus (Ertl, H. C. J., et al., 1982, Proc. Natl. Acad. Sci. U.S.A. 79:7479). As evidence for a B cell antibody arising in response to a T cell idiotype, Kennedy et al. observed tumor rejection, but no antitumor antibodies, in mice treated with anti-idiotopic antibodies relating to the SV40 T antigen (Kennedy, R. C., et al., 1985, J. Exp. Med. 161:1432). The administration of exogenous anti-idiotypic antibody can exert enhancing or suppressive influences, dependent on, among other variables, the dose of the antibody (Reth, M., et al., 1981, Nature (London) 290:257).

2.2. Tumor-Associated Antigens

A variety of tumor-associated antigens (TAA) have been described. One class of TAA is the tumor-specific transplantation type of cell-surface antigen (TSTA), which has been recognized by induction of immune responses in tumor transplant experiments.

Another class of TAA is the oncofetal or differentiation antigen. Oncofetal antigens are mainly embryonic or fetal cell products which are expressed by malignant cells due to derepression of the embryonic genes. One example of human oncofetal antigens are the carcinoembryonic antigens (CEA) of the colon. This set of antigens is found on tissues derived from the fetal gastrointestinal tract, and on tumors of the gastrointestinal tract. Alpha-fetoprotein is another known oncofetal antigen, which is secreted by hepatocarcinoma cells, as well as malignant yolk sac and fetal liver cells, and the proliferating fraction of adult liver cells.

A third class of TAA includes vitally-induced tumor antigens. These include the T antigen induced by DNA tumor viruses, and the envelope antigens of RNA tumor viruses.

A variety of human cell-surface TAA has been detected in human neoplasms by mouse monoclonal antibodies (Hellstrom, K. E., et al., 1982, Human Tumor-Associated Antigens Identified by Monoclonal Antibodies, in, Springer Seminars in Immunopathology: Mechanism of Host Resistance in Cancer. Springer, New York, pp. 127–146; Herlyn, M., et al., 1984, in, Contributions to Oncology, Karger, Basel, Switzerland, Vol. 19 pp. 160–170; Reisfeld, R. A. and Sell, S., eds., 1985, Monoclonal Antibodies and Cancer Therapy, UCLA Symposia on Molecular and Cellular Biology, New Series, Vol. 27, Alan R. Liss, Inc., New York). Many of these antigens are termed oncofetal, since they are expressed strongly by tumors and certain embryonic cells and much more weakly by normal cells from the adult host. Other tumor-associated antigens have been detected by their ability to stimulate host cell-mediated immunity (CMI) in human cancer (Hellstrom, K. E., and Hellstrom, I., 1969, Adv. Cancer Res. 12:167–223; Halliday, W. J., and Maluish, A. E., 1982 in, Assessment of Immune Status by the Leukocyte Adherence Inhibition Test, Academic, New York pp. 1–26; Herherman, R. B., 1974, Adv. Cancer Res. 19: 207–263; Thomson, D. M. P., 1980, Cancer Res. 29 627–629; Halliday, W. J., et al. 1975, Int. J. Cancer 16:645–654) and in tumor-bearing animals (Taranger, L. A., et al., 1972, Science 176 1337–1340; Halliday, W. J., et al., 1974, Cell Immunol. 10:1467–475; Steele, G., et al., 1975, J. Natl. Cancer Inst. 54:959–967). Some of these antigens are also oncofetal, but their molecular nature and relationship to the antigens defined by mouse monoclonal antibodies are unclear.

Rat monoclonal antibodies to antigens shared by mouse bladder carcinomas have been obtained recently (Hellstrom, I., et al., 1982, Int. J. Cancer 29:175–180; Hellstrom, I., et al., 1985, Cancer Res. 451 2210–2218). One of the antibodies, 6.10, was shown to be specific for a bladder tumor oncofetal antigen (Hellstrom, I., et al., 1985, Cancer Res. 45:2210–2188).

Unmodified tumor antigen (Hoover, H. C., et al., 1985, Cancer 55:1236–1243; McIllmurray, M. B., et al., 1978, Br. Med. J. 1:579–580) and live recombinant viruses (Earl, P. L., et al., 1986, Science 23:728–731; Lathe, R., et al., 1987, Nature 236:878–880) have been used in attempts to induce therapeutically beneficial anti-tumor immune responses.

2.3. Idiotypic Manipulation of Tumor Immunity

Several idiotypic manipulations of tumor immunity have been reported, Nepom et al. (1984, Proc. Natl. Acad. Sci. U.S.A. 81:2864–2867) described induction of tumor immunity where an oncofetal antigen was introduced into a xenogeneic host. Polyclonal anti-idiotypic antibodies were prepared which recognized idiotypic determinants on a mouse antibody to the $p97^c$ epitope of human melanoma antigen p97. The polyclonal antisera could induce, in mice, both CMI and an Ab3 response to p97. Forstrom et al. (1983, Nature (London) 303:627–629) used an anti-idiotypic antibody to induce CMI in mice to a syngeneic chemically induced sarcoma. In this study, the anti-idiotypic antibody was an auto-antibody produced by hyperimmunization to the tumor, and the tumor antigen was not a defined molecule. The studies of Flood et al. (1980, Proc. Natl. Acad. Sci. U.S.A. 77:2209–2213) and Binz et al. (1982, Int. J. Cancer 29:417–423) demonstrated idiotypic manipulations of tumor immunity in syngeneic systems, with undefined antigen molecules. Flood et al. showed evidence that murine anti-idiotypic T lymphocytes could participate in an autoimmune reaction to fibrosarcoma-specific T lymphocytes, and thus adversely affect an individual's immune response to a tumor. Binz et al. used anti-idiotypic antibodies to induce in vitro proliferation of T lymphocytes specifically cytotoxic to rat sarcoma cells.

Additional studies have looked at the effect of anti-idiotypic antibodies on tumor growth. Tilkin et al. (1981, Proc. Natl. Acad. Sci., U.S.A. 78:1809–1812) showed that immunization of mice with lymph node cells sensitized to an unidentified sarcoma antigen resulted in tumor rejection and growth inhibition. Kennedy et al. (1985, J. Exp. Med. 161:1432–1449) described the suppression of tumor formation in mice challenged with SV40-transformed cells, after injection with polyclonal anti-idiotypic antibodies related to the SV40 antigen.

Koprowski et al. (1984, Proc. Natl. Acad. Sci. U.S.A. 81:216–219) showed the presence of anti-idiotypic antibodies in patients who had a remission of carcinoma after administration of a monoclonal antibody directed against human gastrointestinal cancer.

2.4. Suppressor Cells and Suppressor Factors

The suppressor cell/factor cascade has been recognized in tumor and model systems (Nepom, G. T., et al, 1983, Experientia 39:235; Asherson, G. L., et al., 1984, Immunology 53:491; Doff, M. E. and Benacerraf, B., 1984, Alan. Rev. Immunol. 2:127). Suppressor cells play an important role in regulating tumor immunity (Greene, M. I., et al., 1977, Proc. Natl. Acad. Sci. U.S.A. 74:5118; Hellstrom, K. E., et al., 1978, J. Exp. Med. 148:799; Nepom, G. T., et al., 1983 Experientia 39:235; North, R. J., 1982, J. Exp. Med. 155:1063, Yamauchi, K., et al., 1979, J. Immunol. 123:1653). Some of these cells produce suppressor factors (SF) (Nelson, K., et al., 1975, Int. J. Cancer 16:539; Greene, M. I., et al., 1977, J. Immunol. 119:759; Koppi, T. A. and Halliday, W. J., 1983, Cell. Immunol. 76:29) which can be detected in sera from tumor-bearing animals and human patients through the inhibition ("blocking") of in vitro manifestations of cell-mediated immunity (CMI) (Hellstrom, K. E., et al., 1978, J. Exp. Med. 148:799; Hellstrom, I., et al., 1969, Proc. Natl. Acad. Sci. U.S.A. 62:362; Baldwin, R. W., 1973, Adv. Cancer Res. 18:15 Halliday, W. J., et al., 1974, Cell. Immunol. 10:467; Steele, G., et al., 1975, J. Natl. Cancer Inst. 54:959; Hellstrom, K. E., et al., 1977, Blochim. Biophys. Acta 473:121; Halliday, W. J., et al., 1980, J. Natl. Cancer Inst. 65:327; Koppi, T. A. and Halliday, W. J., 1981, J. Natl. Cancer Inst. 66:1089; Kuchroo, V. K., et al., 1983, Cancer Res. 43:1325; Koppi, T. A., et al., 1981, J. Natl. Cancer Inst. 66:1097). Some SF have tumor specificity and can be removed from serum by absorption with the respective tumor or tumor-related antigen but not with tumors expressing different antigens (Kuchroo, V. K., et al., 1983, Cancer Res. 43:1325; Baldwin, R. W., 1973, Adv. Cancer Res. 18:1; Hellstrom, K. E., et al., 1977, Biochim. Biophys. Acta 473:121; Koppi-Reynolds, T. A. and Halliday, W. J., 1984, Immunol. Lett. 8:219). This suggests that there is a binding site or idiotope on SF molecules, complementary to the tumor antigen determinants (Nepom, G. T., et al., 1983, Experientia 39:235; Hellstrom, K. E., et al., 1977, Blochim. Biophys. Acta 473:121). It has been reported that circulating SF bind to antibodies from mice hyperimmunized with tumor cells, suggesting that the antibodies are complementary to idiotypic determinants on the SF (Hellstrom, K. E., et al., 1977, Biochim. Biophys. Acta 473:121; Nepom, G. T., et al., 1977, Proc. Natl. Acad. Sol. U.S.A. 74:4605); in these studies, both the antibody and suppressor cell responses were assumed to be polyclonal. Certain immune sera, obtained after tumor removal or regression, abrogate ("unblock") the antigen-specific suppressive ("blocking") activity of tumor-bearer sera as measured in vitro (Halliday, W. J., et al., 1974, Cell. Immunol. 10467; Hellstrom, I. and Hellstrom, K. E., 1970, Int. J. Cancer 5:195). It has been theorized that this "unblocking" effect was mediated by anti-idiotypic antibodies (Hellstrom, K. E., et al., 1977, Blochim. Biophys. Acta 473:121). It was reported that "unblocking" antibodies had a therapeutic effect in rats with primary or transplanted polyoma virus-induced tumors (Bansal, S. C. and Sjogren, H. O., 1972, Int. J. Cancer 9:490; Sjogren, H. O. and Bansal, S. C., 1971, in Progress in Immunology, Amos, B., ed., Academic Press, New York, p. 921; Eansal, S. C. and Sjogren, H. O., 1971, Nature (New Biol.) 233:76).

3. SUMMARY OF THE INVENTION

The present invention is directed to methods which utilize anti-idiotypic antibodies, or fragments thereof, for tumor immunotherapy and immunoprophylaxis. The invention relates to the manipulation of the idiotypic network of the immune system for therapeutic advantage. Particular embodiments include the use of anti-idiotypic antibodies for immunization against tumor, for activation of lymphocytes to be used in adoptive immunotherapy, and for inhibition of immune suppression mediated by suppressor T cells or suppressor factors expressing an idiotope directed against a tumor antigen. In specific embodiments, monoclonal anti-idiotypic antibodies, or fragments thereof, (a) which were raised against the idiotype of an antibody that defines a tumor antigen, such as an oncofetal or differentiation antigen, and (b) which exhibit tumor-specific properties such as induction of tumor-specific cell mediated immunity (as measured by various assays, e.g. the leukocyte adherence inhibition assay or the delayed-type hypersensitivity assay), inhibition of anti-tumor antibody binding, etc. are identified. The monoclonal anti-idiotypic antibodies, or fragments thereof, which demonstrate immunopotency can be used in vivo in a patient to induce an immune response directed against tumor cells that bear the tumor antigen. The anti-idiotypic antibodies, or fragments thereof, can also be used to monitor anti-antibody induction in patients undergoing passive immunization to a tumor antigen by administration of anti-tumor antibody.

In another embodiment, the induction of anti-idiotypic antibodies in vivo by administration of anti-tumor antibody or immune cells or factors exhibiting the anti-tumor idiotopes, can be of therapeutic value.

The invention is also directed to the monoclonal anti-idiotypic antibody molecules, antibody fragments, or chemically modified antibodies or fragments, which recognize an idiotype directed against a defined tumor antigen. The molecules of the invention may be produced by any technique known in the art, including the hybridoma technique originally described by Kohler and Milstein (1975, Nature 256:495–497), the human B-cell hybridoma technique (Kozbor et al., 1983, Immunology Today 472), and the EBV-transformation technique (Cole et al., 1985 Monoclonal Antibodies and Cancer Therapy, Alan R. Liss, Inc., pp. 77–96).

The invention is illustrated by way of example in which serotherapy of mice by injection with anti-idiotypic antibodies related to a murine fibrosarcoma delayed the appearance and caused regression of transplanted sarcoma. A T cell line was established which expressed an idiotope directed against a fibrosarcoma, and which could transfer delayed-type hypersensitivity to the fibrosarcoma.

In another example of the invention, a mouse monoclonal anti-idiotypic antibody which is specific to an idiotype which recognizes a human melanoma-associated GD3 ganglioside antigen is described. The anti-idiotypic antibody was demonstrated to prevent binding of the anti-GD3 antibody to its antigen, and to inhibit both complement- and antibody-dependent cytotoxicity of the anti-GD3 antibody. By using the anti-idiotypic antibody as a probe, an assay was developed to monitor human antibodies to the anti-GD3 antibody in patients receiving the anti-GD3 antibody for therapeutic or diagnostic purposes.

In a third example of the invention, mouse monoclonal anti-idiotypic antibodies which recognize an idiotype directed against a human melanoma-associated p97 antigen are described. Monoclonal anti-idiotypic antibodies were obtained which could competitively inhibit the binding of p97 to anti-p97 antibody, and which could induce antibodies to p97 in vivo.

In another example, we describe murine monoclonal anti-idiotypic antibodies which recognize an idiotype on monoclonal antibody L6 which defines a carbohydrate antigen of human carcinomas. Anti-idiotypio antibodies were obtained which were capable of inducing antibodies in vivo reactive with the carcinoma antigen defined by antibody L6.

The antibody molecules of the invention, fragments of the antibody molecules containing the idiotype of the molecules, or chemical modifications of these molecules can be used to assay for the presence of anti-tumor antibodies, tumor antigen by competition assays, and the induction of cell-mediated tumor immunity in immunoprophylactic and immunotherapeutic applications.

3.1. Definitions

As used herein, the following abbreviations will have the meanings indicated:

Ab1=antibody 1; the initial antibody of an anti-idiotypic antibody cascade

Ab2=antibody 2; anti-idiotypic antibody directed against an idiotype of Ab1

Ab3=antibody 3; anti-anti-idiotypic antibody, directed against an idiotype of Ab2

ADCC=antibody-dependent cellular cytotoxicity anti-Id=anti-idiotypic antibody(ies)

BTCC=bladder transitional cell carcinoma

CDC=complement-dependent cytotoxicity

CMI=cell-mediated immunity

DTH=delayed-type hypersensitivity

FACS=fluorescence-activated cell sorter

FCS=fetal calf serum

FITC=fluorescein isothiocyanate

HRP=horseradish peroxidase

Id=idiotope

Ig=immunoglobulin i.p.=intraperitoneal i.v.=intravenous kDa=kiloDalton

KLH=keyhole limpet hemocyanin

LAI=leukocyte adherence inhibition mAb=monoclonal antibody(ies)

MCA=3-methylcholanthrene

OPD=O-phenylene diamine par=parental (p97-negative) C3H/HeN mouse melanoma line K-1735-M2

PBS=phosphate buffered saline

PC=peritoneal cells

SC=spleen cell

4. DESCRIPTION OF THE FIGURES

FIG. 1. A schematic diagram of four types of idiotypic and anti-idiotypic responses initiated by antigenic stimuli. $T_H$ (FIG. 1B, 1D) or $T_S$ (FIG. 1C) substituting for Ab1 in the stimulation of anti-idiotypic antibody production is illustrated.

FIG. 2. A schematic diagram of three pathways by which Ab2 can induce antitumor immunity. FIG. 2A shows the induction of antigen specific $T_H$ upon immunization with Ab2. The elicitation of normally "silent" Ab1 specificities is illustrated (FIG. 2B), as is the triggering of Id$^+$ $T_S$ (FIG. 2C).

FIG. 3. A schematic diagram of immunization with internal-image anti-idiotypic antibody to elicit anti-antigen response.

Figure 4B:
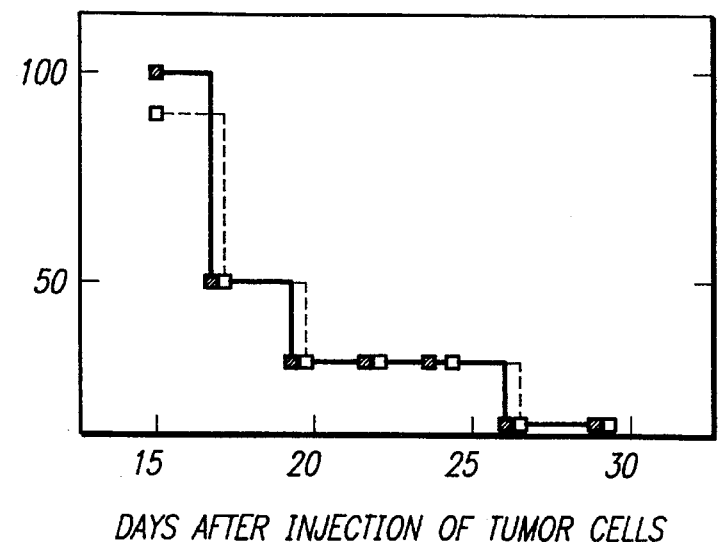
Figure 4C:
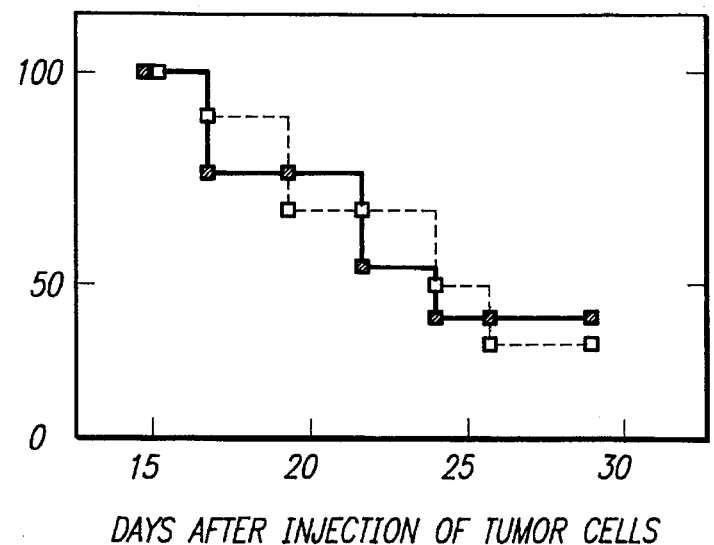

FIG. 4. T cells of line 90.3 (closed circles) inhibit the growth of MCA-1490 (Panel A) but not MCA-1510 or MCA-1511 (Panels B and C). The growth of tumor mixed with control T cells (open circles) was used for comparison.

FIG. 5. Treatment of tumor-bearing mice with auto-anti-idiotypic mAb inhibits tumor growth. mAb were given intraperitoneally, on days 8, 13, 17, and 21. Tumor size is presented as the average area of the tumors for the 10 mice in each treatment group. Mice were treated with mAb 4.72 (closed circles), mAb 5.96 (open squares), mAb 8.2 (open circles) or PBS (dashed line). Difference significant at *p less than 0.05,p less than 0.01, *p less than 0.001.

Figure 6A:
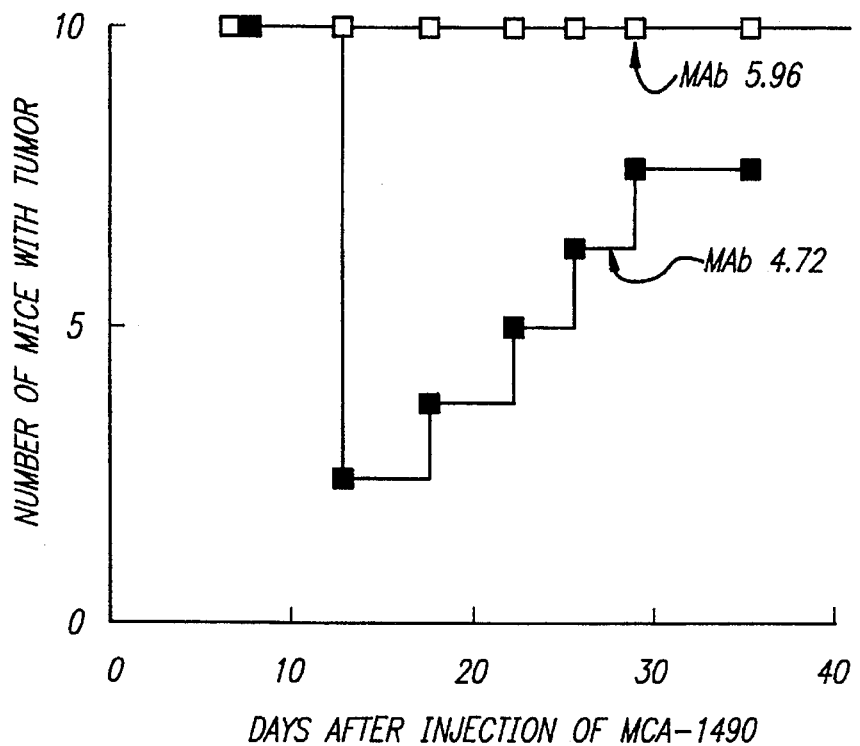
Figure 6B:
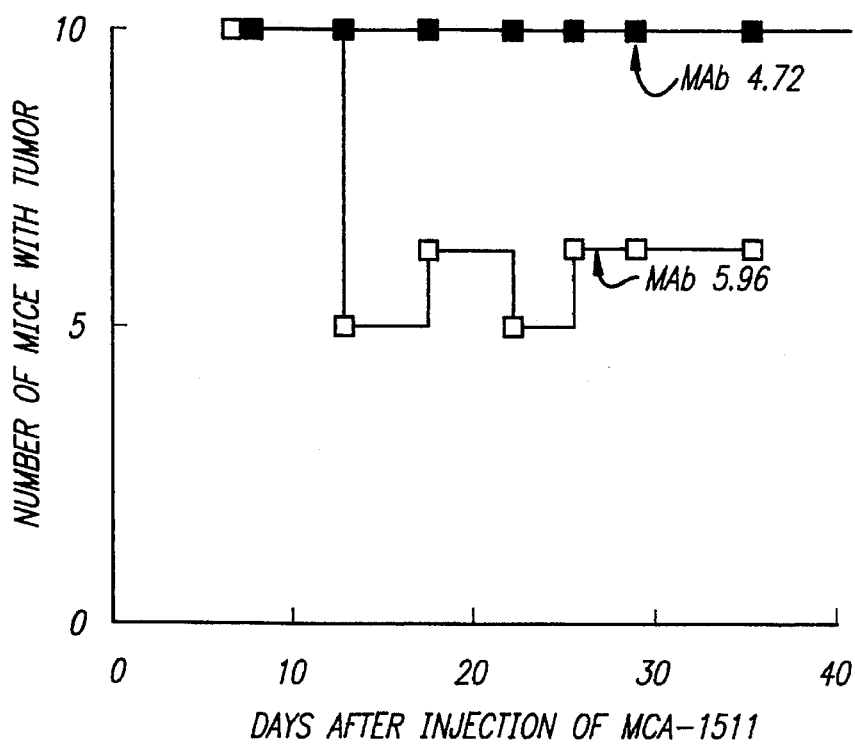

FIG. 6. Treatment of tumor-bearing mice with auto-anti-idiotopic monoclonal antibodies induces regression of growing satcomas. The number of mice with tumors greater than 0.2 $cm^2$ after treatment with mAb 4.72 (closed circles) or mAb 5.96 (open circles) is presented for tumor MCA-1490 (top panel) or MCA-1511 (bottom panel).

FIG. 7. Inhibition of mAb MG-21 binding to M-2669 clone 13 cells by culture supernatant of anti-idiotypic antibody-producing hybridoma 2C1.

Figure 8:
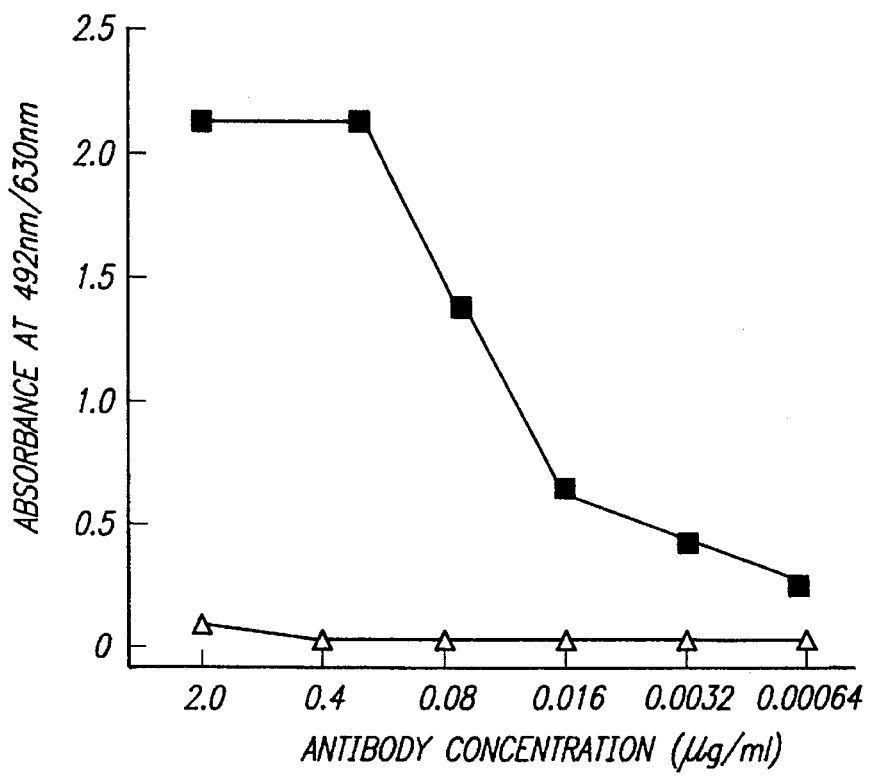

FIG. 8. Direct binding of monoclonal anti-idiotypic antibody 2C1 to mAbMG-21. Various concentrations of mAb 2C1 (closed circles) or control immunoglobulin P1.17 (closed triangles) were added to polyvinyl chloride wells precoated with mAb MG-21.

Figure 9:
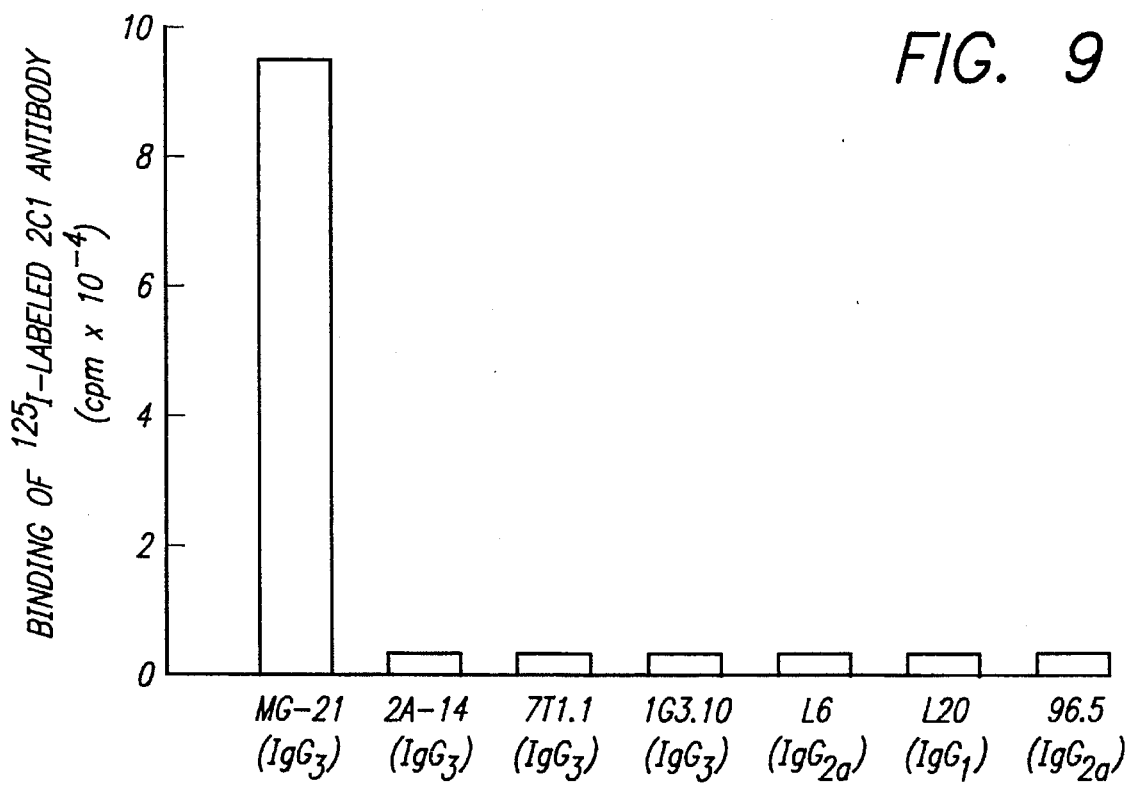

FIG. 9. Specificity of anti-idiotypic mAb 2C1 for MG-21 as compared to various mAbs.

Figure 10:
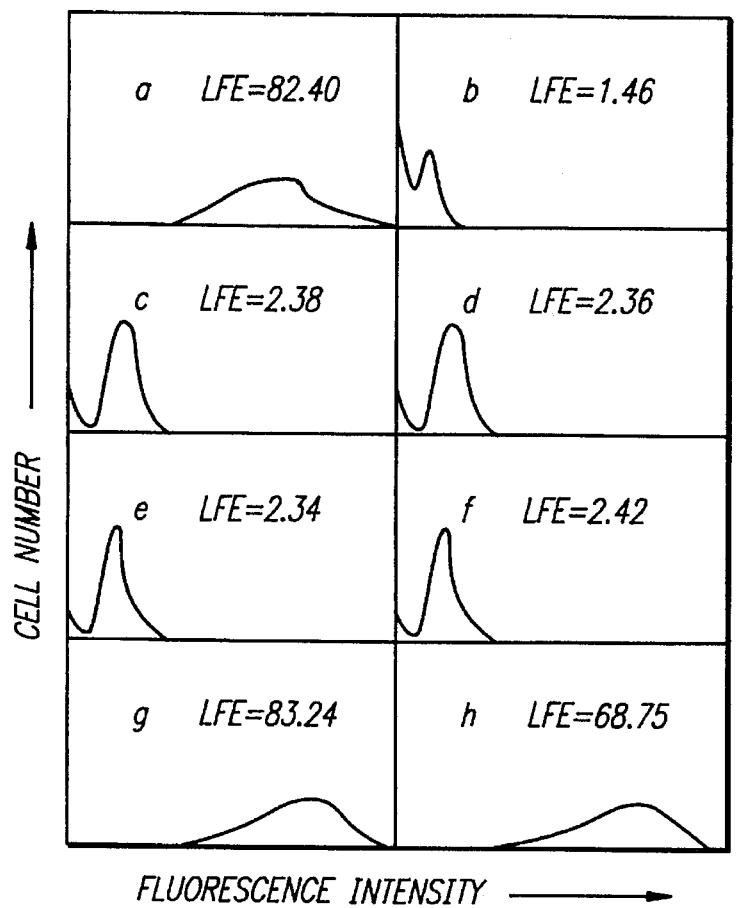

FIG. 10. Cell-sorting profiles of FITC-conjugated MG-21 against M-2669 cells in the presence or absence of mAb 2C1. Tumor cells were stained with FITC-conjugated MG-21 alone (40 ug/ml, panel a) or remained unstained to obtain the background level (panel b). Panels c through f show inhibition of staining with FITC-conjugated MG-21 in the presence of mAb 2C1 at different concentrations (panel c, 160 ug/ml; panel d, 80 ug/ml; panel e, 40 ug/ml; panel f, 20 ug/ml). Panels g and h show staining of FITC-conjugated MG-21 in the presence of mAb 26.8 (160 ug/ml) and P1.17 (160 ug/ml).

Figure 11:
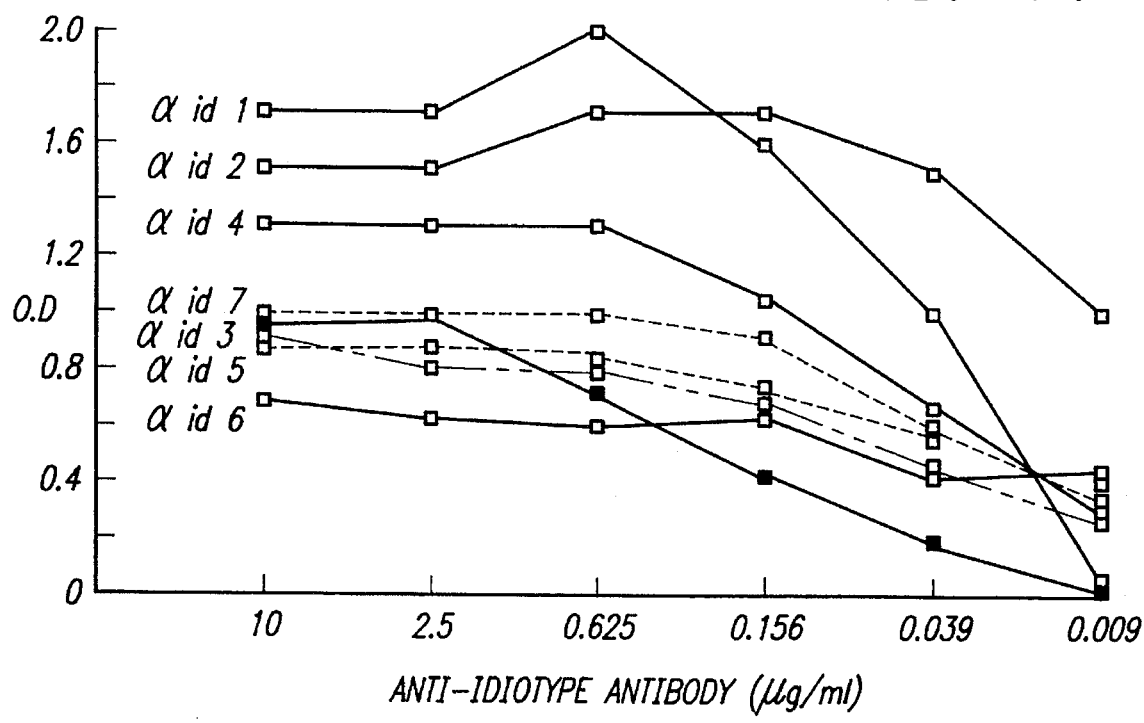

FIG. 11. Binding of purified anti-idiotypic antibody (Ab2) to Fab fragments of anti-p97 mAb 96.5. Fab antibody fragments of mAb 96.5 were plated and blocked, various dilutions of Ab2 added, and the binding of Ab2 detected by addition of HRP-labelled goat anti-mouse IgG, as described in Section 8.1.5.

Figure 12:
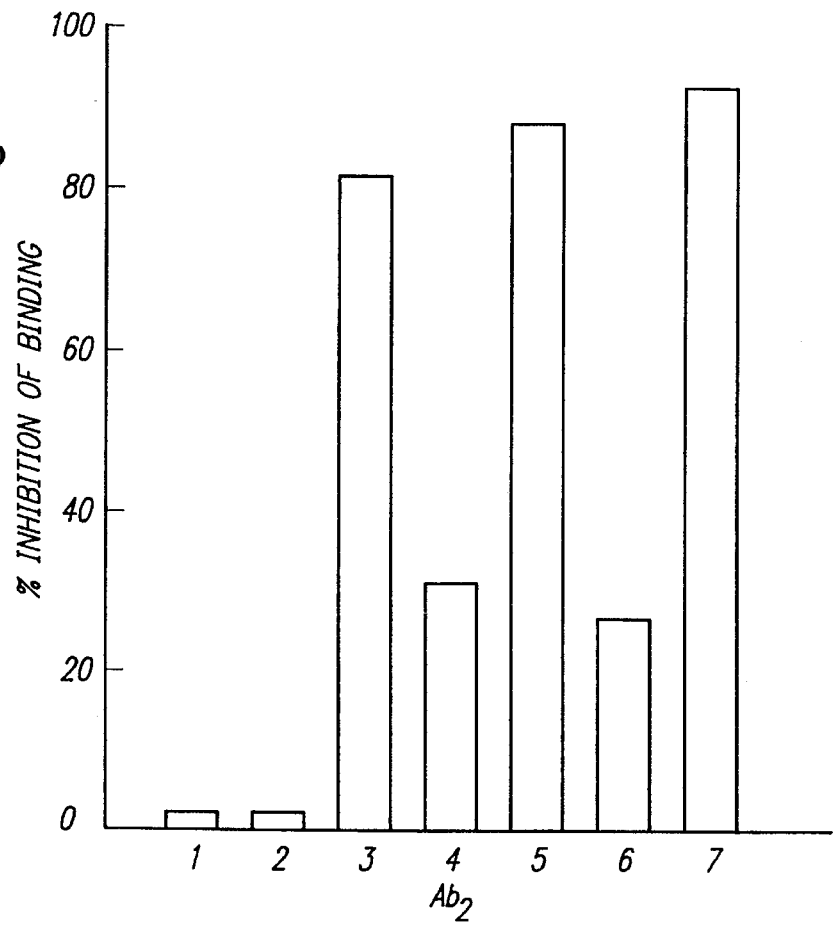

FIG. 12. Ab2 can inhibit the binding of mAb 96.5 to SK MEL-28 cells. Anti-p97 mAb 96.5 (0.33 ug/ml) was mixed with purified anti-idiotypic antibody (Ab2) (10 ug/ml) and added to SK MEL-28 cells, which express approximately 400,000 molecules of p97 per cell and which had been plated onto the wells of Immunolon plates. The binding of mAb 96.5 to the cells was detected by an ELISA and the inhibition of this binding by Ab2 was calculated.

Figure 13:
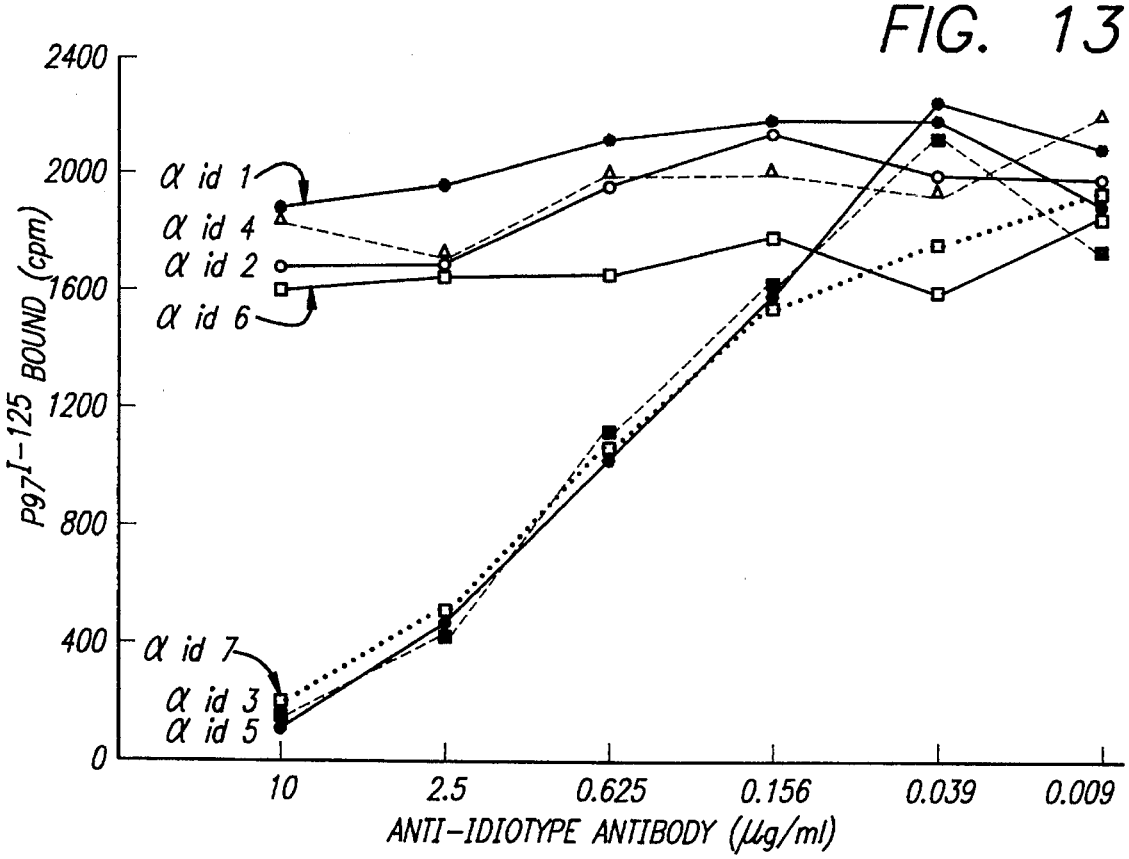

FIG. 13. Competitive inhibition by anti-idiotypic antibody (Ab2) of the binding of $^{125}$I-labelled p97 antigen to Fab fragments of anti-p97 mAb 96.5. Various dilutions of each Ab2 were mixed with radioiodinated p97, and the binding of p97 to Fab fragments of mAb 96.5 was determined in a solid phase assay.

Figure 14:
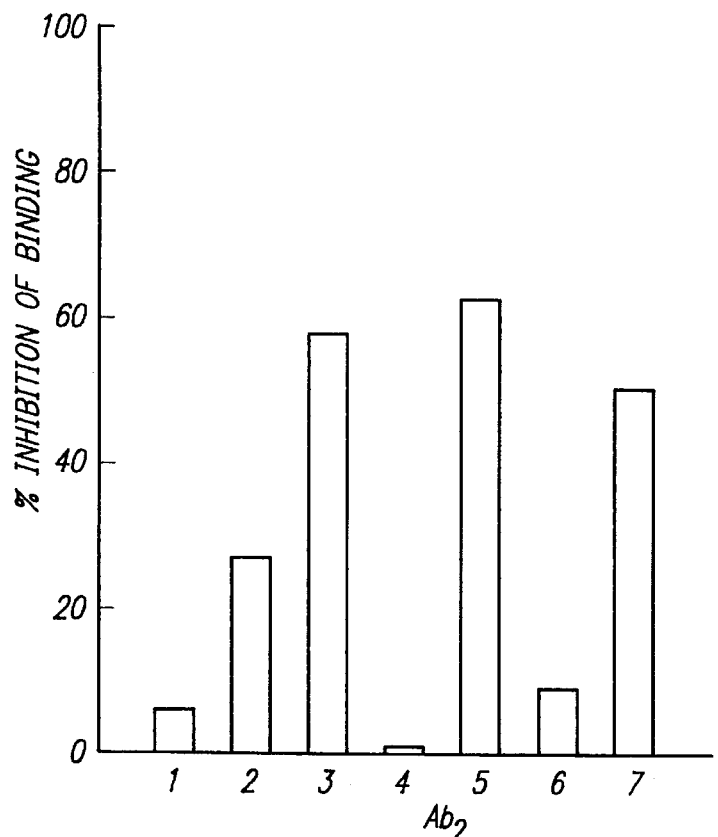

FIG. 14. Anti-idiotypic antibody (Ab2) can inhibit the binding of Fab fragments of anti-p97 mAb 96.5 to radiolabelled p97. Fab fragments of mAb 96.5 were plated onto the wells of Immunolon plates, and Ab2 (10 ug/ml) was added. The Ab2 were tested for their ability to decrease the binding of radiolabelled p97 to the Fab-coated wells, by blocking of the p97-binding sites on the Fab fragments.

FIG. 15. Assays of the ability of mAb which recognize different epitopes of the p97 antigen to inhibit the binding of Ab2 to Fab fragments of anti-p97 mAb 96.5. Each anti-p97 mAb was mixed with the Ab2 to be tested, and added to plates coated with Fab fragments of mAb 96.5, followed by addition of goat anti-mouse IgG1-HRP to detect the binding of the respective Ab2 to the Fab fragments. The binding of a given Ab2 was tested alone (closed circles), or in the presence of P1.17 control immunoglobulin (X—X), and compared with the binding seen after various mAb specific for p97 had been added (open circles).

Figure 16:
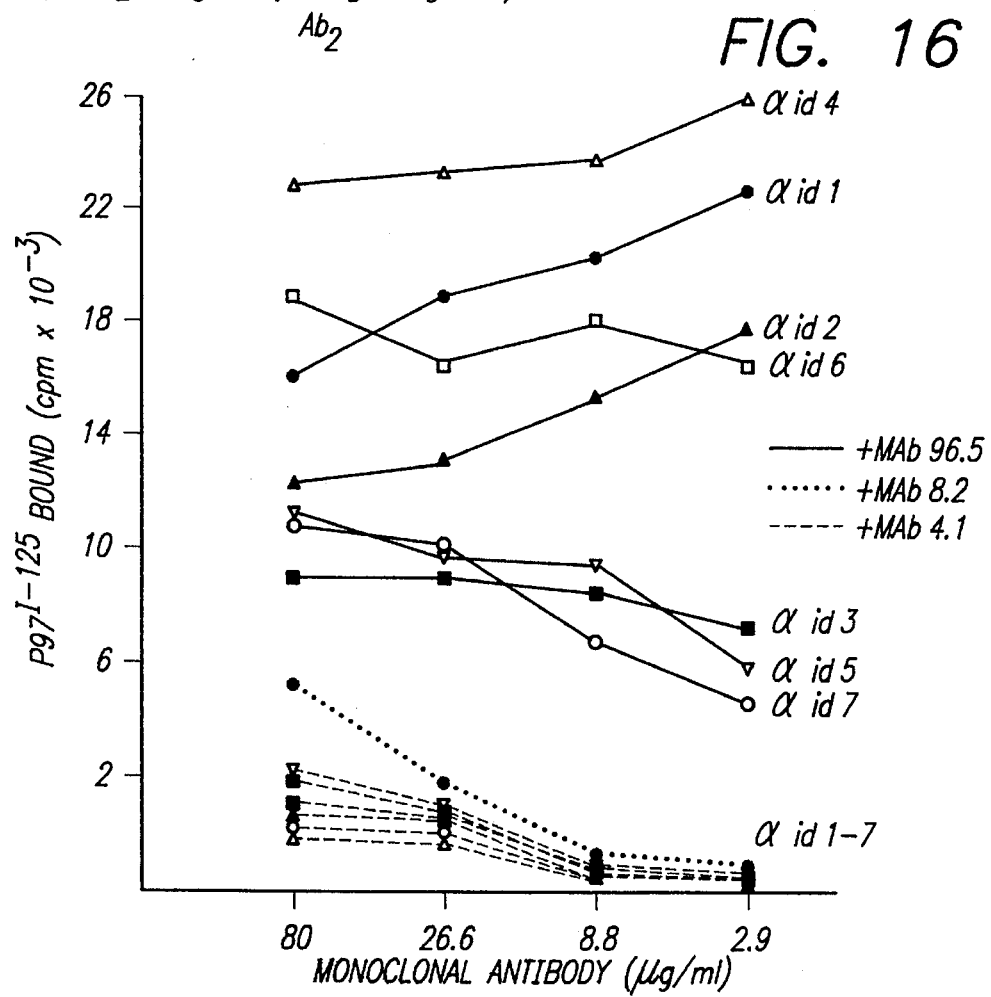
Figure 15A:
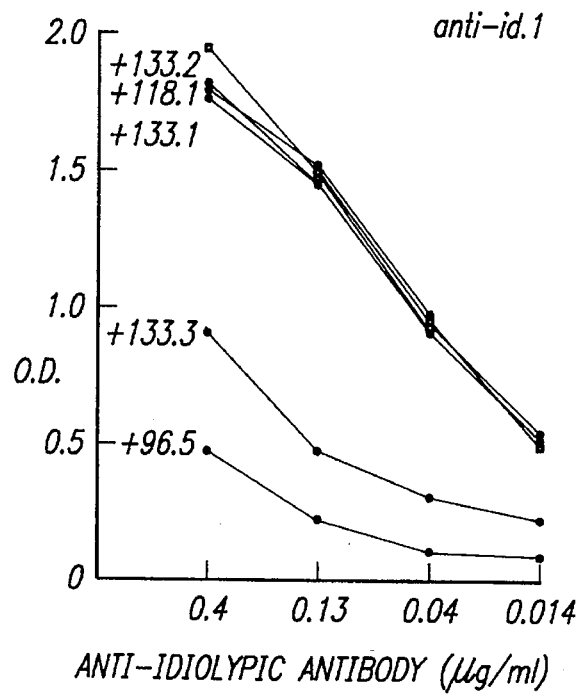
Figure 15B:
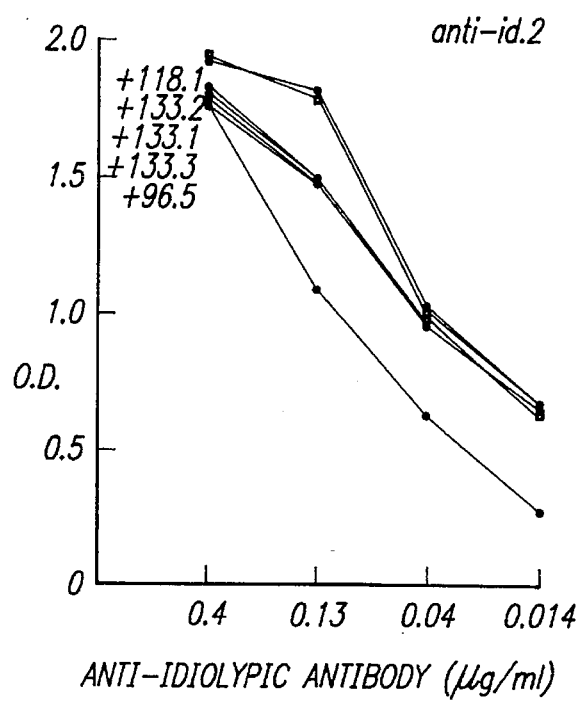
Figure 15C:
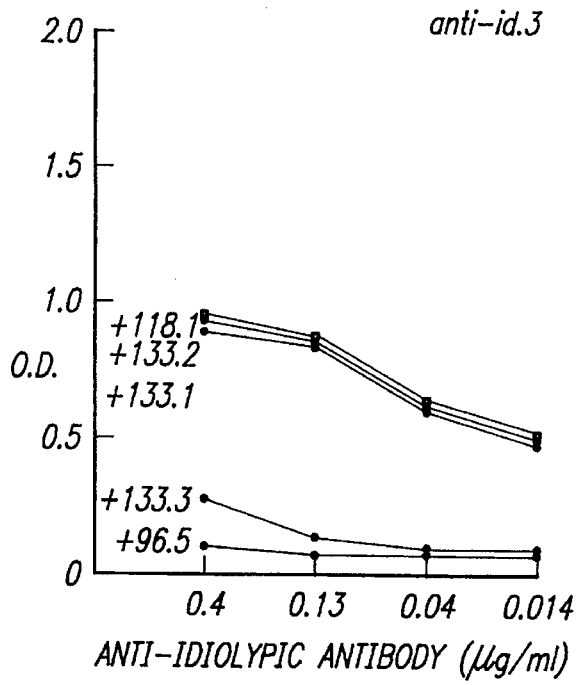
Figure 15D:
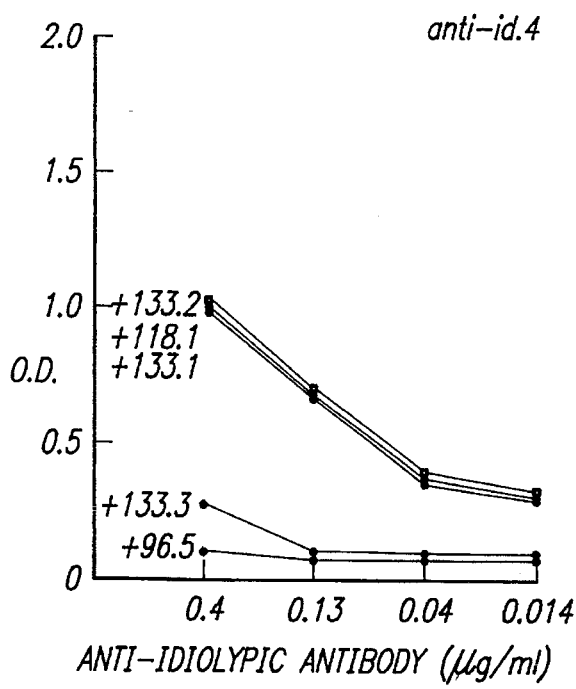
Figure 15E:
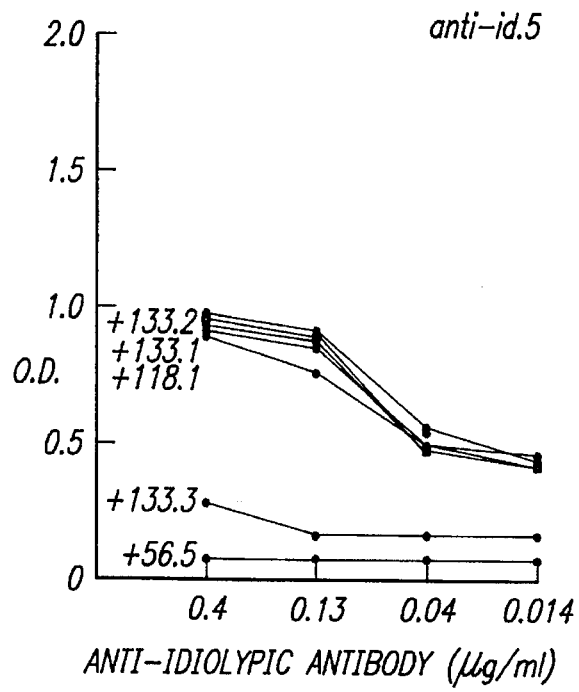
Figure 15F:
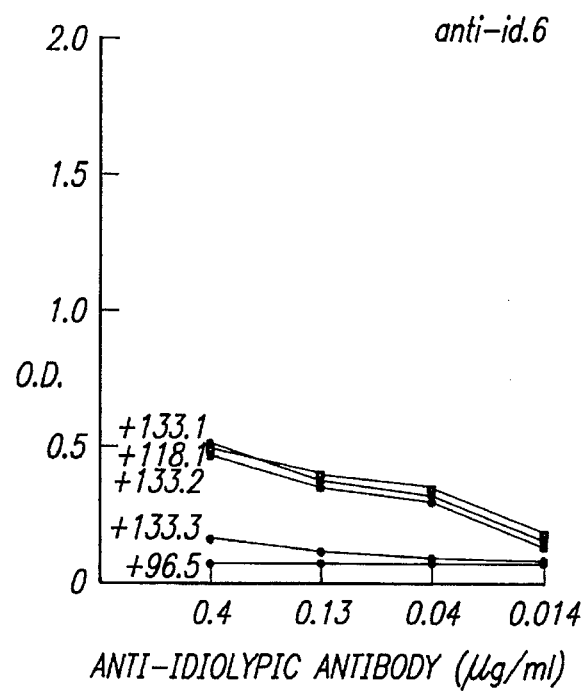
Figure 15G:
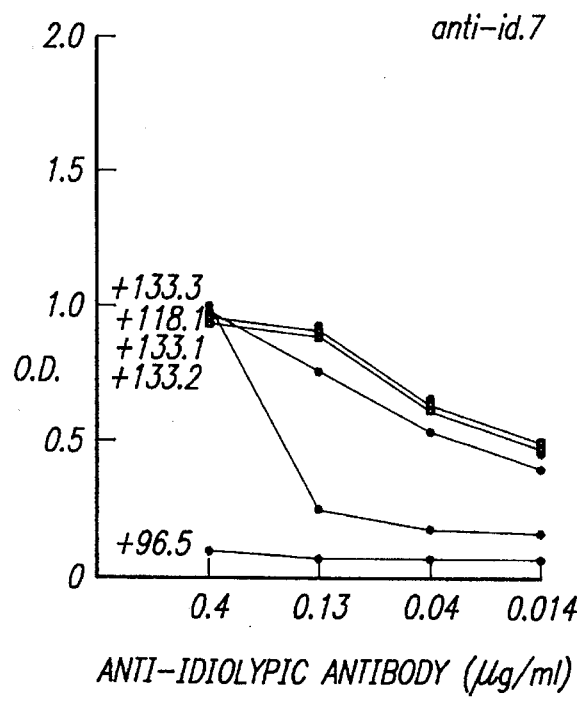
Figure 19A:
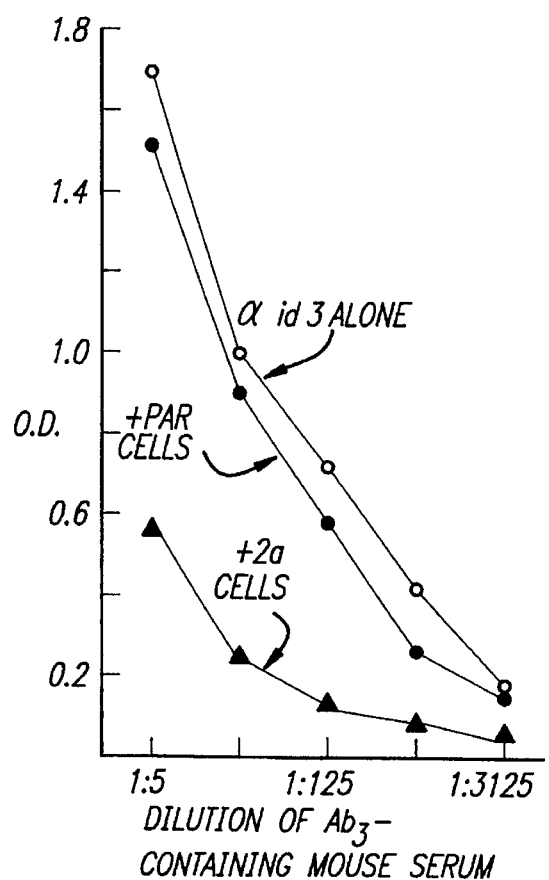
Figure 19B:
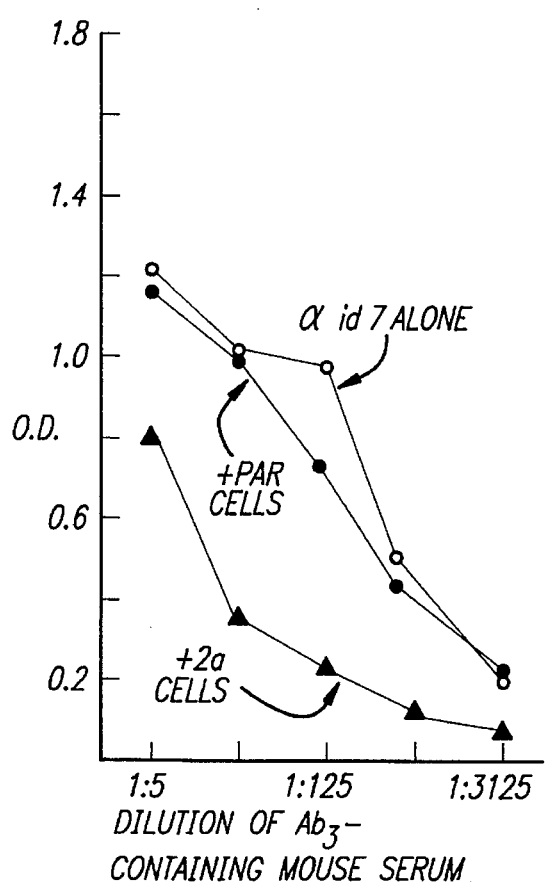
Figure 19C:
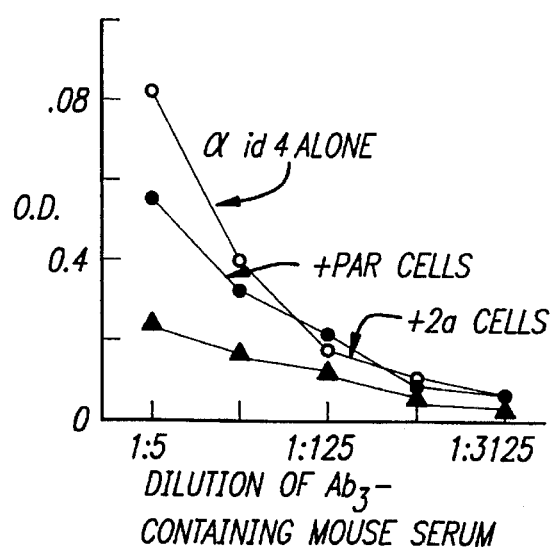
Figure 19D:
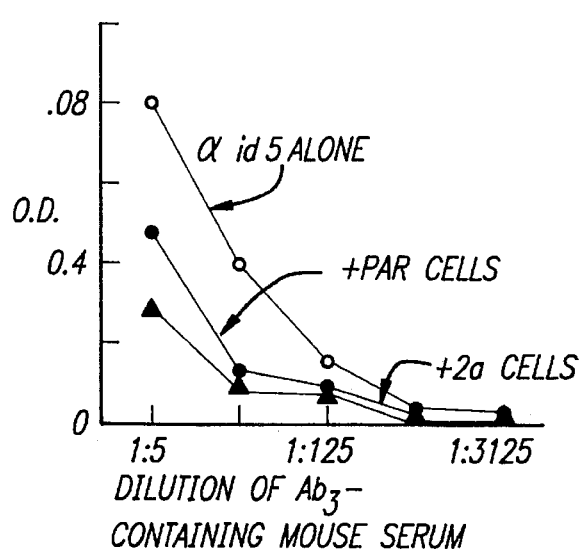
Figure 20A:
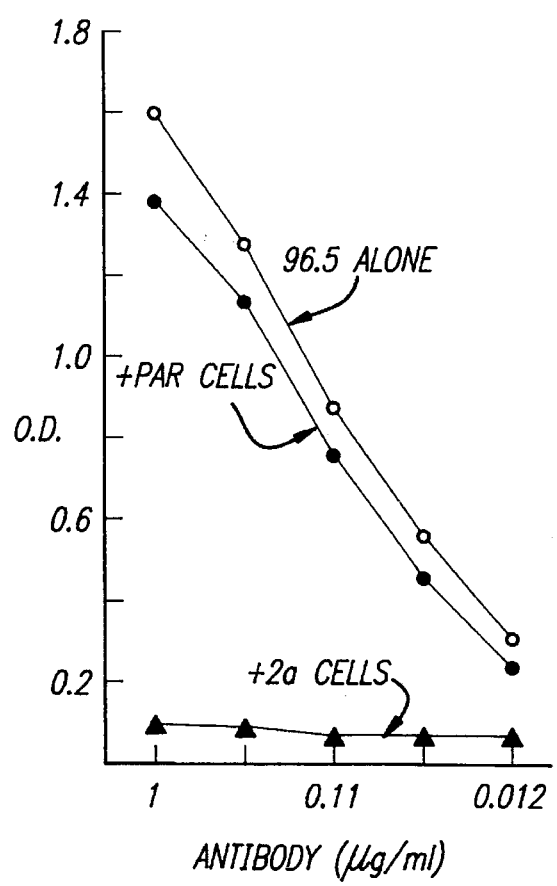
Figure 20B:
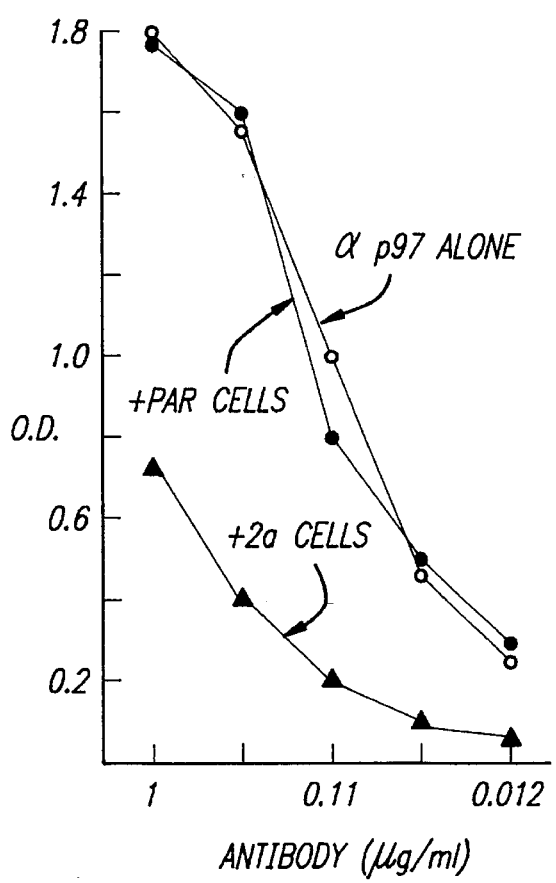
Figure 20C:
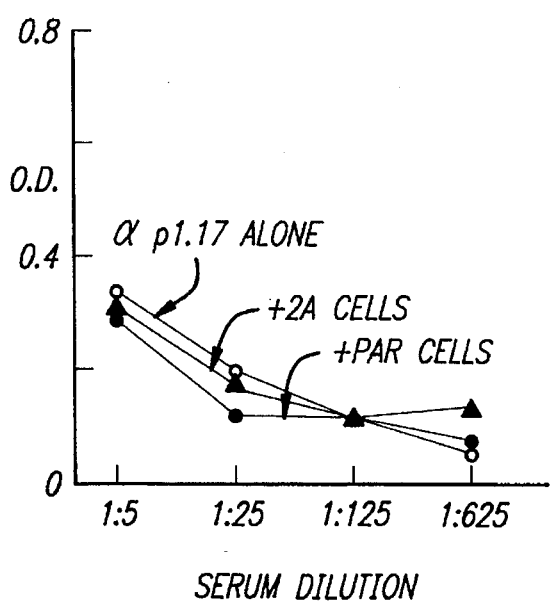
Figure 20D:
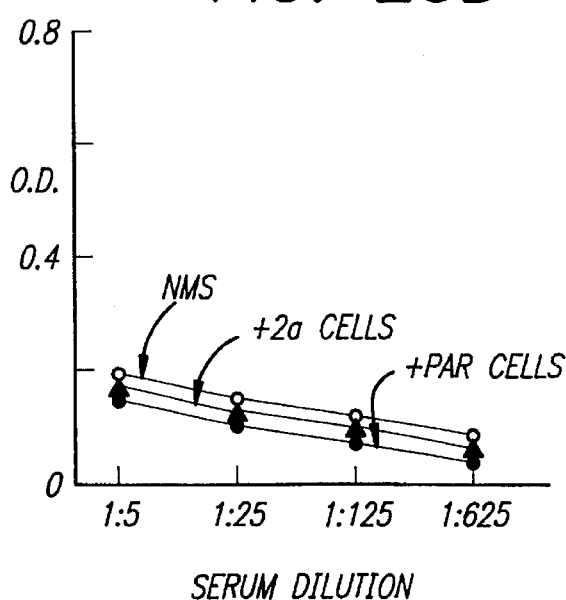

FIG. 16. Binding of plated anti-idiotypio antibody (Ab2) to different anti-p97 mAb, and the effect thereof on the ability of the anti-p97 mAb to subsequently bind p97. Each Ab2 was plated, various concentrations of anti-p97 mAb 8.2, 4.1, or 96.5 were added, and the binding of any bound anti-p97 mAb to radioiodinated p97 was measured.

FIG. 17. Binding of plated anti-idiotypic antibody (Ab2) to different anti-p97 mAb, and the effect thereof on the ability of the anti-p97 mAb to subsequently bind p97. Each Ab2 was plated, various concentrations of anti-p97 mAb 96.5 (Panel A, solid line), mAb 133.1 (Panel A, dashed line), or mAb 133.3 (Panel B) were added, and the binding of any bound anti-p97 mAb to radioiodinated p97 was measured.

FIG. 18. Panel A: Binding, to plated p97, of mouse sera containing Ab3. The sera were derived from BALB/c mice which had been immunized with anti-idiotypic antibodies conjugated to KLH. Panel B: Binding, to plated p97, of mAb 96.5 and of sera pooled from mice immunized to p97.

FIG. 19. Inhibition of the binding of p97 to Ab3, by p97-positive cells but not by p97-negative cells. p97-positive 2A (p97 gene-transfected mouse melanoma K-1735-M2) line) cells, but not p97-negative (parental K-1735-M2) cells, were able to inhibit the binding, to plated p97, of Ab3 from immunized BALB/c mice. Panel A shows data from mice immunized with Ab2 #3, and Panels B, C, and D show data from mice immunized with Ab2 #7, #4, and #5, respectively.

FIG. 20. Antibody binding to plated p97 was tested after absorption of the antibody with p97-positive 2A cells (2a), p97-negative parental K-1735-M2 cells (par), or antibody alone. Panel A: Absorption of mAb 96.5 with 2A cells inhibits the binding of mAb 96.5 to plated p97. Panel B: Absorption, with 2A cells, of serum antibodies (alphap-p97) from mice immunized with p97, inhibits the binding of the serum antibodies to plated p97. Panel C Serum antibodies (alpha p1.17) from mice immunized with p1.17 do not bind p97. Panel D: Normal mouse serum (NMS) does not bind p97.

Figure 21:
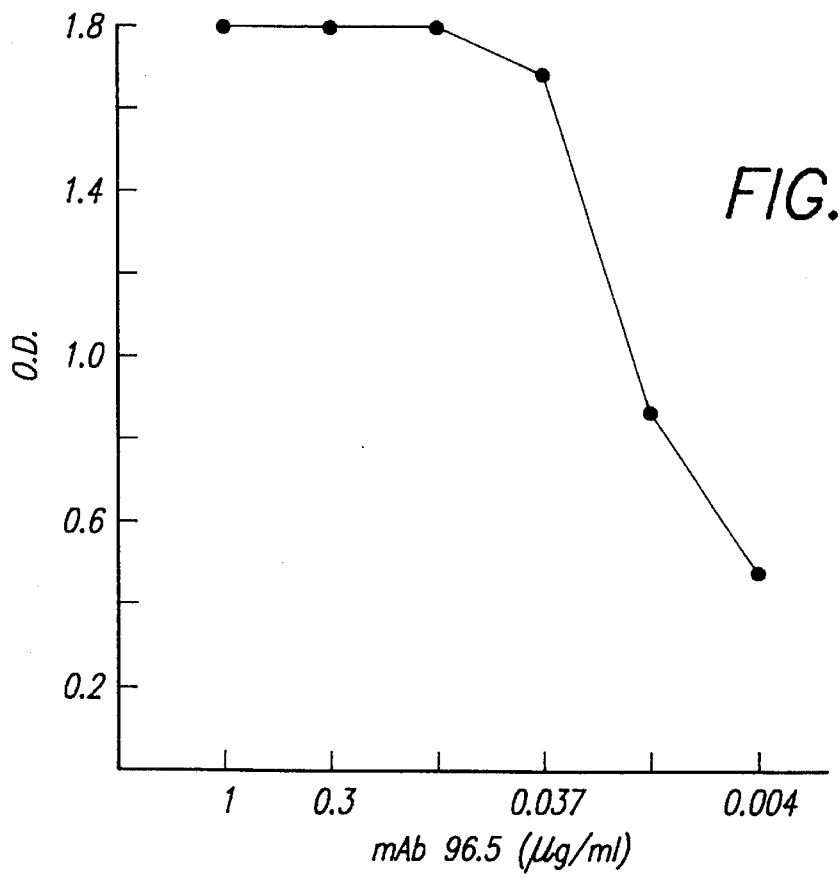

FIG. 21. Binding to plated p97 of Ab3 in serum of immunized mice. C3H/HeN mice were immunized with anti-idiotypic antibodies (Ab2) conjugated to KLH. Binding of Ab3 in serum from the immunized mice, to p97 antigen, was detected by a solid phase ELISA.

Figure 22:
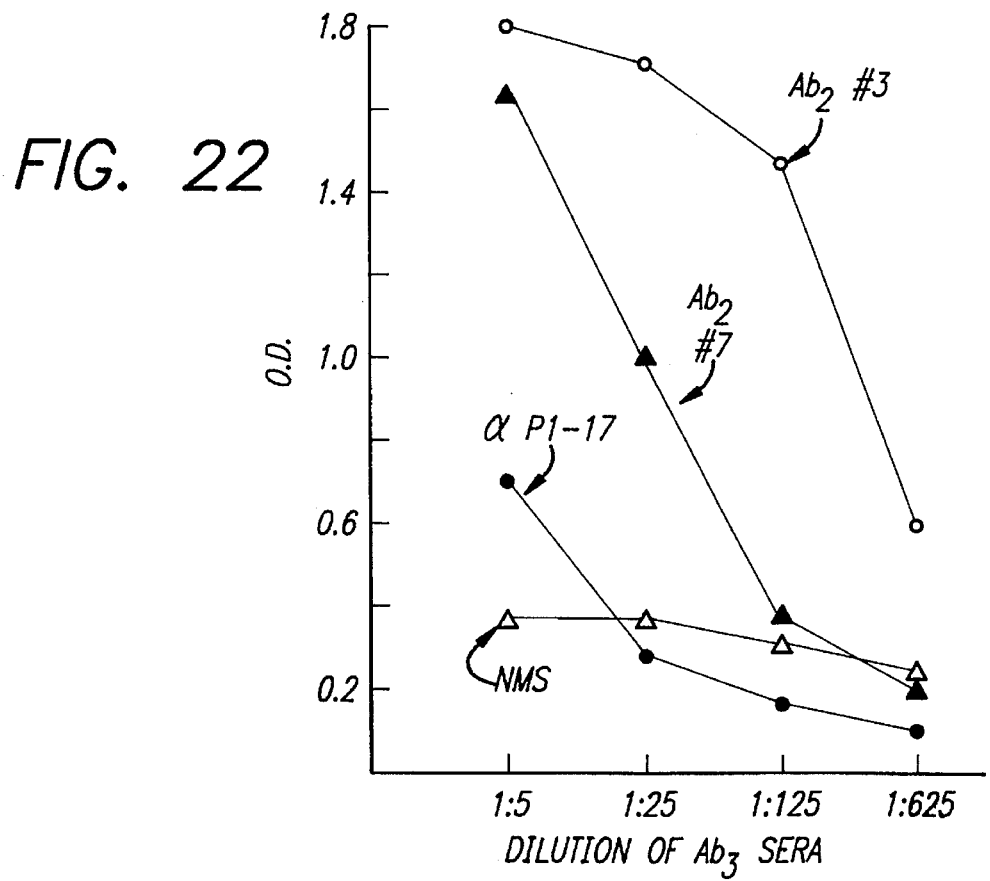

FIG. 22. Binding to plated p97 of mAb 96.5. Binding of anti-p97 mAb 96.5 to plated p97 antigen was detected by a solid-phase ELISA.

Figure 23:
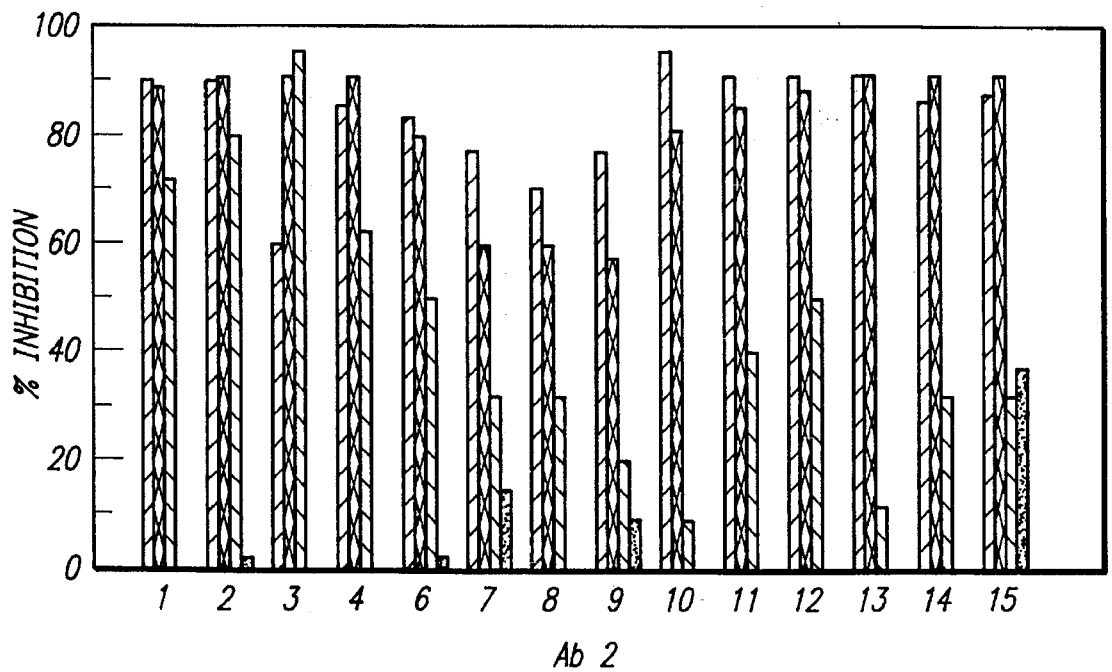

FIG. 23. Inhibition of the binding of mAb L6 to H-3347 carcinoma cells by purified Ab2. Ab2 concentrations were as follows: ▨ 50 µg/ml; ▩ 5.0 µg/ml; ▩ 0.5 µg/ml; ■ 0.05 µg/ml. mAb L6 was used at 1.0 µg/ml.

Figure 24A:
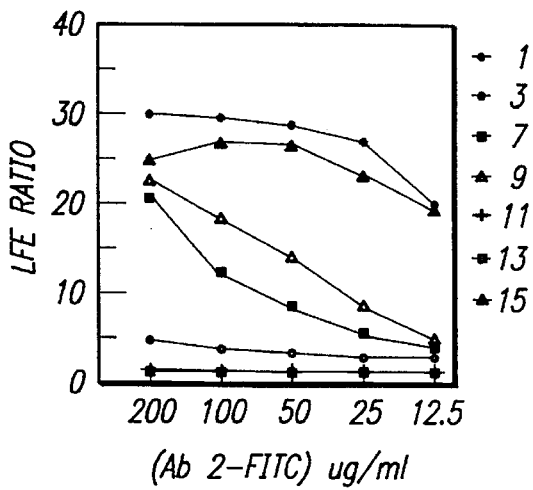
Figure 24B:
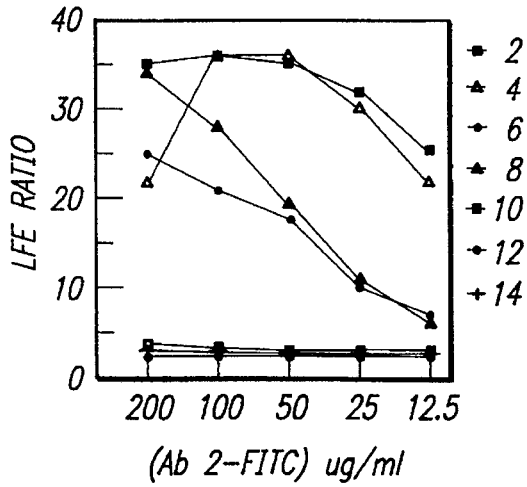
Figure 25A:
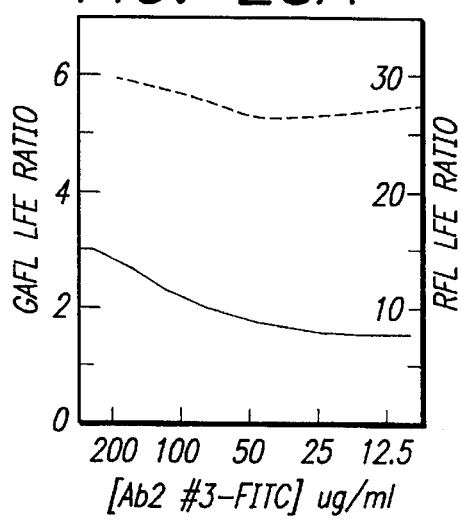
Figure 25B:
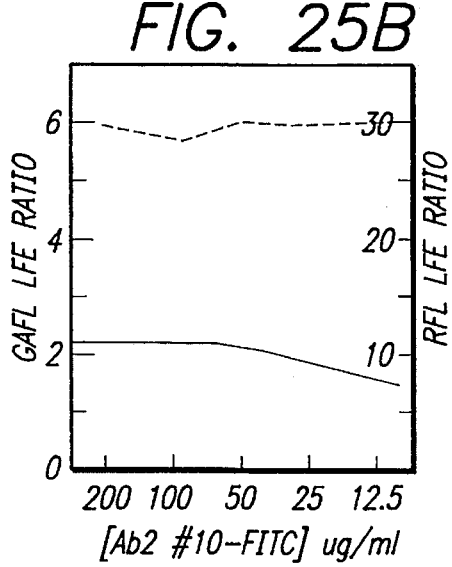
Figure 25C:
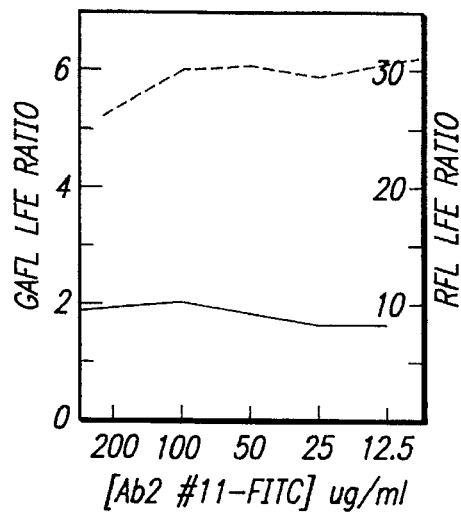
Figure 25D:
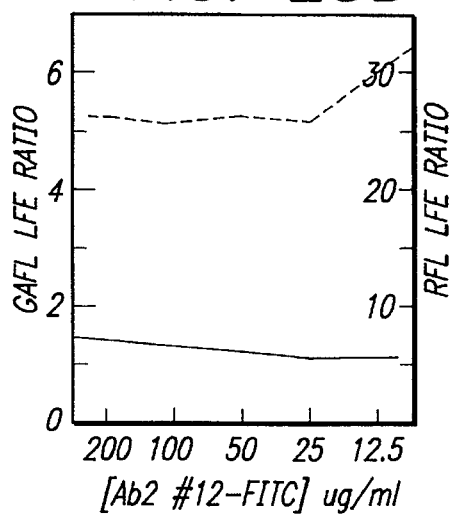
Figure 25E:
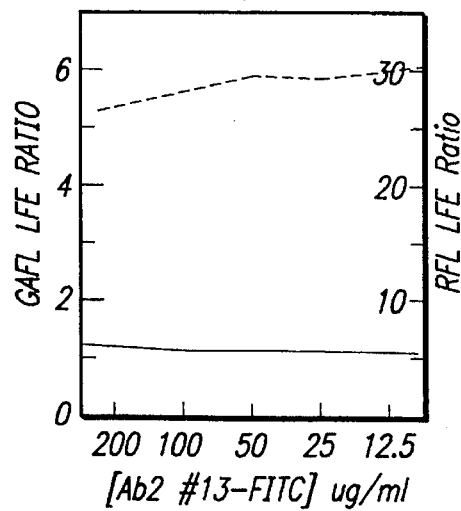
Figure 25F:
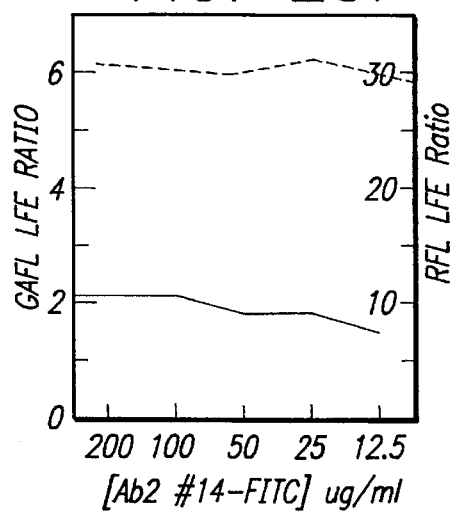

FIG. 24. Binding of FITC-labelled Ab2 to Fab L6 saturated H-3347 cells. Part A: Results are shown for the following Ab2: ● 1; -○-3; ●7; △-9; ★11; ▭ 13; ▲ 15. Part B: Results are shown for the following Ab2: ■ 2; -▲-4; ● 6; ▲ 8; ▭ 10; -○-12; ★ 1. LFE (linear fluorescence equivalent) Ratio is equal to the ratio of sample fluorescence to background fluorescence.

FIG. 25. Binding of FITC-labelled Ab2 to PE-labelled L6 saturated H-3347 cells. The tested Ab2 is indicated below each graph. — FITC-labeled Ab2; ---- Phycoerythrin-labelled mAb L6 at 1:25 dilution of approximately 1 mg/ml solution. RFL LFE Ratio: red fluorescence linear fluorescence equivalent (ratio of sample fluorescence to background fluorescence of phycoerythrin); GRFL LFE Ratio: green fluorescence linear fluorescence equivalent (ratio of sample fluorescence to background fluorescence of FITC)

Figure 26:
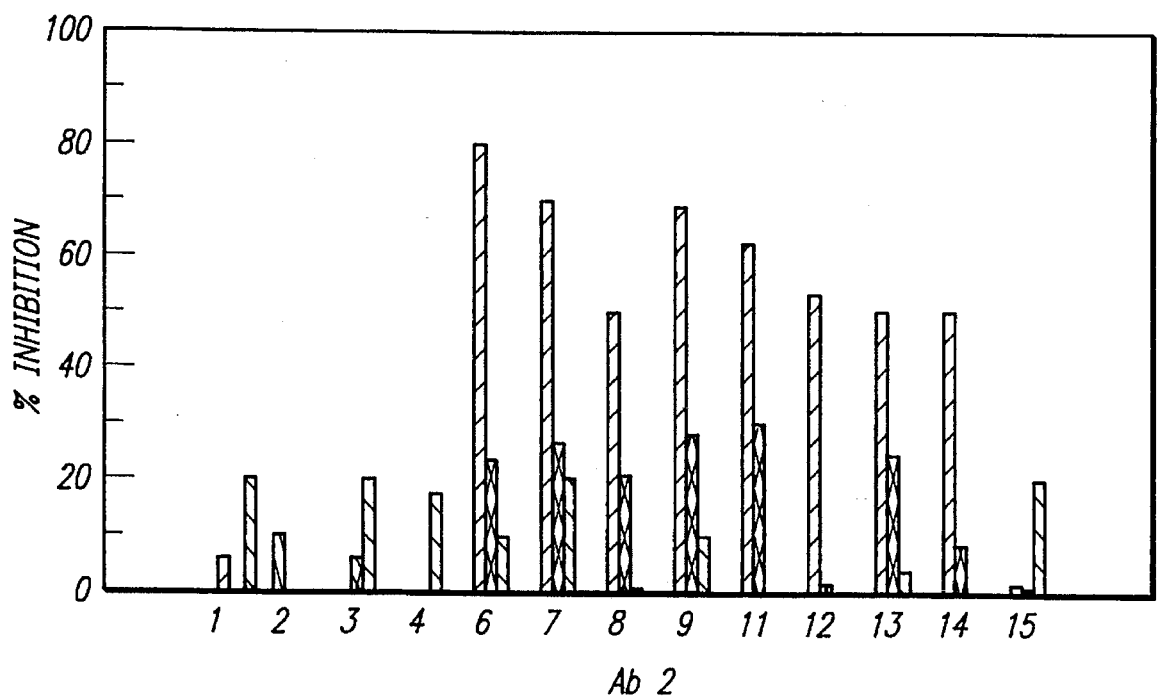

FIG. 26. Inhibition of binding of mAb F26 to H-3347 cells by L6 Ab2. Ab2 concentrations were as follows: ▨ 200 µg/ml; ▩ 20 µg/ml; ▧ 2.0 µg/ml. mAb F26 was used at 1.0 µg/ml.

Figure 27:
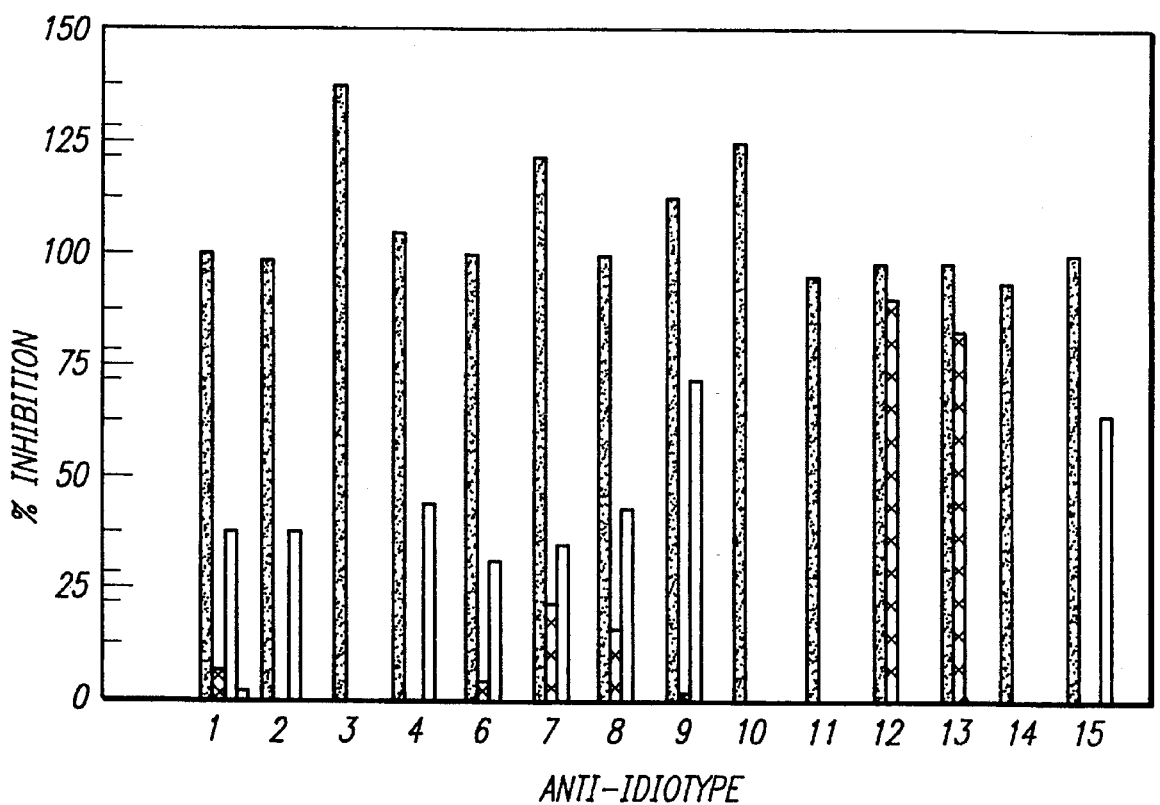

FIG. 27. Ab2 epitope specificity. Competition assays for L6 anti-idiotype variable region specificity were performed as described in Section 9.1.9, infra. Competitors were added at a concentration of 6 µg/ml for 0.5 hour prior to the addition of biotinylated chimeric L6 antibody, resulting in a final concentration of 4 µg/ml for the latter. Competitors were as follows: ■ chimeric L6 mAb; ▩ the variable heavy chain of chimeric L6 mAb plus J558L lambda I light chain; ▣ variable light chain of chimeric L6 mAb; ▧ irrelevant human IgG1 (PW P3281B8). The irrelevant human IgG1 showed no inhibition for any Ab2. Direct binding studies showed no recognition of any of the V-kappa Ab2 for the chimeric L6 heavy chain and vice versa.

Figure 28A:
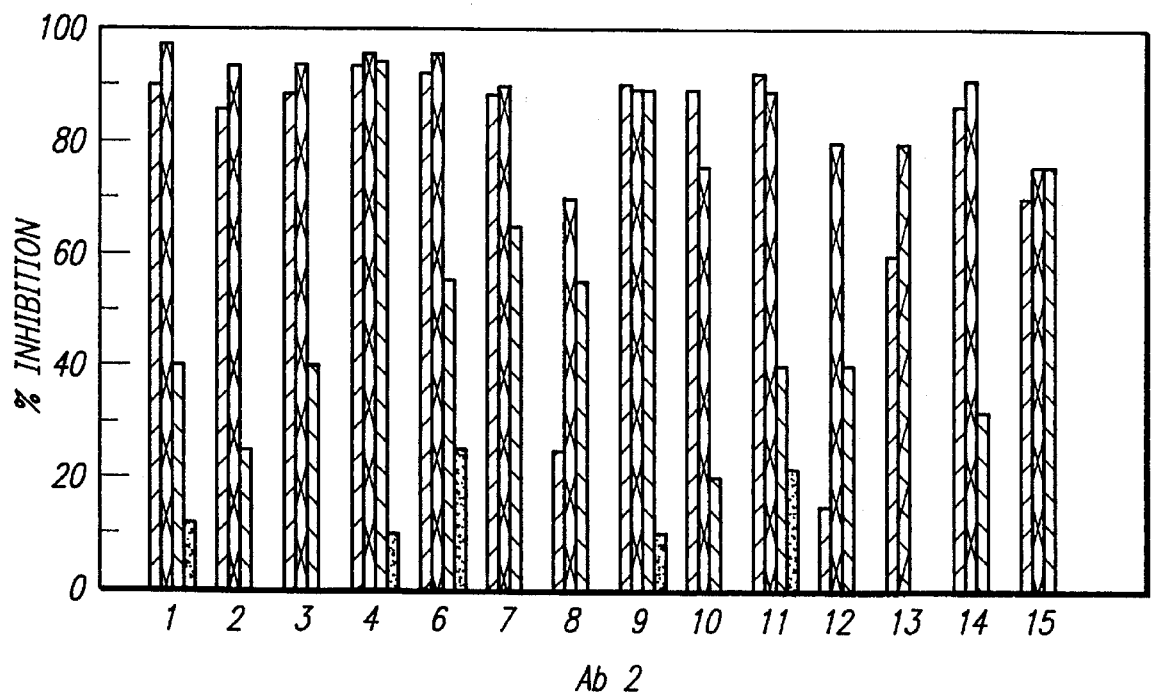
Figure 28B:
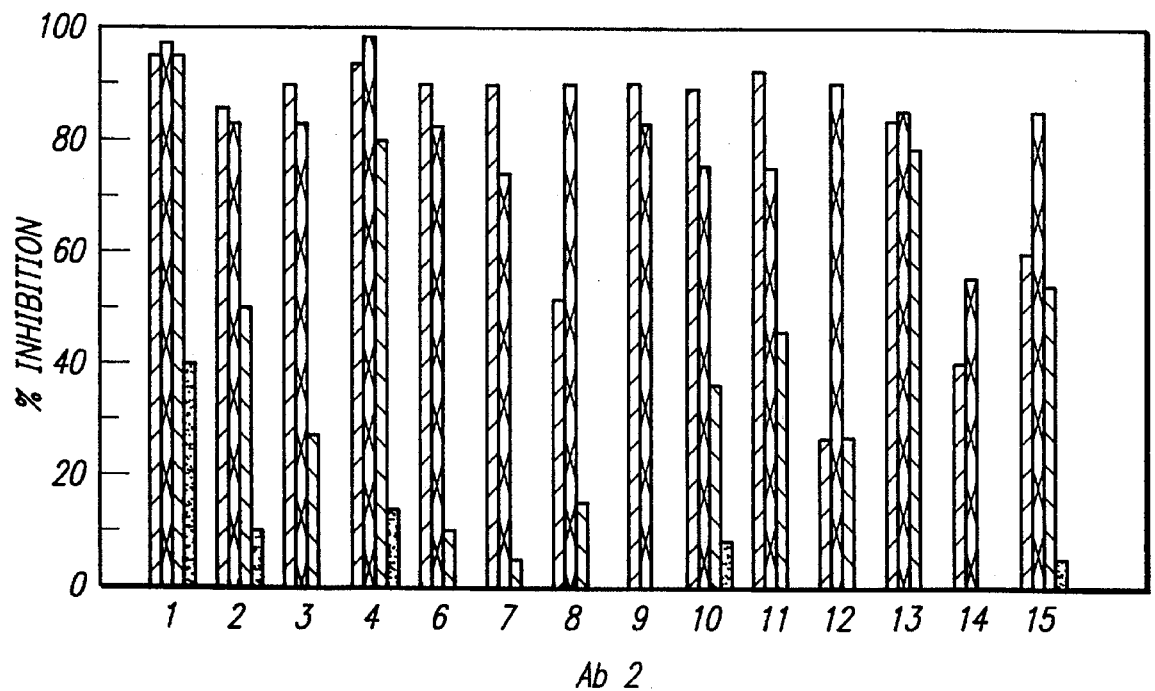

FIG. 28. Inhibition of binding of Ab2 to Ab1 in the presence of BALB/c (Part A) or C3H/HeN (Part B) sera containing Ab3. Dilutions of Ab3-containing sera were as follows: ▨ 1:20; ▩ 1:200; ▧ 1:2000; ■ 1:20,000. Ab2 was used at 1.0 µg/ml.

Figure 29:
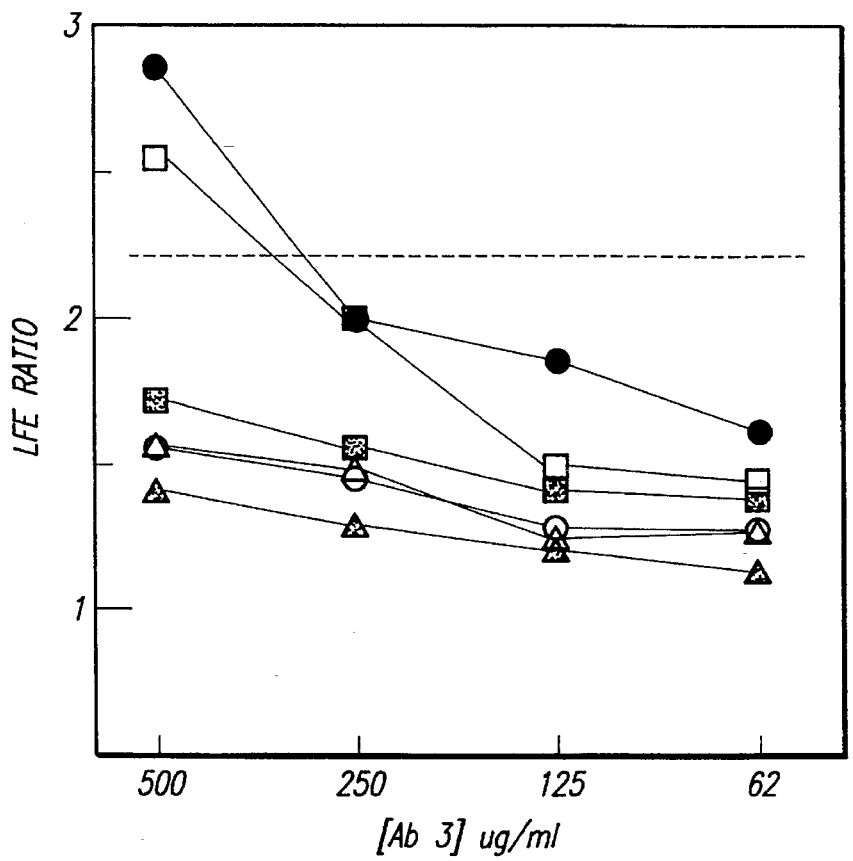

FIG. 29. Binding to H-3347 carcinoma cells of affinity-purified sera from C3H/HeN mice immunized with Ab2. Sera was taken 6 to 20 weeks after the first immunization. Antisera were as follows: — anti-P1-17; ■ anti-Ab2 #3; ▣ anti-Ab2 #11; ● anti-Ab2 #12; ◦ anti-Ab2 #13; ▲ anti-Ab2 #14; ▲ anti-Ab2 #15. The binding of mAb L6 at a concentration of 0.016 µg/ml (----) is also shown. LFE (linear fluorescence equivalent) Ratio is equal to the ratio of sample fluorescence to background fluorescence.

Figure 30:
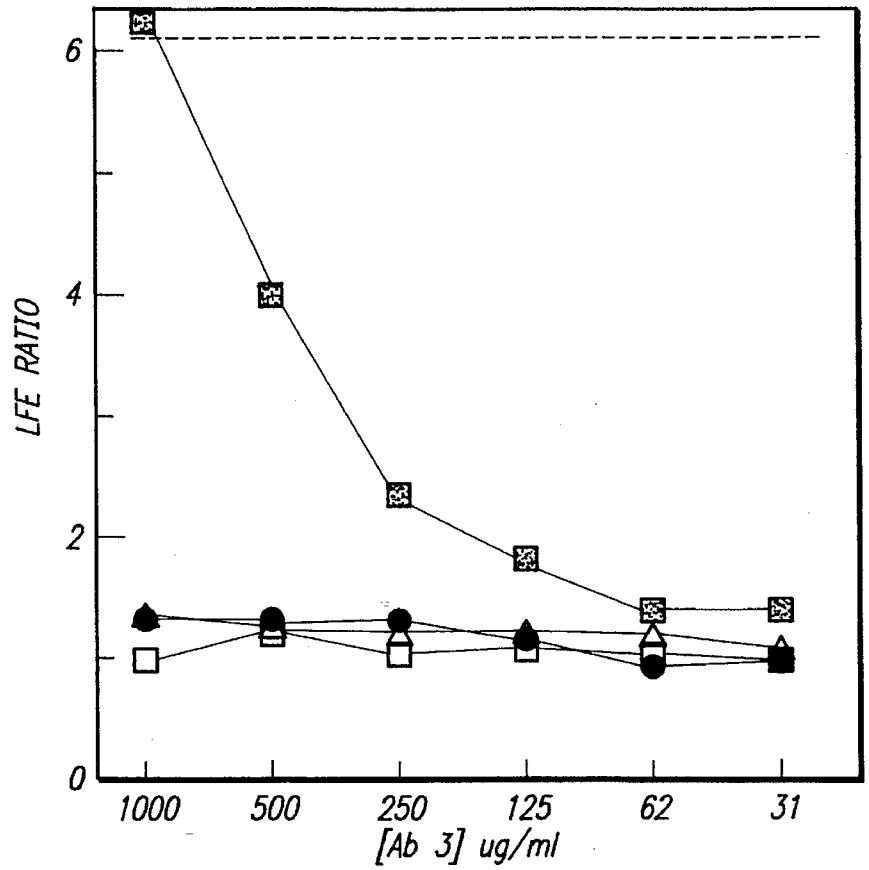

FIG. 30. Binding to H-3347 carcinoma cells of affinity-purified sera from BALB/c mice immunized with Ab2. Sera was taken 6 to 24 weeks after the first immunization. Antisera were as follows: — anti-P1-17; ★ anti-Ab2 #3; ● anti-Ab2 #11; ◦ anti-Ab2 #12; ▲ anti-Ab2 #13; ■ anti-Ab2 #14; ▣ anti-Ab2 #15. The binding of mAb L6 at a concentration of 0.08 µg/ml (----) is also shown. LFE (linear fluorescence equivalent) Ratio is equal to the ratio of sample fluorescence to background fluorescence.

5. DETAILED DESCRIPTION OF THE INVENTION

The present invention is directed to methods which utilize anti-idiotypic antibodies for tumor immunotherapy and immunoprophylaxis. The invention relates to the manipulation of the idiotypic network of the immune system for therapeutic advantage. Immunization with anti-idiotypic antibodies (Ab2) can induce the formation of anti-anti-idiotypic immunoglobulins, some of which have the same antigen specificity as the antibody (Ab1) used to derive the anti-idiotype. This creates a powerful paradigm for manipulation of immune responses by offering a mechanism for generating and amplifying antigen-specific recognition in the immune system. An immune response to tumors appears to involve idiotype-specific recognition of tumor antigen; the present invention relates to strategies for manipulating this recognition towards achieving therapeutic benefit. Particular embodiments of the invention include the use of anti-idiotypic antibody for immunization against tumor, for activation of lymphocytes used in adoptive immunotherapy, and for inhibition of immune suppression mediated by suppressor T cells or suppressor factors expressing an idiotope directed against a tumor antigen. The anti-idiotypic antibodies, or fragments thereof, can also be used to monitor anti-antibody induction in patients undergoing passive immunization to a tumor antigen by administration of anti-tumor antibody.

In a specific embodiment, the induction of anti-idiotypic antibodies in vivo, by administration of anti-tumor antibody or immune cells or factors exhibiting the anti-tumor idiotope, can be of therapeutic value.

In another embodiment of the present invention, monoclonal anti-idiotypic antibodies, or fragments thereof, raised against the idiotype of an antibody that defines a self-differentiation antigen, such as an oncofetal, or differentiation antigen can be administered in vivo to induce a specific immune response directed against tumor cells that bear the oncofetal antigen. Patients having tumors may be immunotherapeutically treated with the monoclonal anti-idiotypic antibodies of the present invention whereas patients identified as having a predisposition may be so treated immunoprophylactically.

The present invention is also directed to anti-idiotypic mAb molecules, or fragments of the anti-idiotypic mAb molecules, or modifications thereof, that recognize an idiotype that is directed against a defined antigen specific for a tumor. Such tumor antigens include antigens of fibrosarcoma, self-differentiation antigens such as oncofetal, or differentiation, antigens which are expressed by malignant cells, including but not limited to oncofetal antigens such as carcinoembryonio antigens (CEA) of the colon, alpha-fetoprotein, the human antigenic counterpart or functional equivalent of the 175 kDa murine antigen of transitional cell bladder carcinomas, the melanoma associated antigen p97 or GD3, and differentiation antigens of human lung carcinomas such as L6 and L20, described in more detail infra.

The mAb molecules of the present invention include whole monoclonal antibody molecules and fragments or any chemical modifications of these molecules, which contain the antigen combining site that binds to the idiotype of another antibody molecule(s) with specificity to a defined tumor antigen. Monoclonal antibody fragments containing the idiotype of the mAb molecule could be generated by various techniques. These include, but are not limited to the F(ab')$_2$ fragment which can be generated by treating the antibody molecule with pepsin, the Fab' fragments which can be generated by reducing the disulfide bridges of the F(ab')$_2$ fragment, and the 2Fab or Fab fragments which can be generated by treating the antibody molecule with papain and a reducing agent to reduce the disulfide bridges.

Depending upon its intended use, the molecules of the invention may be chemically modified by the attachment of any of a variety of compounds using coupling techniques known in the art. This includes but is not limited to enzymatic means, oxidative substitution, chelation, etc., as used, for example, in the attachment of a radioisotope for immunoassay purposes.

The chemical linkage or coupling of a compound to the molecule could be directed to a site that does not participate in idiotype binding, for example, the F$_c$ domain of the molecule. This could be accomplished by protecting the binding site of the molecule prior to performing the coupling reaction. For example, the molecule can be bound to the idiotype it recognizes, prior to the coupling reaction. After completion of coupling, the complex can be disrupted in order to generate a modified molecule with minimal effect on the binding site of the molecule.

The antibodies, or fragments of antibody molecules of the invention, can be used as immunogens to induce, modify, or regulate specific cell-mediated tumor immunity. This includes, but is not limited to, the use of these molecules in immunization against syngeneic tumors.

The method of the invention may be divided into the following stages solely for the purpose of description: (a) production of anti-idiotypicmAb(s) (which may be auto-anti-idiotypic) directed against an idiotype which binds a defined antigen of a tumors (b) evaluation and demonstration of tumor idiotype specificity of the anti-idiotypic mAb molecules or their derivative fragments, for example, by demonstration of immunopotency by induction of specific CMI, of binding to specific suppressor T cells or suppressor factors, of binding to specific helper T cells, of inhibition of the binding of antibody directed against the tumor antigen, of inhibition of the cytotoxicity properties of the antibody directed against the tumor antigen, etc. and (c) formulation of immunoprophylactic, immunotherapeutic, and immunodiagnostic regimens.

In a model system described in a specific example of the present invention, treatment of mice with auto-anti-idiotypic antibodies related to a fibrosarcoma antigen was shown to specifically reduce the growth of established satcomas. In another example of the invention, a murine monoclonal anti-idiotypic antibody which recognizes an idiotype directed against a GD3 ganglioside antigen of human melanoma is described. This antibody was able to block the binding and cytotoxicity properties of the antibody containing the idiotype which it recognizes. In a third example of the invention, murine monoclonal anti-idiotypic antibodies related to the human melanoma-associated p97 antigen were described, which antibodies can competitively inhibit the binding of p97 to anti-p97 antibody, and which can induce antibodies to p97 in vivo. In yet another example of the invention, we describe the generation and characterization of murine monoclonal anti-idiotypic antibodies which recognize an idiotype on monoclonal antibody L6 which defines a carbohydrate antigen of human carcinomas. Several of the antibodies are shown to be capable of inducing antibodies in vivo to the carcinoma antigen defined by antibody L6. However, the methods described are not limited to melanoma or fibrosarcoma or carcinoma antigens, but can be applied to the production and use of anti-idiotypic mAbs related to any specific tumor antigens.

The use of anti-idiotypic antibodies to induce immune responses to tumors can be viewed as two separate issues. First, such antibodies may be used to select or amplify a pre-existing antitumor repertoire, that is, to recruit, via idiotypic selection, T and/or B cells with specificity for tumor antigen. Second, anti-idiotypic antibodies can be employed as "internal images" of antigens to induce a primary immune response which is anti-anti-idiotypic, and a portion of which is directed against the nominal tumor antigen. In the latter case, the immune specificity will be against anti-idiotope, rather than antigen.

By using anti-idiotypic antibodies to induce immunity, T and B cells may be selected which are different from those which participate in a naturally occurring antitumor response, either as a result of upregulation of an immune response that is normally suppressed or by the de novo induction of a response. Of significant therapeutic importance is the potential to induce effective antitumor reactivity in hosts which are otherwise incapable of mounting such reactivity.

5.1. Idiotypic Interactions Initiated By Antigenic Stimuli

In order to effect therapeutic manipulations of the idiotypic recognition of tumor antigens, one must consider the nature of the naturally occurring idiotypic response to a growing syngeneic tumor. We shall thus discuss the nature of the idiotypic repertoire in the response to stimulation with any antigen.

Four possible idiotypic and anti-idiotypic responses which can be induced by antigens are illustrated in FIG. 1. FIG. 1A shows a sequential progression of induced complementary specificities. In this type of idiotypic cascade, immunization with antigen leads to a population of immunoglobulins which carry distinct idiotypes, the sum of which is known as the idiotype or AB1 response. The presence of the AB1 then induces an anti-idiotypic response, characterized by a heterogeneous population of antibodies, known as Ab2, which have specificity for the various idiotypes in the AB1 population. Directionality of the antigen-elicited response is implied by the arrows in FIG. 1. The induction of Ab2 by AB1 is independent of antigen (Urbain, J., et al., 1982, Ann. Immunol. 133D:179–189; Rodkey, L. S., 1974, J. Exp. Med. 139:712; Kelsoe, G. and Cerny, J., 1979, Nature 279:333). There is support for this model (FIG. 1A) in tumor immunity (Lee, V. K., et al., 1986, Biochim. Biophys. Acta 865:127–139; see examples sections infra).

An idiotypic cascade may also lead to the generation of Ab2 according to the pathway shown in FIG. 1B. Tumor antigen recognition induces antigen-spectfic $T_H$ cells, which bear particular idiotypes, presumably on their antigen receptor molecules. These T cells then stimulate the generation of an anti-idiotypic immunoglobulin response in the form of a population of Ab2.

What are the implications of a model in which the idiotypic cascade proceeds through alternate antibody and T cell components? In an analysis of idiotopes associated with the response to MCA-induced mouse satcomas or carcinomas (Lee, V. K., et al., 1986, Blochim. Biophys. Acta 865:127–139; see examples sections 6,7,8, infra), immunization with monoclonal Ab2 failed to generate Ab3 with Ab1-like specificity, whereas antitumor $T_H$ were easily induced. This observation, coupled with the finding of idiotype-positive $T_H$ in the naturally occurring antitumor response, supports a model in which there can be a direct regulatory interaction between Id+ T cells and anti-idiotypic B cells (and Ab2) (Nelson, K. and Nepom, G. T., 1986, in Paradoxes in Immunology, Hoffman, G., et al., eds., CRC Press, Boca Raton, Fla., pp. 177–185; Bismuth, G., et al., 1984, Eur. J. Immunol. 14:503; Thomas, W. R., et al., 1983, J. Immunol. 130:2079). In vivo, the Id+ T cells can provide the stimulus for production of anti-idiotype.

The lack of Id+ B cell recognition in certain cases, may reflect a defect in the genetic capacity to generate antitumor idiotopes on immunoglobulin molecules; alternatively, the regulatory state in the tumor-bearing host may effectively suppress Id+ Ab1. As discussed infra (see Section 5.2.1), this apparent defect may be circumvented therapeutically in a host which does not normally develop Id+ antibody responses.

In addition to idiotypic interactions which result in a $T_H$ response leading to tumor rejection, exposure to tumor antigen (or antigen-antibody complexes) can lead to the generation of antigen-specific suppressor T cells ($T_S$) (FIG. 1C). In several tumor systems, suppressor T cells have been shown to function as inducer cells, triggering and amplifying tumor antigen-specific suppression (Nepom, G. T., et al., 1983, Experientia 39:235–242). If Id+ $T_S$ are directly induced by antigen stimulation, as in the model shown in FIG. 1C, it is possible that these cells, like the $T_H$ in FIG. 1B, can serve as stimuli for the generation of anti-idiotypic Ab2.

In a model where idiotypic $T_S$ are generated subsequent to stimulation by antigen, an alternate pathway can also be considered. As diagramed in FIG. 1D, Id+ $T_S$ may arise as a consequence of anti-idiotypic stimulation. In a recent analysis of IgH-restricted T cell responses to the hapten azobenzenearsonate, the nature of immunoglobulin idiotopes was found to determine the development of $T_S$ idiotopes (Hayglass, K., et al., 1986, J. Exp. Med. 164:36–49; Hayglass, K., et al., 1986, Immunol. Today 7:179–183). T cells developing in IgH congenic mice acquired the idiotypic repertoire of the host, and treatment of neonatal animals with antibodies to the µ immunoglobulin chain abolished the establishment of a normal repertoire of functional T cell idiotypes. Thus, the immunoglobulin compartment could determine the development of complementary T cell recognition elements.

As illustrated by the examples sections infra, the idiotypic pathway depicted in FIG. 1D appears to exist also in the context of tumor antigen recognition. In our studies on mice which had either sarcomas or bladder carcinomas induced with MCA, a single dominant T cell idiotope was found to be prevalent in the suppressor response mediated by both $T_S$ and soluble factors (see Kuchroo, V. K., et al., 1987, Cellular Immunol. 104:105–114, and examples section 6, infra). That is, instead of a heterogeneous mixture of idiotypes, some shared "public" idiotopes predominate. This was documented by removing suppressor factors using affinity absorbents made from either monoclonal or polyclonal anti-idiotypic antibodies. Our findings indicated that most of the apparent idiotypic specificities in the suppressor response to any particular tumor antigen are shared.

In model systems, the presence of "public" idiotopes has been attributed to regulatory idiotopes important for network interactions (Bona, C., et al., 1982, J. Exp. Med. 156:986). The presence of such putative regulatory idiotopes in anti-tumor immunity may reflect either a genetic selection in the generation of idiotypic $T_S$, or an influence of immunoglobulin selection in the generation of the $T_S$ repertoire. If the latter is the case, the induction of idiotypic $T_S$ can include the pathway we have shown in FIG. 1D, in which the Ab2 response influences the nature of $T_S$.

5.2. Manipulation of Idiotope Expression By Anti-Idiotypic Antibodies

There are essentially two approaches for using anti-idiotypic antibodies to manipulate the immune response to tumor antigens for therapeutic benefit. One is based on selecting and amplifying pre-existing antitumor idiotopes within the T and B cell repertoires, and the other entails the priming of a de novo response using an anti-idiotype which acts as an internal image of tumor antigen.

5.2.1. Selection and Amplication of Pre-Existing Antitumor Idiotopes

In the therapeutic production of anti-idiotypio antibodies based on an alteration of preexisting antitumor idiotope representation, therapeutic efforts are based on a reversal of the pathways illustrated in FIG. 1, in which the Ab2 compartment is used as the initiator of idiotypic interactions.

Three pathways by which Ab2 can induce tumor antigen-specific immunity are illustrated in FIG. 2. FIG. 2A shows that immunization with Ab2 can lead to the development of antigen specific $T_H$. This result has been accomplished against infectious agents and found to give protection from disease (Sacks, D., et al., 1982, J. Exp. Med. 155:1108; Sharp, A., et al., 1984, J. Exp. Med. 160:1195–1205; Fons, G., et al., 1985, J. Immunol. 134:1225–1229). Analogous findings have been made for several chemically and vitally-induced tumors (Kennedy, R. C., et al., 1985, J. Exp. Med. 161:1432; Binz, H., et al., 1982, Int. J. Cancer 19:417–423; Tilken, A. F., et al., 1981, Proc. Natl. Acad. Sci. U.S.A. 78:1809; Flood, P., et al., 1980, Proc. Natl. Acad. Sci. U.S.A. 77:2209–2213). The Ab2 which is utilized can arise as a result of an antigen-induced idiotypic cascade, or can be induced by immunization with antigen-specific T cells (see Section 5.3, infra).

Anti-idiotypic antibodies can also stimulate "silent" clones; i.e., clones which are normally suppressed even in genetically competent individuals (Bona, C. A., et al., 1981, J. Exp. Med. 153:951). Thus, the anti-idiotypio antibodies appear to be able to "reprogram" the immune system to generate antibodies which would not otherwise be made (FIG. 2B). Thus, immunization with anti-idiotypic antibodies related to capsular polysaccharides of E. coli produces protective immunity in neonatal mice that do not normally develop antibodies against the capsular polysaccharides (Stein, K., et al., 1984, J. Exp. Med. 160:1001).

For Ab2 to select and stimulate both id+ B and T cell clones, it is probable that shared idiotopes between B and T cell receptors must exist (Rajewski, K. and Takemori, T., 1983, Ann. Rev. Immunol. 1:569–607; Ertl, H. C. J., et al., 1982, Proc. Natl. Acad. Sci. U.S.A. 79:7479; Nadler, P. I., et al., 1982, Eur. J. Immunol. 12:113), and correspond to antigen-specific receptors which confer the same antigen specificity for both B and T cells. In a preferred embodiment of the invention, one can select for use in immunization those Ab2 which induce T cell immunity, in which a T cell subset is stimulated which mediates the desired response. One technique to select appropriate Ab2 for use is to raise Ab2 experimentally by immunization with antigen-specific T cells (Infante, A. J., et al., 1982, J. Exp. Med. 155:1100). In this particular embodiment of the invention, the T cell receptor is used as the stimulatory idiotype so that the Ab2 population will be targeted specifically to the T cells of choice. Immunization with such an Ab2, then, will select and stimulate T cell clones which share receptor idiotopes with the immunizing cells.

Several investigators have reported successful cloning of tumor-infiltrating T lymphocytes recovered from tumor biopsies or surgical specimens. These lymphocytes, after culture in vitro with IL-2, are effective in eliciting antitumor responses when reinfused to the host (Rosenberg, S. A., et al., 1986, Science 233:1318). In a preferred embodiment of the invention, such cells should be ideal immunogens for raising Ab2 directed against the particular idiotopes associated with such antitumor clones. These Ab2, then, would serve as anti-idiotypes which potentially will select and amplify T cells with similar antitumor specificity.

As discussed supra, anti-idiotypic specificities in tumor-immunized mice appear to be complementary not only to $T_H$ but also to $T_S$ and soluble suppressor factors (Hellstrom, K. E., et al., 1977, Biophys. Blochim. Acta Reviews on Cancer 473:121–148; see Section 8, infra; Binz, H., et al., 1982, Int. J. Cancer 19:417–423; Tilken, A. F., et al., 1981, Proc. Natl. Acad. Sci. U.S.A. 78:1809; Flood, P., et al., 1980, Proc. Natl. Acad. Sci. U.S.A. 77:2209–2213). The evidence that anti-idiotypic antibodies recognize a dominant public idiotope on $T_S$-derived factors suggests that there is a regulatory relationship between the id+ cellular compartment and the Ab2 compartment (see Section 6, infra; Kuchroo, V. K., et al., 1987, Cellular Immunol. 104:105–114; Nelson, K. and Nepom, G. T., 1986, in Paradoxes in Immunology, Hoffman, G., et al., eds., CRC Press, Boca Raton, Fla., pp. 177–185). Thus, in order to avoid the preferential activation of the $T_S$ compartment upon administration of anti-idiotypic antibodies (as illustrated in FIG. 2C), and in order to achieve a therapeutically effective result, anti-idiotypic therapy for cancer should employ proper manipulation of the idiotypic networks. Proper manipulation involves the consideration of three issues: the genetic restriction between anti-idiotype and the T cell compartments the route of anti-idiotype administration; and the choice of idiotope specificity.

5.2.1.1. Genetic Restriction

Two types of genetic restriction can potentially present barriers to cellular recruitment by injected anti-idiotypes: MHC restriction and IgH restriction. MHC restriction confers an element of genetic control of T cell activation in an antigen-specific response. To the extent that an anti-idiotype mimics antigen in the recognition process, it is logical to consider possible requirements for histocompatibility. Indeed, examples have been reported in which antigen-primed T cells are MHC restricted not only for their specific antigen recognition, but also for their ability to recognize cell-bound anti-idiotype in vitro (Ertl, H., et al., 1986, Int. Rev. Immunol. 1:61–66).

What are the implications of these findings for the $i_n$vivo administration of anti-idiotype? In a study using anti-idiotype priming to generate anti-vital immunity, a genetically non-restricted response was observed (id.). This may have been due to the direct recruitment of $T_H$ which subsequently activated other T cell compartments. Thus, even if the MHC restricting element for anti-Id presentation is different from that of nominal antigen presentation, T cell recruitment can still occur. With an appropriate route of administration (see below), anti-idiotypic antibodies can be introduced to the immune system by antigen-presenting cells in such a way that they may be "seen" in the context of the right restriction elements. In fact, a host which is a genetic non-responder to the nominal antigen can conceivably respond to challenge with anti-idiotype, depending on the mechanism maintaining the non-responsiveness. Thus, MHC restriction appears to be of minor importance except where cell-bound anti-idiotype is used. In a preferred embodiment of the invention, anti-idiotype administration should seek to optimize the presentation of the Ab2 immunogen to the host immune system, even where MHC-incompatible.

In a preferred embodiment of the invention, the issue of IgH restriction, i.e., the necessity for genetic matching of allotypic markers associated with immunoglobulin genes, should be considered. Since variable region antibody genes are linked to constant region genes, the genetic potential for specific idiotypic determinants is linked to Ig allotypic markers. IgH restriction appears to govern many steps in the idiotypic cascade (Bach, B. A., et al., 1979, J. Exp. Med. 149:1084; Nadler, P. I., et al., 1982, Eur. J. Immunol. 12:113; Yamamoto, H., et al., 1983, J. Exp. Med. 158:635–640; Forstrom, J. W., et al., 1983, Nature 303:627–629). In essence, it acts as a permissive barrier which requires the presence of appropriate V genes, and linked allotypic markers, for idiotype-anti-idiotype recognition.

A strict IgH restriction of the immune response to Ab2 likely reflects requirements for direct recognition of network V genes; this has been referred to as a "true idiotypic" interaction (Nisonoff, A. and Lamoyi, E., 1981, Clin. Immunol. Immunopathol. 21:397). This requirement limits the type of antibody which can be used as an anti-idiotype immunogen, to one which can elicit complementary V genes in the host. Thus, in a particular preferred embodiment of the invention, experimentally derived anti-idiotypic antibodies should be IgH-matched with the host.

When is IgH-matching for anti-idiotypic administration not necessary? Anti-idiotypic antibodies which act as internal images of the nominal antigen can substitute for this immunization with antigen. Since such de novo immunization is not based on specific selection of network V genes, internal image immunogens are generally not IgH restricted (id.), and thus do not need to be host IgH-matched.

5.2.1.2. Route of Immunization

The route of immunization with anti-idiotype can also influence the nature of the immune response. Depending upon the route of administration, anti-idiotypic antibodies have been found to either enhance or suppress immune responses (RaJewski, K. and Takemori, T., 1983, Ann. Rev. Immunol. 1:569; Urbain, J., et al., 1982, Ann. Immunol. 133D:179). For example, in a vital system, reovirus-specific immunity could be established following immunization against idiotypic determinants, and DTH, cytolytic T cells, and antigen-binding antibodies were observed. If soluble Ab2 was used as the immunogen, only the DTH response was seen, while immunization with cell-associated anti-idiotype, in the form of a hybridoma-producing Ab2, also induced cytolytic T cells (Ertl, H., et al., 1986, Int. Rev. Immunol. 1:61–66). When Ab2 is used as an internal-image immunogen (as in the reovirus system), it essentially substitutes for antigen in the initial priming; many of the immune manipulations which facilitate antigen responsiveness also augment immunity to Ab2 and can be used in various embodiments of the invention (see Section 5.3.2, infra).

Many methods may be used to introduce the immunizing formulations; these include but are not limited to intradermal, intramuscular, intraperitoneal, intravenous, subcutaneous, and intranasal routes. In particular embodiments, induction of immunity with anti-idiotypic antibodies can utilize subcutaneous (s.c.) or intramuscular injection of the antibodies in the presence of various adjuvants.

In the case of nominal antigen immunization, administration of a haptenated protein s.c. with adjuvant has been shown to yield a vigorous $T_H$ response, while the same antigen intravenously (i.v.) preferentially induced $T_S$ (Greene, M., et al., 1982, Adv. Immunol 32:253). However, when monoclonal antitumor antibodies were used therapeutically, the opposite situation was reported by Koprowski et al. (Koprowski, H., et al., 1984, Proc. Natl. Acad. Sci. U.S.A. 82:216–219), who described an anti-idiotypic response to systemically injected mouse antibodies to human gastrointestinal cancer, which was apparently accompanied by a therapeutic effect in the patient.

There is also evidence that Ab2 can effectively inhibit the ability of an AB1 to mediate antibody-dependent cellular cytotoxicity or kill tumor cells in the presence of complement (see Section 7.2.4, infra).

Since route of Ab2 administration, as well as dosages used, are likely to have an important impact on what kind of response is induced, in a preferred aspect of the invention, preliminary studies on dosage and administration effects should be carried out. These studies can be done in an animal model such as mouse, rat, primate, etc. For example, in a particular embodiment, various routes of administration of anti-idiotypic antibody related to the melanoma antigen p97 can be tested for the in vivo and in vitro responses which they induce upon challenge with a mouse melanoma line expressing the p97 antigen (obtained following transfection with the cloned p97 gene; see copending U.S. application Ser. No. 827,313, filed Feb. 7, 1986; Brown et al., 1981, J. Immunol. 127:539–546).

5.2.1.3. Idiotope Specificity

Complex antigens, including tumor antigens, contain multiple epitopes. The immune recognition which they evoke, therefore, contains many idiotopes which are determined not only by the heterogeneity of the epitopes, but also by the heterogeneity of the V genes selected among Ig and T cell receptor genes in the host. These idiotopes are largely defined by the anti-idiotopes which they induce. Thus private idiotopes elicit Ab2 responses which are unique for a particular Ab1, public idiotopes elicit Ab2 to a specificity shared by many Ab1, and Ab2 of the internal image type are induced against antigen-binding structures on AB1 which are complementary to the antigen (Urbain, J., et al., 1982, Ann. Immunol. 125C: 373–389; Augustin, A., et al., 1983, Surv. Immunol. Res. 2:78; Mosier, D. and Feeney, A., 1984, in The Biology of Idiotypes, Greene, M. and Nisonoff, A., eds., Plenum Press, New York, pp. 403–416).

In particular embodiments of the invention, likely shifts in the idiotypic repertoire can be manipulated in an attempt to achieve the desired idiotypic response. For example, idiotope selection depends in large part on the Ab2 used as immunogen. Thus, in a preferred embodiment, an Ab2 used as immunogen is one determined to be likely to cause the expression of therapeutically desirable idiotopes. For example, in a system with a dominant public idiotope on both $T_H$ and $T_S$ cells, anti-idiotypic antibodies may prime for $T_H$, if administered s.c. with adjuvant, or they may interact with soluble $T_S$ factors. As an illustration, in studies in mice which were immune to haptens and in which public idiotopes were recognized, a dominant AB1 response with a shared public idiotope elicited a strong anti-Id response in mice of IgH-compatible strains. If anti-Id was given i.v. in neonates, or if anti-Id $T_S$ were transferred, the public AB1 idiotope was suppressed, and this was shown to cause the expression of alternate idiotopes on antigen-specific Ab1 (Kekoe, G., et al., 1980, Immunol. Rev. 52:75). When immunization with anti-Id is applied towards tumor therapy, a similar shift in the idiotypic repertoire can occur.

In a system lacking a dominant public idiotope, or when no AB1 is identified, the adaptability of the idiotope selection process offers encouraging alternatives. In a particular embodiment of the invention, since administration of Ab2 can select for alternate idiotypic responses, antibodies to idiotopes which do not occur naturally in the tumor-bearing host can be chosen to direct an antitumor response. In other words, one can immunize with an Ab2 which selects a $T_H$ repertoire which cannot be selected by exposure to tumor antigen. For example, one can immunize with a monoclonal, internal-image Ab2 raised against a xenogeneic antitumor antibody. Many of the existing monoclonal antitumor antibodies are, indeed, specific for antigens which may not even be immunogenic in the tumor-bearing host (Hellstrom, K. E. and Hellstrom, I., 1985, in Monoclonal Antibodies for Tumour Detection and Drug Targeting, Baldwin, R. W. and Byers, V. S., eds., Academic Press, London, pp. 17–51), and can be used in this embodiment of the invention.

5.2.2. Internal Image Antibodies

Ab2 immunization can lead to Ab3 elicitation not only through specific V gene network interactions but also by virtue of internal-image mimicry (Urbain, J., et al., 1982, Ann. Immunol. 133D:179–189; Augustin, A., et al., 1983, Surv. Immunol. Res. 2:78). That is, when the anti-idiotype represents the conformational mirror-image of the antigen, it can substitute for nominal antigen and elicit an Ab1-like response (Nisonoff, A. and Lamoyi, E., 1981, Clin. Immunol. Immunopathol. 21:397) (FIG. 3). In a preferred embodiment, therefore, such anti-idiotypic antibodies can be used as immunogens for tumor therapy in IgH-mismatched hosts.

In an embodiment of the invention employing monoclonal anti-idiotypes, the appropriate Ab2 should be carefully selected. The experimental verification that any particular Ab2 is an internal image type of anti-idiotype hinges on its ability to mimic the conformational characteristics which define recognition of the antigen. Internal image anti-idiotypes compete in vitro with antigen for binding to idiotype-positive Ab1, and prime in vivo for Ab3 which mimic Ab1, and this priming occurs in a IgH unrestricted fashion (Nisonoff and Lamoyi, supra).

In addition to the inhibition of id+ binding to antigen, internal image Ab2 can substitute for antigen in terms of immune recognition. For example, Ab2 may stimulate antigen-specific clones in vitro in the absence of antigen, or Ab2+ cells may serve as a target for antigen-specific CTL (Ertl, H. C. J., et al., 1982, Proc. Natl. Acad. Sci. U.S.A. 79:7479). Since the Ab2 is substituting for antigen conformation, the Ab2 may be "presented" to T cells in these assays in the context of MHC molecules, and therefore the response can appear to be MHC restricted, just as for antigen-specific response (id.).

In an embodiment of the invention in which internal image immunogens are desired, xenogeneic anti-idiotypic antibodies may be used. It is possible that internal image immunogens fail to stimulate suppressor cells, while at the same time inducing $T_H$. This supposition is based on the notion, outlined in FIGS. 1D and 2C, that regulatory idiotypes which are represented by the expression of dominant V genes determine the communication between Ab2 and $T_S$, and that some anti-idiotypic antibodies may be selected which lack this particular idiotype yet retain the internal-image characteristics priming for $T_H$.

In a specific embodiment of the invention, internal image antibodies with tumor antigen activity can be used as tumor "vaccines" towards induction of specific tumor immunity. For example, such vaccines can be therapeutically valuable for patients whose primary neoplasms have been removed but who are at risk for development of metastases.

The ability of internal image Ab2 to compete with antigen for binding to AB1 (and vice versa) is an integral part of their behavior. However, Ab2 which do not function as internal images may still compete, due to steric hindrance (and perhaps other mechanisms as well). In a preferred aspect of the invention, one should investigate the ability of an Ab2 to induce an immune response over IgH (and MHC) barriers in experimental animals as part of their characterization as potential internal images.

Since, on occasion, the distinction between internal-image anti-Id and "true" anti-Id becomes blurred, anti-idiotypic antibodies which do not have internal image specificity may still display internal image-associated properties, which can be therapeutically valuable. For example, in our study of monoclonal anti-idiotypes raised against a murine bladder carcinoma antigen-associated monoclonal antibody, immunization with the anti-idiotypes elicited a vigorous Ab3 response which lacked any detectable antigen-binding (Lee, V. K., et al., Biochim. Biophys. Acta 865:127–139). The Ab3 raised against a particular anti-Id were apparently directed against "private" specificities associated with that anti-idiotype. Although the anti-idiotypic antibodies were shown to inhibit antigen binding by the Ab1, this was presumed due to steric inhibition, and we tentatively interpreted these data to mean that the Ab2 were not internal image antibodies. Surprisingly, however, these same monoclonal Ab2 were able to prime mice for antitumor responses and also to bind to tumor-specific T cell suppressor factors (Lee, V. K., et al., 1985, Proc. Natl. Acad. Sci. U.S.A. 82:6286–6290; Kuchroo, V. K., et al., 1987 Cellular Immunol. 104:105–114). Since the anti-idiotypic monoclonal antibodies in these experiments were raised in mice, and were directed against-xenogeneic antitumor monoclonal antibodies raised in rats, the antitumor response elicited in mice by Ab2 immunization would not be expected to be based on specific V gene selection, and could instead be attributed to some internal image Ab2.

A second example comes from experiments analyzing idiotypic responses to TMV-associated antigens, in which mice were immunized with rabbit anti-idiotypic antibodies which were specific for "private" rabbit idiotopes (Francotte, M. and Urbain, J. 1984, J. Exp. Med. 160:1485). Surprisingly, these mice made anti-TMV antibodies which were idiotypically cross-reactive with the rabbit idiotopes. Thus, while the stimulatory anti-idiotype was not an "internal image" specificity, it nevertheless elicited antigen-specific information in the face of apparent V gens incompatibility.

5.3. Production of Anti-Idiotypic Monoclonal Antibodies Specific to an Idiotype Which Recognizes a Defined Tumor Antigen

5.3.1. Production of Anti-Idiotypic Monoclonal Antibodies by Immunization With an Antibody (AB1) That Recognizes a Defined Tumor Antigen In a specific embodiment of the invention, production of anti-idiotypic monoclonal antibodies specific to an idiotype which recognizes a defined tumor antigen requires immunization of a host with antibodies that recognize the defined tumor antigen. As previously explained, such tumor antigens include but are not limited to oncofetal, or differentiation, antigens such as CEA, alpha-fetoprotein, the human antigenic functional equivalent of the 175 kDa murine antigen of transitional cell bladder carcinoma, melanoma associated antigen p97 (see Brown et al., 1981, J. Immunol. 127:539–546 and copending U.S. patent applications Ser. No. 827,313 filed Feb. 7, 1986, now abandoned, and Ser. No. 007,230 filed Jan. 27, 1987, now U.S. Pat. No. 5,262,177, which are incorporated by reference herein), differentiation antigens of human lung carcinoma such as L6 and L20 (see Hellstrom et al., 1986, Cancer Res. 46:3917–3923 and copending U.S. patent applications Ser. No. 834,172 filed Feb. 26, 1986, now U.S. Pat. No. 5,185,432, Ser. No. 776,321, filed Oct. 18, 1985, now U.S. Pat. No. 4,906,562, Ser. No. 684,759 filed Dec. 21, 1984, now U.S. Pat. No. 4,935,495, which are incorporated by reference herein), and the differentiation antigen associated with human melanoma, GD3 ganglioside antigen (see copending U.S. patent applications Ser. No. 831,684 filed Feb. 21, 1986, and Ser. No. 834,162 filed Feb. 20, 1986, now U.S. Pat. No. 5,055,559, which are incorporated by reference herein), antigens of fibrosarcoma, and the like.

The possible host species include but are not limited to experimental animals such as mice, rabbits, and chimpanzees; and humans. Various adjuvants can be used to enhance the immunological response to the antibodies, depending on the host species and including, but not limited to, mineral gels, e.g., aluminum hydroxide; surface active substances such as lysolecithin; pluronic polyols; polyanions; peptides; oil emulsions; and potentially useful human adjuvants such as BeG (bacille Calmette-Guerin) and corynebacterium parrum. The Ab2 can also be coupled to an immunogenic carrier, including but not limited to LPS, or cross-linked with glutaraldehyde (Primi, C. D., et al., 1982, J. Immunol. 129:1124–1129). The immunogen may also be incorporated into liposomes, or conjugated to polysaccharides and/or other polymers, or otherwise chemically modified for use. Allotypic determinants on the Ab2 molecule itself can also be used to enhance immunogenicity. In the reovirus system, when the immunization with Ab2 crossed allotypic barriers, that is, when the host was IgH mismatched, a vigorous Ab3 response was seen (Ertl, H., et al., 1986, supra). This result suggests that Ig allotypic determinants on the anti-idiotype acted as helper determinants towards augmenting the immune responses. Thus, in a particular embodiment, IgH mismatching may be used to enhance immunogenicity.

The anti-idiotypic antibodies, or fragments of the anti-idiotypic antibodies, or chemically modified fragments or antibodies may be used for immunization. In addition, a mAb fragment containing the idiotype of the mAb molecule could be used, including but not limited to the $F_v$, Fab, Fab', or $F(ab')_2$ fragments, which can be generated by known techniques.

The monoclonal antibody can be prepared by using any technique which provides for the production of antibody molecules by continuous cell lines in culture. These include but are not limited to the hybridoma technique originally described by Kohler and Milsrein (1975, Nature 256:495–497), and the more recent human B-cell hybridoma technique (Kozbor et al., 1983, Immunology Today 4:72) and EBV-transformation technique (Cole et al., 1985, Monoclonal Antibodies and Cancer Therapy, Alan R. Liss, Inc., pp. 77–96). Selection of the hybridoma can be carried out by any of numerous assays, e.g. for binding to Ab1, or for inhibition of AB1 binding to tumor cells (Nepom, G. T., et al., 1984, Proc. Natl. Acad. Sci. U.S.A. 81:2864–2867; Holbeck, S. L. and Nepom, G. T. 1983, J. Immunol. Methods 60:47–52; see Section 7.1.7, infra).

5.3.2.; Production of Anti-Idiotypic Monoclonal Antibodies Which Are Directed Against an Idiotope on T Cells That Recognizes a Defined Tumor Antigen In another specific embodiment of the invention, an anti-idiotypic antibody is produced, which is related to a tumor antigen, and which is directed against an idiotope associated with T cells that recognizes the tumor antigen. The idiotope may also be associated with suppressor factors that exhibit the idiotope directed against the tumor antigen. Such tumor antigens include but are not limited to those listed in Section 5.3.1, supra. In one embodiment (see Section 6, it Era), the anti-idiotypic antibody can be produced by immunization with tumor antigen, formation of hybridomas, and screening for auto-anti-idiotypic monoclonal antibodies by methods including but not limited to assay of tumor-specific DTH, tumor-specific LAI, binding to monoclonal antibody directed against the tumor antigen, etc. In particular embodiments, the tumor antigen used for production of auto-anti-idiotypic antibody can be specific to fibrosarcoma, transitional cell bladder carcinoma; it can be melanoma antigen p97 or GD3, or human lung carcinoma antigen L6 or L20. Alternatively, T cells ($T_H$ or $T_S$) or suppressor factors which bind tumor antigen can be used to immunize a host for the production of the anti-idiotypic antibody. In particular embodiments, T cells which express an idiotope defined by an antibody specific to fibrosarcoma, transitional cell bladder carcinoma, p97 melanoma antigen, GD3 melanoma antigen, L6 or L20 lung carcinoma antigen, may be used for immunization. Since injection of $T_S$ cells may be therapeutically detrimental, immunization with $T_H$ cells is preferred. The T cells used for immunization may be obtained, for example, from the tumor-carrying patient himself or from an appropriate (preferably histocompatible) donor whose immune system has been exposed to the tumor antigen. The T cells can then be isolated for injection by various techniques known in the art, e.g. fluorescencetagged monoclonal anti-tumor antibody binding and FACS. (See Section 6.4, infra). Suppressor factors for immunization can be isolated by many techniques known in the art, including but not limited to immunoaffinity chromatography (to a tumor-antigen coated column), generation of T—T hybridomas by fusing T cells from tumor-bearing hosts (Nelson, K. A., et al., 1980, Proc. Natl. Acad. Sci. U.S.A. 77:2866) followed by screening e.g. for suppression of DTH to tumor antigen, specific binding to tumor antigen, etc. (see Section 6.5, infra).

5.4. Evaluation and Demonstration of Immunopotency By Induction of Tumor-Specific CMI Where the anti-idiotypic antibody of the invention is envisioned for use in immunization against tumors (see Section 5.6.1, infra), in a preferred embodiment, the immunopotency of the antibody should be tested. Any method which can demonstrate immunopotency of the anti-idiotypic molecule by showing induction of tumor-specific CMI upon immunization with the anti-idiotypic antibody or its derivative fragment(s) is within the scope of the invention for evaluation of the immunopotency of the anti-idiotypic mAb; such assays include, but are not limited to DTH (for a description of the DTM assay procedure see Forstrom et al., 1983, Nature (London) 303:5627–529) and/or LAI (Halliday, W. J. & Maluish, A. E., 1982, in Assessment of Immune Status by the Leukocyte Adherence Inhibition Test, Academic, New York pp. 1–26; Koppi, T. A., and Halliday, W. J., 1982, Cell. Immunol. 66:394–406; Koppi, T. A., and Halliday, W. J., 1981, J. Natl. Cancer Inst. 66:1089–1096). Further specificity testing can include but is not limited to immunoabsorption assays and treatment of peritoneal cells with antibodies and complement.

5.5. Further Characterization of Anti-Iodiotypic Antibody

In order to further determine anti-idiotypic antibody specificity, AB1 binding assays and/or assays of inhibition of Ab1-tumor binding may be carried out. Such assays may be accomplished by any methods known in the art, e.g. those described in Section 7, infra. Two additional assays that may be done include tests of inhibition of complement dependent cytotoxicity or antibody dependent cellular cytotoxicity properties of AB1 (see Sections 7.1.1.3 and 7.1.1.4 infra).

5.6. Uses in Immunoprophylaxis, Immunotherapy, and Immunoassay

The purpose of this embodiment of the invention is to describe uses of the anti-idiotypic antibody molecules of this invention, or fragments of the antibody molecules, which may or may not be chemically modified, in the field of medicine.

5.6.1. Immunization Against Tumors

Patients having tumors may be treated therapeutically by immunization with the anti-idiotype monoclonal antibodies of the present invention whereas patients with a disposition for the tumor may be treated immunoprophylactically by such immunization. An advantage of using anti-idiotypic mAb over antigen in a tumor vaccine formulation is that large quantities of identical material can be obtained for use as immunogen. This is especially valuable when the antigen is a glycolipid or a carbohydrate, which itself may be difficult to obtain in pure form and in sufficient amounts. In addition, if the antigen is a protein, the availability of an anti-idiotypic antibody avoids the necessity of having the cloned gene for the antigen, in order to obtain sufficient quantities of the antigen for use in vaccines. The antiidiotypic antibodies, or fragments of the anti-idiotypic antibodies, or chemically modified fragments or antibodies may be used to immunize against tumors. Any mAb fragment containing the idiotype of the mAb molecule could be used, including but not limited to the $F_v$, Fab, Fab', or $F(ab')_2$ fragments, which can be generated by known techniques. The anti-idiotypic antibody molecule or its derivative fragments may be formulated with a suitable adjuvant in order to enhance the immunological response. These adjuvants may include, but are not limited to, mineral gels, e.g. aluminum hydroxide; surface active substances such as lysolecithin, pluronic polyols; polyanions; peptides; oil emulsions; and potentially useful human adjuvants such as BCG (bacille Calmette-Guerin) and corynebacterium parvum. The immunogen may also be incorporated into liposomes, or conjugated to polysaccharides and/or other polymers, or otherwise chemically modified for use.

Many methods may be used to introduce the immunizing formulations; these include but are not limited to intradermal, intramuscular, intraperitoneal, intravenous, subcutaneous, and intranasal routes.

In particular embodiments of the invention, hosts with fibrosarcoma can be injected intraperitoneally with an antiidiotypic monoclonal antibody specific to an idiotope which recognizes a fibrosarcoma antigen.

Immunization in test animals may be assayed by injection of the anti-idiotypic antibody or related derivative molecule, followed by challenge with a tumori-genic agent(s) such as syngeneic tumor cells or chemical carcinogens, and observing tumor development and progression.

5.6.2. Adoptive Immunotherapy

In another embodiment of the invention, T cells (preferably $T_H$) which express an idiotope which recognizes a tumor antigen which can be, but is not limited to, an antigen described in Section 5.3.1, supra, can be introduced into a host, for immunoprophylaxis or immunotherapy. Such cells can be obtained from the tumor-growing host himself, expanded in vitro, selected for the proper idiotypic specificity (either before or after expansion), and reintroduced into the host (see Section 6.4, infra). Alternatively, the T cells can be obtained from an appropriate (preferably histocompatible) donor.

In an alternative approach, it is possible to activate tumor-specific lymphocytes in vitro and to treat the patient with the activated tumor-specific leukocytes. Recently, regression of cancer was observed in response to an adoptive immunotherapeutic treatment involving the administration of lymphokine activated killer cells (LAK) to tumor-bearing hosts (Rosenberg et al., 1985, New Engl. J. Medicine 313:1485–1492). However, this therapy resulted in a number of undesirable side effects, including severe toxicity, pulmonary edema, and respiratory distress. By contrast, the method of this embodiment of the present invention involves administering to a patient stimulated lymphocytes which are specific for the tumor associated antigen (which can be, but is not limited to, an antigen described in Section 5.3.1, supra.) which may result in a more specific therapy and reduced side effects. This can be accomplished, for example, by a modification of the methods described in copending application Ser. No. 909,447, filed Sep. 19, 1986, by Hu and Zarling, entitled "Methods of Adoptive Immunotherapy for Treatment of AIDS," which is incorporated by reference herein. Peripheral lymphocytes can be withdrawn from the patient, or a histocompatible donor who was exposed either to the tumor antigen or to a monoclonal anti-idiotypic antibody raised to the idiotype of an antibody that defines the tumor antigen as described above. The lymphocytes can then be stimulated in vitro in the presence of the tumor-specific anti-idiotypic antibodies of the present invention. Such specific stimulation can be accomplished using the monoclonal anti-idiotypic antibodies of the present invention in a method such as the one described by Binz et al. (1982, Int. J. Cancer 29:417–423), or described in copending application Ser. No. 909,447, filed Sep. 19, 1986. The activated T cells can then be expanded in cell culture. This expansion can be accomplished by repeated stimulation of the T cells with the anti-idiotypic antibodies of the invention, with or without IL-2, or by growth in medium containing IL-2 alone. Other methods of T cell cultivation (for example, with other lymphokines, growth factors, or other bioactive molecules) can also be used. The activated lymphocytes may then be tested for cell-mediated antitumor immune reactivity. If desired, confirmation of identity of the activated lymphocytes as T cells can be accomplished by examination of the cells with regard to cell-surface expression of T and B cell markers. This can be carried out, for example, by immunofluorescence analysis using fluorescein-conjugated monoclonal antibodies to T and B cell antigens. Expression of known T cell markers, such as the CD4 and CD8 antigens, confirms the identity of the activated lymphocytes as T cells.

The activated T cells are then tested for antitumor reactivity. This can be accomplished by any of several techniques known in the art for assaying specific cell-mediated immunity. For example, a cytotoxicity assay, which measures the ability of the stimulated T cells to kill the tumor cells in vitro, may be accomplished by incubating the lymphocytes with $^{51}$Cr-labelled tumor cells, and uninfected labelled cells, and measuring $^{51}$Cr release upon lysis. Such assays have been described (see, for example, Zarling, J. M., et al., 1986, J. Immunol. 136:4669). The activated lymphocytes can also be tested for T helper cell activity by measuring their ability to proliferate, as shown by $^3$H-thymidine incorporation, following stimulation, and/or by measuring their ability to produce lymphokines such as IL-2 or interferon upon stimulation, in the absence of exogenous IL-2 (see copending application Ser. No. 909,447, filed Sep. 19, 1986, now abandoned). Other assays of specific cell-mediated immunity known in the art, such as leukocyte-adherence inhibition assays (Thomson, D. M. P. (ed.), 1982, Assessment of Immune Status by the Leukocyte Adherence Inhibition Test, Academic Press, New York), may also be used. The selected lymphocytes can then be inoculated into the patient. Inoculation of the activated T cells is preferably through systemic administration although other methods of administration (for example, direct infusion into an artery) can be used. The T cells can be administered intravenously through a central venous catheter or into a large peripheral vein. In a preferred embodiment, approximately $1 \times 10^8$ cells are infused initially and the remainder are infused over the following several hours. In some patients, recombinant human IL-2 may be used and can be infused intravenously every 8 hours beginning at the time of T cell infusion. Injections of IL-2 will preferably be at doses of 10,000 to 100,000 units/kg bodyweight, as previously used in cancer patients (Rosenberg, S. A., et al., 1985, N. Engl. J. Med. 313:1485). The IL-2 infusion can be continued for several days after infusion of the activated T cells if tolerated by the patient.

5.6.3. Inhibition of Immune Suppression of Anti-Tumor Reactivity

In another embodiment of the invention, anti-idiotypic antibodies which specifically recognize an idiotope which is directed against a tumor antigen and which idiotope is present on suppressor T cells and/or suppressor factors, can be administered in vivo in order to inhibit suppression of anti-tumor reactivity. In particular embodiments, such a tumor antigen can include but is not limited to those listed in Section 5.3.1, supra.

5.6.4. Immunoaffinity Application

The anti-idiotypic antibodies or related molecules of this invention may be used to isolate antibodies directed against a defined tumor antigen. Techniques known in the art by which this could be accomplished include but are not limited to immunoaffinity columns and immunoabsorption reactions. Anti-tumor antibody isolated through use of the anti-idiotypic antibody or related molecules could be a valuable tool in tumor immunotherapy.

5.6.5. Immunoassays

In an alternate embodiment of the present invention, the anti-idiotypic antibodies or related molecules of the present invention may be used as antigens in immunoassays. These immunoassays would allow the detection of anti-tumor antibody in animals or patients. The molecules of the present invention would also be used in competition immunoassays to test for the presence of tumor antigens.

The molecules of the present invention may be used in any immunoassay system known in the art, including but not limited to radioimmunoassays, ELISAs, "sandwich" assays, precipitin reactions, gel diffusion precipitin reactions, immunodiffusion assays, agglutination assays, complement-fixation assays, protein A immunoassays, fluorescent immunoassays, and immunoradiometric assays.

In a specific embodiment, the anti-idiotypic antibodies of the invention, directed against an idiotype of "Antibody 1" which defines a tumor antigen, can be used in competitive immunoassays to monitor the presence of antibodies in patients being administered Antibody 1, for therapeutic or diagnostic purposes (see Sections 7.1.1.5, 7.2.5., infra). In another embodiment, anti-idiotypic antibodies can be used to identify anti-tumor antibodies during purification procedures.

6. IMMUNOTHERAPY OF MURINE SARCOMAS WITH AUTO-ANTI-IDIOTYPIC MURINE SARCOMAS WITH WHICH BIND TO TUMOR-SPECIFIC T CELLS

According to the network theory (Jerne, N. K., 1974, Ann. Immunol. 125C:373; Rajewski, K. and Takemori, T., 1983, Ann. Rev. Immunol. 1:569; Urbain, J., et al., 1982, Ann. Immunol. 133D:179), mice forming an immune response to syngeneic satcomas should have antibodies to the idiotypes of the responding lymphocytes. As described in the examples infra, based on this prediction, we immunized BALB/c mice to either of two syngeneic, transplanted fibrosarcomas, and formed hybridomas which produced monoclonal antibodies which primed syngeneic mice for tumor-specific DTH. One of these auto-anti-idiotypic monoclonal antibodies is shown to define an idiotope present both on T cells which have antitumor activity and on products of T suppressor cells, which inhibit this activity. We also show that treatment of mice with either of the two monoclonal anti-idiotypic antibodies significantly reduced growth of established satcomas, an effect that was specific for the appropriate mAb-tumor combination.

6.1. Materials and Methods

6.1.1. Mice

BALB/c mice were bred in the Division of Animal Health Resources, Fred Hutchinson Cancer Research Center (FHCRC), Seattle, Wash., and were matched for age and sex in each experiment. Females older than ten weeks were chosen since they gave optimal responses in pilot tests. CB-20 mice were raised at FHCRC from breeding pairs obtained from Dr. Michael Potter, National Institute of Health.

6.1.2. Tumors

Fibrosarcomas MCA-1490, MCA-1510, and MCA-1511 were induced in BALB/c mice by intramuscular injection of 3-methylcholanthrene in trioctanoin and maintained by serial syngeneic transplantation of tissue frozen in the second generation. They were shown to be free of LDH, Sendai and ectromelia viruses, and from mycoplasma, and, like other chemically induced mouse satcomas, to express individually unique tumor-specific transplantation antigens. BW5147.G.1.4.oua$^r$.1, is a drug-marked AKR thymoma which was obtained from the Cell Distribution Center of the Salk Institute. NS1 cells came from Dr. Ingegerd Hellstrom's laboratory. Both BW5147 and NS1 cells were shown to be free of mycoplasma.

6.13. Assay of Delayed-Type Hypersensitivity

An assay was used which measured delayed-type hypersensitivity (DTH) as mediated by Thy $1^+$, Lyt $1^+$ lymphocytes, and was characterized by the typical morphological manifestations of a DTH reaction (Forstrom, J. W., et al., 1983, Nature 303:627; Cory, J., et al., 1981, in Monoclonal Antibodies and T Cell Hybridomas, Hammerling, G. J., et al., eds., Elsevier/North-Holland Biomedical Press, p. 503). Mice were immunized by subcutaneous injection of either a total of $1 \times 10^6$ irradiated (15,000 rad) tumor cells into two sites, one on each flank, or by injection of 3–10 ug of mAb (diluted in phosphate-buffered saline, PBS) at four subcutaneous sites. When material was assayed for suppression of DTH, it was always assayed for suppression of its inductive phase. In these experiments, the putative suppresslye material was diluted to 100 ul in PBS and injected into a tail vein immediately following immunization.

In each test for DTH, treatment or control groups consisted of 5 mice, and they were always coded. Five days after immunization, DTH was elicited by injection of $5 \times 10^5$ tumor cells into one of the two hind footpads. After 24 hours, the thickness of both the injected and the uninjected contralateral footpads was measured, using a dial micrometer. For each treatment group, the data are presented as the mean increase in thickness (i.e., the swelling) of the injected footpads. The significance of the differences between treatment groups and corresponding controls was determined using a two-tailed Student's t test.

6.1.4. Generation of Auto-Anti-Idiotypic Monoclonal Antibodies

BALB/c mice were immunized by subcutaneous injection of $1 \times 10^7$ trypan blue unstained, cultured MCA-1490 or MCA-1511 cells, followed three weeks later by excision of the resulting tumor nodules. After two more weeks, the mice were injected with $2 \times 10^6$ irradiated (15,000 rads) cells from the respective tumors, and two weeks later they were injected once more with the same dose. Splenic cells were obtained 7 days after the last injection and fused to NS-1 myeloma cells, using techniques which have been described (Yeh, M. Y., et al., 1979, Proc. Natl. Acad. Sci. U.S.A. 76:2927).

Hybridomas were first screened for production of IgG antibodies using a radioimmunocompetition assay (Brown, J. P., et al., 1980, J. Biol. Chem. 255:4980), and those producing greater than 4 µg IgG per ml were expanded. Culture supernatants were pooled, with each pool consisting of supernatants from five hybridomas. Antibodies were purified from each pool by affinity chromatography on *S. aureus* protein A covalently coupled to Sepharose CL-4B (Sigma Chemical Co., St. Louis, Mo.) (Brown, J. P., et al., 1980, J. Biol. Chem. 255:4980). The pH of the antibody solutions was adjusted to 8.5 prior to chromatography to facilitate the isolation of $IgG_1$. BALB/c mice were immunized by injection with the pooled antibodies and five days later were challenged with the appropriate tumor cells (MCA-1490 or MCA-1511 cells) for elicitation of DTH. The individual supernatants of a pool testing positive were assayed for the priming of DTH to MCA-1490 and. MCA-1511, with one of the two tumors serving as the control. Two to four percent of the wells from each fusion were found to contain antibodies with the desired activity. Hybridomas making antibodies that primed for tumor-specific DTH were cloned twice by limiting dilution, after which positive clones were expanded and adapted to grow as ascites tumors in pristane-primed BALB/c mice (Yeh, M. Y., et al., 1979, Proc. Natl. Acad. Sci. U.S.A. 76:2927). Monoclonal antibodies were purified from ascites fluid by affinity chromatography on protein A Sepharose. mAb 4.72 (relating to MCA-1490) and mAb 5.96 (relating to MCA-1511) were used for the present study. They were both of the IgG1 isotype, as was mAb 8.2, which was used as a control in some experiments.

6.1.5. T Cell Hybridomas

Several hybridoma lines were obtained by fusion of BW5147 cells with thymocytes of mice carrying MCA-1490 tumors, as previously described (Nelson, K. A., et al., 1980, Proc. Natl. Acad. Sci. U.S.A. 77:2866; Nelson, K., et al., 1985, in T-Cell Hybridomas, Taussig, M. J., ed., CRC Press, p. 129). The four hybridomas used in this study produced factors which suppressed the lysis of MCA-1490 cells by specifically immune T cells as tested in a $^{51}$Cr-release assay (Nelson, K., et al., 1985, supra). Cultures of these hybridomas and of the BW5147 fusion partner were grown in Dulbecco's modified Eagles' medium (Grand Island Biological Co., Grand Island, N.Y.), which was supplemented with fetal bovine serum (150 µl/ml), penicillin (100 units/ml), streptomycin (100 µg/ml) and L-glutamine (290 µg/ml), and was buffered with sodium bicarbonate. Spent medium was taken from cells in log phase growth when there were approximately $2 \times 10^6$ cells per ml. The medium was filtered (0.4 microns, Millipore) and stored at −70° C. until assayed.

6.1.6. Isolation of Suppressor Factors By Affinity Chromatography With mAb mAb 4.72 or 5.96 was used together with a control mAb, 8.2, which is also of the IgG1 isotype and is specific for a human melanoma antigen, p97 (Brown, J. P., et al., 1981, J. Immunol. 127:539). The mAb were diluted in PBS to 2 mg per ml and then coupled to an equal volume of Affi-Gel 10 (Bio-Rad Laboratories, Richmond, Calif.) by overnight incubation at 4° C. The gels were washed, incubated with 0.1M ethanolamine and used to prepare columns. The columns were washed extensively with PBS and pre-eluted with 3M NaSCN prior to use. Spent culture media of T cell hybridomas (as a source of suppressor factor) or BW5147 cells (as a control) were diluted 1:10 in PBS, after which 0.2 ml of the diluted media were passed through columns of 0.2 ml of gel. The columns were washed with PBS until 2 ml of effluent had been collected, after which the effluents were diluted 1:10 in PBS and assayed for suppression of the inductive phase of DTH.

Experiments were also performed with sera from BALB/c mice which had been transplanted with either MCA-1490 or MCA-1511 tumors or which were untreated littermates. The sera were diluted 1:10 in PBS, after which 0.5 ml of the diluted sera was passed through columns of 0.5 ml gel. The columns were washed with PBS. The first 1.5 ml was collected as effluent and an additional 5 ml was discarded. Bound proteins were then eluted from the columns by addition of 0.5 ml of 3M NaSCN, and the eluates were desalted by passage through columns of Sephadex G-25 equilibrated with PBS. Eluates and effluents were diluted in PBS to yield a 1:100 dilution relative to the original sera. They were subsequently tested for suppression of the inductive phase of DTH.

6.1.7. Binding of Suppressor Factor K54SF to MCA-1490 Cells

Adherent cultured MCA-1490 cells were incubated in ethylene-diamine tetraacetic acid (5 mM), washed with PBS, and incubated in a 0.1% solution of glutaraldehyde for 10 minutes at 4° C. The cells were subsequently incubated in PBS with 0.5% bovine serum albumin, followed by washing with PBS. Spent culture media of T hybridoma I-K54 or control BW5147 cells were diluted 1:100 in PBS containing 10 ug of either mAb 4.72 or mAb 8.2 (as a control), and incubated on ice for 30 minutes. Subsequently, they were added to 100 ul of packed tumor cells, which were suspended and incubated at room temperature for 10 minutes and on ice for an additional 30 minutes. In one experiment, the tumor cells were pretreated by incubation with antibody and washed three times with PBS before the addition of diluted spent media from I-K54 or BW5147 cells. After incubation on ice, the tumor cells were washed 5 times with 15 ml of PBS and suspended in 0.5 ml of glycine-HCl buffer (pH 3.0). After further incubation on ice for 10 minutes, the cells were pelleted by centrifugation at 200 × g. The pH of the supernatant was immediately adjusted by passage through Sephadex G-25 equilibrated with PBS. The eluates were diluted 1:10 in PBS and assayed for suppression of the inductive phase of DTH.

6.1.8. Isolation and Culture of T Cells Lines

T cells reacting with mAb 4.72 were obtained from lymph nodes draining the site of a progressively growing, transplanted MCA-1490 sarcoma. The cells were isolated by centrifugation on a Percoll gradient (Pharmacia) and mixed with mAb 4.72 or mAb 8.2 coupled with biotin. Subsequently, they were washed, treated with avidin-fluorescein isothiocyanate (FITC), washed again and analyzed on a fluorescence-activated cell sorter (FACS-II, Becton-Dickinson). Brightly stained cells, which were seen only in the sample treated with mAb 4.72, and which represented less than 1% of the sample, were collected. These cells, termed 90.3, were cultured in Click's medium supplemented with 25% medium from a culture of rat spleen cells which had been stimulated with concanavalin A for 24 hours. Vigorous growth was observed after 25 days and was maintained by expanding the cultures into fresh medium every 72 hours. Another cell line, 11.2, was established from Lyt-1 positive lymphocytes which had been obtained from nodes draining the site of a MCA-1511 tumor; it was maintained in a way similar to line 90.3. The cells were assayed between 6 and 18 weeks after establishment of the 90.3 or 11.2 lines. Normal T cells from lymph nodes of tumor-free mice were cultured for 48 hours before they were used as controls for some of the assays.

6.1.9. In Vivo Manipulation of Tumor Growth

Tumor tissue was obtained from mice 14–21 days after injection of tumor cells from serial passage. A suspension was prepared by mechanical disruption and brief treatment with trypsin. Viability was assessed by exclusion of trypan blue. In the experiment presented in FIG. 4, tumor cells were mixed with cultured T cells at a ratio of 1:10 and the mixture injected in one subcutaneous site. Ten mice were used per treatment group. Tumor growth was monitored at 2–4 day intervals by two perpendicular measurements of the growing tumor nodule. Tumors with an area greater than 0.2 $cm^2$ rarely regressed in untreated controls and were considered established tumors.

In the experiments measuring the effect of mAb treatment, tumor cells were injected subcutaneously in one site per mouse. mAb was diluted in PBS and injected intraperitoneally (i.p.), 10 ug per injection. Tumor growth was monitored as described above. A two-tailed Student's t test was used to determine the significance of the difference between the various treatment groups.

6.2. Subcutaneous Administration of mAb 4.72 or mAb5.96 Induces Tumor-Specific DTH to MCA-1490 and MCA-1511

We have previously reported that mAb 4.72 can induce DTH to MCA-1490, when injected subcutaneously, and that it reacts with an idiotope on tumor-specific cells, i.e., that it is auto-anti-idiotopic (Forstrom, J. W., et al., 1983, Nature 303:627). We have now developed a similar mAb, 5.96, using lymphocytes from mice sensitized to an antigenically different sarcoma, MCA-1511 (id.) This allowed us to assess the immunological specificity of the DTH effect by testing mAb 4.72 and 5.96 in parallel (Table I).

TABLE I mAbs 4.72 AND 5.96 PRIME BALB/C MICE FOR DTH
THAT IS TUMOR-SPECIFIC AND ALLOTYPE
RESTRICTED*

| Mouse Strain | Mice Injected with | Mean Footpad Swelling (× $10^{-3}$ in ± SE) in Mice Challenged with | |
|---|---|---|---|
| | | MCA-1490 | MCA-1511 |
| BALB/c ($H-2^d$, $Igh-1^a$) | mAb 4.72 | 15.3 ± 1.2† | 5.0 ± 1.6 |
| | MCA-1490 cells | 18.4 ± 1.6† | Not done |
| | mAb 5.96 | 8.0 ± 1.2 | 13.7 ± 0.3† |
| | MCA-1511 cells | Not done | 18.7 ± 0.9† |
| | Diluent | 8.3 ± 1.2 | 5.6 ± 1.8 |
| CB-20 ($H-2^d$, $Igh-1^b$) | mAb 4.72 | 7.7 ± 0.4 | 6.7 ± 0.3 |
| | MCA-1490 cells | 18.3 ± 0.9† | Not done |
| | mAb 5.96 | 8.2 ± 0.6 | 6.7 ± 1.2 |
| | MCA-1511 cells | Not done | 20.0 ± 1.8† |
| | Diluent | 8.0 ± 1.2 | 5.3 ± 0.6 |

*Five mice in each group were injected subcutaneously with 5 ug of mAb or $10^6$ tumor cells in 100 ul. Five days later, all mice were given 5 × $10^5$ tumor cells in 20 ul into one hind footpad. The increase in the thickness (swelling) of the injected pad over the contralateral pad was determined 24 hours later and is presented as the mean (± SE) for each group.
†The response of these mice was significantly greater than that of mice injected with diluent at P less than 0.01 by Student's t test.

As shown in Table I, BALB/c mice primed with mAb 4.72 responded with DTH to a subsequent challenge with MCA-1490 cells but not to challenge with MCA-1511 cells. mAb 5.96 behaved in an analogous way in that it primed BALB/c mice for DTH to MCA-1511 but not MCA-1490. The specificity of the DTH indicates that different idiotopes were involved in the immune responses to MCA-1490 and MCA-1511.

In agreement with previous data for mAb 4.72 (Forstrom, J. W., et al., 1983, Nature 303:627), the priming required identity at genes linked to the Igh-1 allotype locus (Table I), since neither of the two mAb primed CB-20 mice. Immunization with tumor cells did induce DTH in the CB-20 mice. When tested with antibody binding assays (Cory, J., et al., 1981, in Monoclonal Antibodies and T Cell Hybridomas, Hammerling, G. J., et al., eds., Elsevier/North-Holland Biomedical Press, p. 503), mAb 5.96 was similar to mAb 4.72 (Forstrom, J. W., et al., 1983, Nature 303:627) in that it did not bind to sarcoma cells.

We conclude that mAb 4.72 and mAb 5.96 are functionally anti-idiotopic to the immune responses to MCA-1490 and MCA-1511, respectively.

6.3. Intravenous Administration of mAb 4.72 Suppresses DTH to MCA-1490

We tested the effect of intravenous (i.v.) administration of mAb 4.72 on the DTH reactivity of mice which had been immunized by subcutaneous injection of either mAb 4.72 or MCA-1490 cells or with MCA-1511 cells, the latter being used as control. Immediately following the subcutaneous immunization, mice were injected via a tail vein with approximately 5 ug of mAb 4.72 or mAb 8.2 (as a control). The DTH response was measured 5 days later (Table II).

TABLE II mAb 4.72 SUPPRESSES DTH TO MCA-1490 WHEN INJECTED INTRAVENOUSLY (I.V.) INTO MICE IMMEDIATELY AFTER IMMUNIZATION BY SUBCUTANEOUS INJECTION OF EITHER mAb 4.72 OR MCA-1490 TUMOR CELLS*

| Mice Immunized with | Mice Challenged with | Antibody (or Fab fragments) Injected i.v. | Mean Footpad Swelling ($\times 10^{-3}$ in. $\pm$ SE) |
|---|---|---|---|
| mAb 4.72 | MCA-1490 | mAb 4.72 | 4.8 ± 0.8† |
|  |  | mAb 8.2 | 12.2 ± 0.7 |
|  |  | None (diluent) | 13.6 ± 0.5 |
| MCA-1490 | MCA-1490 | mAb 4.72 | 6.8 ± 1.6† |
|  |  | Fab 4.72 | 7.2 ± 1.3† |
|  |  | mAb 8.2 | 17.0 ± 1.3 |
|  |  | None (diluent) | 19.8 ± 0.7 |
| Nothing | MCA-1490 | None | 4.0 ± 0.9 |
| MCA-1511 | MCA-1511 | mAb 4.72 | 15.0 ± 2.6 |
|  |  | Fab 4.72 | 15.6 ± 1.2 |
|  |  | mAb 8.2 | 14.8 ± 2.1 |
|  |  | None (diluent) | 16.4 ± 2.6 |
| Nothing | MCA-1511 | None | 4.6 ± 1.3 |

*Mice were immunized by subcutaneous injection, and DTH was measured as described for Table I. Material assayed for suppression of DTH was diluted, and 100 ul injected i.v. immediately following immunization. Each mouse received 5 ug of whole mAb or 3.5 ug of Fab fragments.
†The response of these mice was significantly lower than that of mice receeiving diluent at P less than 0.001 according to Student's t test.

As shown in Table II, i.v. injection of mAb 4.72 suppressed the ability of subcutaneously injected mAb 4.72 or MCA-1490 cells to prime mice for DTH to MCA-1490. Furthermore, i.v. injection of Fab fragments prepared from mAb 4.72 suppressed immunization with MCA-1490 cells. Immmunization with MCA-1511 cells was not suppressed, and i.v. injection of a control mAb, 8.2, had no effect.

We conclude that the route of administration influenced the DTH reactivity of mice receiving mAb 4.72, with subcutaneous injection inducing DTH (see Section 6.2., supra) and i.v. injection suppressing this effect.

6.4. Expression of an Idiotope Defined by mAb 4.72 on T Cells Mediating DTH to MCA-1490

We studied whether the mAb 4.72 defined idiotype was present on T cells mediating DTH to MCA-1490. Mononuclear cells from lymph nodes draining a growing MCA-1490 tumor were analyzed on a fluorescence-activated cell sorter (FACS) using mAb 4.72 coupled to biotin and avidin-FITC. Brightly stained cells were observed. Although the brightly stained cells represented less than one percent of the total population of mononuclear cells, they were not seen in samples analyzed with a biotinylated control monoclonal antibody, mAb 8.2, used at the same dose. The stained cells were isolated and cultured in the presence of interleukin-2 (IL-2), from which a cell line was established, which was called 90.3. When the 90.3 cells were analyzed for surface phenotype after six weeks of culture, they bound mAb 4.72, although the fluorescence intensity was lower than that of the original cells. These cells were Thy-1 positive and expressed Lyt-1 but not Lyt-2 antigens.

We then investigated the effect of the 90.3 cells on the DTH response to MCA-1490 (Table III).

TABLE III

TUMOR-SPECIFIC DTH IS TRANSFERRED BY T CELLS FROM LINES 90.3 AND 11.2*

| Mice Injected with Mixture of | | Mean Footpad Swelling ($\times 10^{-3}$ in. $\pm$ SE) | |
|---|---|---|---|
| Tumor Cells | Effector Cells | Experiment 1 | Experiment 2 |
| MCA-1490 | 90.3 | 19.2 ± 1.6† | 15.0 ± 2.2† |
| MCA-1490 | Normal T | 9.6 ± 1.1 | 4.8 ± 0.6 |
| MCA-1490 | None (diluent) | 7.0 ± 0.7 | 4.0 ± 0.4 |
| MCA-1511 | 90.3 | 9.4 ± 1.0 | 4.0 ± 0.4 |
| MCA-1511 | 11.2 | 17.3 ± 2.6 | 10.7 ± 1.2† |
| MCA-1511 | Normal T | 10.2 ± 2.3 | 3.0 ± 0.3 |
| MCA-1511 | None (diluent) | 8.0 ± 0.7 | 3.0 ± 0.4 |
| None (diluent) | 90.3 | 0.4 ± 1.2 | 0.2 ± 0.4 |
| None (diluent) | 11.2 | 2.6 ± 0.6 | 1.2 ± 0.6 |
| None (diluent) | Normal T | 4.8 ± 1.0 | 3.6 ± 1.2 |

*Effector T cells ($2 \times 10^5$) derived from lines 90.3 or 11.2 or from naive BALB/c mice were mixed with MCA-1490 or MCA-1511 cells ($5 \times 10^5$) and injected into one footpad of a naive BALB/c mouse. Five mice were used per group. After 24 hours, DTH was measured and calculated as described in Table I.
†The response of these mice was significantly greater than that of mice receiving diluent and MCA-1490 cells at P less than 0.02 by Student's t test.

As shown in Table III, there was DTH to MCA-1490 when mixtures of 90.3 cells and MCA-1490 cells were injected into the footpads of naive BALB/c mice. There was no DTH to MCA-1511, and neither was there any footpad swelling in mice which received only the 90.3 cells but no MCA-1490 cells. A second line of T cells, 11.2, was established from lymph nodes of mice draining the antigenically different sarcoma MCA-1511. The 11.2 line gave DTH to MCA-1511 but not to MCA-1490. Lymph node cells from naive mice were cultured in medium containing IL-2 for 48 hours prior to the assays and was used as another control; they did not transfer DTH to MCA-1490.

90.3 cells, which had been cultured for nine weeks, were tested for their effect on the in vivo growth of the MCA-1490 tumor. Cultured T cells from naive mice were used as controls. The T cells were mixed with MCA-1490, MCA-1510 or MCA-1511 tumor cells; each mixture was injected subcutaneously into ten naive BALB/c mice. Time to appearance of tumors was monitored, as well as the growth rate of the tumors. As shown in. FIG. 4, one of ten mice which had received a mixture of MCA-1490 together with 90.3 cells developed palpable tumors, as compared to nine of ten mice in which control T cells rather than 90.3 cells were admixed. The 90.3 cells had no effect on two antigenically different sarcomas, MCA-1510 or MCA-1511.

We conclude that mAb 4.72 reacted with a small population of T cells from mice bearing sarcoma MCA-1490, and that cell line 90.3, which was derived from such cells, was specifically reactive to MCA-1490.

6.5. Expression of an Idiotope Recognized by mAb 4.72 on Factors Derived From Suppressor T Cells We have previously described the generation of T—T hybridomas by fusing T cells from mice bearing sarcoma MCA-1490 (Nelson, K. A., et al., 1980, Proc. Natl. Acad. Sci. U.S.A. 77:2866). The monoclonal products (suppressor factors) made by four of these hybridomas, I-K54, II-15, II-32, and II-122, have been demonstrated to suppress DTH to MCA-1490, but not to MCA-1511, and to bind specifically to MCA-1490 cells, while they differed as to the kinetics and genetic restriction of their suppression (Nelson, K., et al., 1985, in T-Cell Hybridomas, Taussig, M. J., ed., CRC Press, p. 129).

We selected one of the four suppressor factors, K54SF, to test whether the idiotope defined by mAb 4.72 was associated with the portion of that factor which could bind to MCA-1490. K54SF (obtained from supernatant of cultured I-K54 cells) and MCA-1490 eels were inoculated together, after which the tumor cells were washed and any K54SF that had bound to them was eluted. Suppression was assayed by DTH tests after injecting the eluates i.v. into mice immediately after these had been immunized subcutaneously with MCA-1490 or MCA-1511 cells. Tumor-specific suppressive activity was recovered in the eluates.

The ability of mAb 4.72 to inhibit the binding of K54SF to MCA-1490 was investigated in more detail. Medium containing K54SF was mixed with either mAb 4.72 or mAb 8.2 (control) before it was added to MCA-1490 cells, and eluates of the cells were tested for suppression (Table IV).

TABLE IV

INCUBATION OF K54SF (A SUPPRESSOR FACTOR MADE BY T—T HYBRIDOMA I-K54) WITH mAb 4.72 INHIBITS ITS BINDING TO MCA-1490 CELLS*

Anti-MCA-1490 Immune Mice Injected with

| Source of Suppressor | Suppressor Factor First Mixed with | Subsequently Incubated with and Eluted from | Mean Footpad Swelling (× 10⁻³ in. ± SE) in Mice Challenged with MCA-1490 | |
|---|---|---|---|---|
| Factor (medium) | | | Experiment 1 | Experiment 2 |
| I-K54 | mAb 8.2 | MCA-1490 | 6.4 ± 0.6† | 4.0 ± 0.7† |
| I-K54 | mAb 4.72 | MCA-1490 | 15.6 ± 1.1 | 15.2 ± 0.9 |
| BW5147 (control) | mAb 8.2 | MCA-1490 | 17.4 ± 0.9 | Not done |
| BW5147 (control) | mAb 4.72 | MCA-1490 | 17.2 ± 1.6 | Not done |
| I-K54 | Diluent | MCA-1490 pre-incubated with mAb 8.2 | Not done | 6.6 ± 1.5† |
| I-K54 | Diluent | MCA-1490 pre-incubated with mAb 4.72 | Not done | 17.6 ± 1.2† |

*Media of I-K54 or BW5147 (control) cells were first mixed with mAb 4.72 or mAb 8.2, after which they were incubated with MCA-1490 cells. In Experiment 2, there were also groups (lines 5 and 6 in the Table) in which MCA-1490 cells were incubated with mAb 8.2 or mAb 4.72, before they were incubated with I-K54 medium. After incubation, the tumor cells were washed, and material bound to them was eluted and assayed for suppression of DTH to MCA-1490. Mean footpad swelling in unimmunized (control) mice was 5.0 ± 0.3 in Experiment 1 and 5.2 ± 0.6 in Experiment 2, and mean footpad swelling in anti-MCA-1490 immune mice challenged with MCA-1490 was 15.8 ± 1.4 in Experiment 1 and 17.6 ± 1.0 in Experiment 2.
†The response of these mice was significantly lower than that of mice receiving diluent at P less than 0.001 by Student's t test.

As shown in Table IV, eluates of MCA-1490 cells which had been incubated with a mixture of mAb 8.2 and KS4SF, suppressed DTH to MCA-1490. In contrast, eluates of MCA-1490 cells incubated with a mixture of K54SF and mAb 4.72 were not suppresslye. This result indicates that the ability of K54SF to bind to MCA-1490 was inhibited by its binding to mAb 4.72. Eluates of MCA-1490 cells which had been incubated with BW5147 (control) medium and mAb 8.2 were not suppressive; thus suppression was not due to eluted tumor antigen. Pretreatment of MCA-1490 cells with mAb 4.72 did not prevent them from binding K54SF (see line 6 of Table XV), and thus the inhibition seen when K54SF was incubated with mAb 4.72 was not due to competition between mAb 4.72 and K54SF for binding to antigen on MCA-1490 cells. The results suggest that the idiotope recognized by mAb 4.72 is expressed at the site of K54SF which binds to MCA-1490 or, at least, in close proximity to that site. Similar results were obtained for the suppressor factor produced by a T cell hybridoma, II-32.

Since K54SF suppresses DTH to MCA-1490, we assayed the effect of K54SF on the function of 90.3 cells, since these cells could transfer DTH specific to MCA-1490 (see Section 6.4, supra). Mice were injected, in one footpad, with a mixture of cells from the 90.3 line and cells from the MCA1490 tumor. One hour later, K54SF (as supernatant of the I-K54 hybridoma) was injected into the same footpad; BW5147 supernatant was used as control. As shown in Table V, injection of K54SF suppressed the ability of the90.3 cells to mediate DTH to MCA-1490.

TABLE V

DTH TO MCA-1490, AS TRANSFERRED BY T CELLS FROM LINE 90.3, IS SUPPRESSED BY A FACTOR PRODUCED BY T—T HYBRIDOMA I-K54*

| Cells Transferring DTH | Source of Suppressor Factor (culture medium) | Mean Footpad Swelling ($\times 10^{-3}$ in. $\pm$ SE) | |
|---|---|---|---|
| | | Experiment 1 | Experiment 2 |
| 90.3 | None (diluent) | 19.2 ± 1.6 | 15.0 ± 2.2 |
| | I-K54 1.0 ul | 8.2 ± 0.8† | Not done |
| | I-K54 0.1 ul | 9.4 ± 0.9† | 3.0 ± 0.4† |
| | BW5147 1.0 ul | 20.3 ± 1.4 | Not done |
| | BW5147 0.1 ul | 19.6 ± 1.6 | 13.3 ± 1.2 |
| Normal T | None (diluent) | 9.6 ± 1.1 | 4.8 ± 0.6 |
| Diluent | None (diluent) | 7.0 ± 0.7 | 4.0 ± 0.6 |

*Line 90.3 T cells were mixed with MCA-1490 cells and injected into the footpads of naive BALB/c mice to assay for DTH, as described in Table III. Medium of I-K54 or BW5147 (control) cells was diluted to 5 ul and injected into the same footpad as the T cell-tumor cell mixture. Five mice were used per group.
†The response of these mice was significantly lower than that of mice receiving 90.3 cells, tumor cells and diluent, at P less than 0.01 by Student's t test.

Since both 90.3 effector cells and K54 suppressor cells appeared to carry a mAb 4.72-defined idiotope, we evaluated whether this idiotope was present also on suppresser factors made by T cell hybridomas other than K54. Suppressor factors derived from four different T cell hybridomas were assayed for suppressive activity after incubation with immobilized mAb 4.72. Spent medium from the four hybridomas and from BW5147 (control) cells, was passed through columns of either mAb 4.72 or mAb 8.2 (control), which had been covalently coupled to agarose. The effluents were assayed for suppression of DTH to MCA-1490, by injecting them i.v. into BALB/c mice immediately after they had been subcutaneously immunized to MCA-1490 (Table VI).

TABLE VI mAb 4.72 BINDS TO FACTORS WHICH ARE PRODUCED BY T CELL HYBRIDOMAS AND WHICH SUPPRESS DTH TO MCA-1490*

| Source of Suppressor Factors (culture medium from) | Mean Footpad Swelling ($\times 10^{-3}$ in. $\pm$ SE) in Mice Injected with Medium Adsorbed with | |
|---|---|---|
| | mAb 8.2 | mAb 4.72 |
| BW5147 (control) | 24.2 ± 1.8 | 23.4 ± 0.8 |
| Hybridoma I-K54 | 7.8 ± 1.0† | 22.9 ± 1.2 |
| Hybridoma II-15 | 9.6 ± 2.8** | 18.4 ± 2.2 |
| Hybridoma II-32 | 10.8 ± 2.0** | 24.8 ± 2.4 |
| Hybridoma II-122 | 11.0 ± 1.2† | 23.6 ± 2.0 |

*Spent culture medium of T cell hybridomas I-K54, II-15, II-32 and II-122 or of BW5147 (control) cells were passed through columns of mAb 4.72 or 8.2 covalently coupled to agarose. The effluents were assayed for suppression of the inductive phase of DTH to MCA-1490 as described in Table II. Statistical significance of differences in footpad swelling, as compared to control mice receiving diluent was estimated by Student's t test.
†P less than 0.001
**P less than 0.01

As shown in Table VI, media derived from each of the four T hybridomas and passaged through a control column (of mAb 8.2) suppressed the induction of DTH to MCA-1490, while this suppression was removed by passage through a mAb 4.72 column. All four suppressor factors thus appeared to express the idiotope defined by mAb 4.72.

This result suggested that the idiotope defined by mAb 4.72 was dominant in regulating the suppressor response to MCA-1490. However, as factors made by only four hybridomas were studied, we next analyzed the presumably polyclonal suppressor response in mice bearing a growing MCA-1490 sarcoma. This experiment was done on the basis of the demonstration that sera from mice carrying MCA-1490 or MCA-1511 sarcomas can suppress the induction of DTH to the respective tumors (Table VII).

TABLE VII

SERA FROM MICE BEARING SARCOMA MCA-1490 OR MCA-1511 SUPPRESSES DTH TO THE RESPECTIVE TUMOR*

| | Mean Footpad Swelling ($\times 10^{-3}$ in. $\pm$ SE) in Mice Immunized and Challenged with | |
|---|---|---|
| Serum Donor | MCA-1490 | MCA-1511 |
| MCA-1490 tumor-bearer mice | 6.7 ± 1.3† | 20.0 ± 0.4 |
| MCA-1511 tumor-bearer mice | 15.9 ± 2.6 | 10.4 ± 2.3† |
| Naive mice | 17.5 ± 4.5 | 22.2 ± 2.6 |
| None (diluent) | 15.0 ± 1.4 | 21.0 ± 1.4 |

*Sera from mice bearing progressively growing MCA-1490 or MCA-1511 tumors or from control mice were diluted and 100 ul injected i.v. into mice immediately before immunization to MCA-1490 or MCA-1511. DTH was elicited and measured as described in Table I. Mean footpad swelling in unimmunized mice was 5.3 ± 1.2 after challenge with MCA-1490 and 6.3 ± 0.3 after challenge with MCA-1511.
†The response of these mice was significantly lower than that of mice receiving diluent at P less than 0.01 by Student's t test.

Sera from tumor-bearing mice were chromatographed on columns of mAb 4.72 or mAb 8.2 (control), the material bound to the columns was eluted, and effluents and eluates were assayed for suppression of DTH (Table VIII).

TABLE VIII mAb 4.72 BINDS SERUM FACTORS WHICH SUPPRESS DTH TO MCA-1490
BUT DO NOT BIND SERUM FACTORS WHICH SUPPRESS DTH TO MCA-1511*

| | Mice | | | | | |
|---|---|---|---|---|---|---|
| | | Intravenously injected | | | Mean Footpad Swelling ($\times 10^{-3}$ in. $\pm$ SE) | |
| Immunized with | Challenged with | Sera | Immunoadsorbed on Column Prepared with | Fraction from Immunoadsorbent Column | Experiment 1 | Experiment 2 |
| MCA-1490 | MCA-1490 | MCA-1490 tumor-bearer | mAb 8.2 | Effluent | $6.0 \pm 1.3^\dagger$ | $6.0 \pm 1.4^\dagger$ |
| | | | mAb 8.2 | Eluate | $16.6 \pm 0.7$ | Not done |
| | | | mAb 4.72 | Effluent | $15.0 \pm 1.0$ | $16.0 \pm 2.0$ |
| | | | mAb 4.72 | Eluate | $7.2 \pm 0.8^\dagger$ | $8.0 \pm 1.3^\dagger$ |
| | | None (diluent) | — | — | $15.0 \pm 1.4$ | $15.0 \pm 0.3$ |
| None (unimmunized) | MCA-1490 | None | | | $5.3 \pm 6.3$ | $6.3 \pm 0.7$ |
| MCA-1511 | MCA-1511 | MCA-1511 tumor-bearer | mAb 8.2 | Effluent | $10.2 \pm 1.2^\dagger$ | $10.2 \pm 1.2^\dagger$ |
| | | | mAb 8.2 | Eluate | $19.2 \pm 2.0$ | Not done |
| | | | mAb 4.72 | Effluent | $9.8 \pm 1.6^\dagger$ | $9.8 \pm 1.2$ |
| | | | mAb 4.72 | Eluate | $16.8 \pm 1.5$ | $15.8 \pm 1.2$ |
| | | None (diluent) | — | — | $21.0 \pm 1.4$ | $17.6 \pm 0.8$ |
| None (unimmunized) | MCA-1511 | None | | | $6.3 \pm 0.3$ | $5.7 \pm 0.7$ |

*Sera from mice bearing MCA-1490 or MCA-1511 tumors were passed through immunoadsorbent columns of mAb 4.72 or mAb 8.2, covalently coupled to agarose. The columns were washed, and bound material was eluted with 3 M NaSCN and desalted on Sephadex G-25 which had been equilibrated with PBS. The effluents and eluates of each column were assayed for suppression of the inductive phase of DTH as described in Tables XIII and XVI.
$\dagger$The response of these mice was significantly lower than that of immunized mice receiving diluent at P less than 0.01 by Student's t test.

As shown in Table VIII, sera from mice bearing MCA-1490 suppressed DTH to MCA-1490 after passage through a control column (of mAb 8.2) but not after passage through a mAb 4.72 column, and material which suppressed DTH to MCA-1490 was recovered in an eluate of the latter column. Immunoadsorption with mAb 4.72 did not remove the ability of sera from mice bearing a different tumor, MCA-1511, to suppress DTH to that tumor.

Our results indicate that suppression of DTH to MCA-1490 was associated with an idiotope recognized by mAb 4.72 and that suppression of DTH to MCA-1511 did not involve that idiotope.

6.6. Serotherapy of Mice With MCA-1490 or MCA-1511 Tumors

We investigated whether injection of mAb 4.72 and 5.96 protected mice against challenge with the appropriate tumor cells (MCA-1490 or MCA-1511, respectively) and whether it had any therapeutic effect on established tumors. The mAb were injected intraperitoneally; the i.v. route was not chosen in view of the evidence (see Section 6.3, supra) that mice so injected showed decreased DTH reactivity to tumor antigens.

In the first set of experiments, mice (20 per group) were injected with either mAb 4.72 or (control) mAb 8.2. They were challenged, 5 days later, with MCA-1490 cells at a dose which, according to pilot tests, caused progressive tumor growth in approximately 90% of the recipients. Priming with mAb 4.72 delayed the appearance of transplanted MCA-1490 sarcoma by 5 to 9 days compared to controls, but there was no significant difference between the percentage of mice dying from progressively growing tumors. The growth of the antigenically unrelated MCA-1511 sarcoma was not affected. Varying the amount of mAb 4.72 injected did not improve the results. Rather, in one experiment in which mice received 100 times the amount of mAb 4.72 which could prime for DTH, the growth of MCA-1490 was accelerated as compared to both control mice and control tumors. A dual effect has also been reported in the manipulation of immunity to vital antigens, using anti-idiotypic antibodies (Kennedy, R. C. and Dreesman, G. R., 1984, J. Exp. Med. 159:655; Kennedy, R. C., et al., 1984, J. Virol. 50:951).

In a second series of experiments, mice were first injected with MCA-1490 cells subcutaneously, and this was followed 7 or 8 days later by 100 ug mAb i.p.; at this point in time, tumors had become barely palpable in about 50% of the mice. The antibody injection was repeated at 4 to 5 day intervals for a total of four injections. In all of the 10 mice given mAb 4.72, the original small tumor nodules had regressed when the experiment was terminated after 6 weeks. At that time, 6 of 10 mice given the control mAb 8.2 had progressively growing tumors with a surface area greater than or equal to 0.20 cm². This difference between the two groups was significant at P less than or equal to 0.05.

To test the limits of this form of therapy, the dose of tumor cells was increased by giving tumor cells at a dosage twice that required to grow out in 100% of the recipients. The two antigenically distinct satcomas, MCA-1490 and MCA-1511, were treated in parallel with the appropriate anti-idiotypic mAb (4.72 and 5.96, respectively). Groups of ten mice were injected with mAb 4.72 (related to MCA-1490), mAb 5.96 (related to MCA-1511), mAb 8.2 (as a control), or diluent (as another control), starting nine days after transplantation when all the mice had barely palpable tumors (greater than 0.2 cm²). As shown in FIG. 5, treatment with mAb 4.72 limited the growth of MCA-1490, but not of MCA-1511, and treatment with mAb 5.96 similarly inhibited MCA-1511, but not MCA-1490. The differences between mice receiving the appropriate anti-idiotypio mAb and any of the three controls (the inappropriate anti-idiotopic mAb, mAb 8.2 or diluent) was statistically significant at P less than or equal to 0.001. FIG. 6 presents these data in more detail by showing the number of mice with tumors in each group treated with mAb 4.72 or mAb 5.96. In each of the two groups receiving appropriate anti-idiotypic antibody, tumors regressed in 5 or 7 of the 10 treated mice, and three of these mice (in each of the two groups) remained free of tumor for two weeks after the last injection of antibody. At that time, all the mice in the control groups had tumors with a surface area greater than 1.5 cm$^2$, and some of the mice had already died with tumor.

We conclude that treatment of mice with established sarcomas MCA-1490 and MCA-1511, using intraperitoneal injection of the appropriate anti-idiotypic mAb, had significant antitumor activity.

6.7. Discussion

We herein describe evidence that T cells and anti-idiotypic B cells were generated in mice which either bore a growing sarcoma or had been immunized to such a tumor. T cells bearing the same idiotope included cells which mediated tumor-specific DTH and cells which made a soluble, tumor-specific suppressor factor. By employing anti-idiotopic mAb, we could manipulate the antitumor response so as to limit the growth of established syngeneic satcomas expressing the relevant tumor antigens.

Two mAb, 4.72 and 5.96, were used. They were isolated from BALB/c mice which had been immunized to satcomas MCA-1490 or MCA-1511, respectively. We regard the two mAb as anti-idiotopic in view of three findings which relate to their functions. First, each mAb induced tumor-specific DTH in syngeneic mice in the absence of tumor antigen. Second, this induction was allotype restricted. Third, neither mAb bound to the immunizing tumor.

The idiotope defined by mAb 4.72 was identified on T cells which mediated DTH to MCA-1490. This was done in an experiment in which mAb 4.7.2 was used to isolate from lymph nodes of mice responding to MCA-1490, a small fraction of lymphocytes which expressed the 4.72-defined idiotope and from which a T cell line, 90.3, could be established. Naive mice receiving the 90.3 cells displayed DTH to MCA-1490 but not to MCA-1511, and the 90.3 cells prevented the outgrowth of sarcoma MCA-1490 but not sarcoma MCA-1510 or MCA-1511. Cheever et al. (1986, J. Exp. Med. 163:1100) have demonstrated the ability of Lyt $1^+2^{-T}$ cells to limit the progression of murine leukemia. However, their protocol includes restimulation of the cultured cells with antigen as well as IL-2. The tumor specificity of the 90.3 cells argues against their being lymphokine-activated killer cells.

Products of T cells which suppressed the DTH response to MCA-1490 were found to express the idiotope defined by mAb 4.72. This was shown in studies on four T cell hybridomas which had been obtained by fusing thymocytes from mice carrying growing MCA-1490 tumors with BW5147 cells (Nelson, K., et al., 1985, in T-cell Hybridomas, Taussig, M. J., ed., CRC Press, p.129). The products of these hybridomas had previously been found to suppress the lysis of $^{51}$Cr labelled MCA-1490 cells by specifically immune cytolytic T cells (Nelson, K. A., et al., 1980, Proc. Natl. Acad. Sci. U.S.A. 77:2866) and to suppress the induction of DTH to MCA-1490 (Cory, J., et al., 1981 in Monoclonal Antibodies and T Cell Hybridomas, Hammerling, G. J., et al, eds., Elsevier/North-Holland Biomedical Press, p. 503); this suppression was specific for the response to MCA-1490 and was allotype restricted. Furthermore, the suppressor factors had been found to bind to MCA-1490 cells from which they could be recovered by solution (Nelson, K. A., et al., 1980, supra). In the examples described herein, we demonstrate that mAb 4.72 inhibits the binding of all four suppressor factors to MCA-1490 cells. This suggests that the idiotope defined by mAb 4.72 is associated with the site on the suppressor factor which binds to a tumor antigen on MCA-1490 cells. T suppressor factors bearing the idiotope defined by mAb 4.72. could both suppress the priming for. DTH by mAb 4.72 and the transfer of DTH to MCA-1490 by T cells from line 90.3 (which, as discussed supra, express the mAb 4.72-defined idiotope).

Based on these data, we suggest the following model: mAb 4.72 defines an idiotope which occurs on tumor-specific regulatory T cells and is dominant in the immune response of BALB/c mice to MCA-1490. During this response, the same or a cross-reacting idiotope activates a B cell clone producing anti-idiotypic antibody. The latter antibody is presumed to regulate both suppressor T cells and DTH-reactive T cells. Our model assumes, as supported by various studies (Rajewski, K. and Takemori, T., 1983, Ann. Rev. Immunol. 1:569F Urbain, J., et al., Ann. Immunol. 133D:179F Binz, H. and Wigzell, H., 1978, J. Exp. Med. 147:63; Ertl, H. C. J., et al., 1982, Proc. Natl. Acad Sci. U.S.A. 79:7479), that T and B cells interact in idiotypic networks. Our model also assumes that a B cell derived anti-idiotypio antibody (mAb 4.72 in our example) arose in response to a T cell idiotope and not to a parallel set of idiotope-positive B cells. In support of this, we have no evidence for tumor cell binding antibody in the response of mice to MCA-1490, nor have we been able to induce such antibody by immunizing with mAb 4.72. This is in contrast with the ease in demonstrating idiotope-positive, antigen-reactive T cells. The data support the hypothesis that a T cell idiotope can induce an anti-idiotypic response in the B cell compartment, which in its turn can regulate T cell responses in both upwards and downwards directions.

An alternative model assumes that the mAb 4.72-defined idiotope displays an internal image of the MCA-1490 tumor antigen. However, it is difficult to reconcile that model with the allotype (Igh-1) restriction of the induction of DTH by mAb 4.72.

In the present study, we used the anti-idiotypic mAb 4.72 in a successful attempt to remove the suppressive activity of sera from mice bearing MCA-1490. All the circulating serum factors which could be detected by measuring suppression of DTH to MCA-1490 appeared to express the 4.72-defined idiotope.

As described supra, we next examined the feasibility of manipulating the immune response to tumor by using anti-idiotypic mAb. mAb 4.72 and 5.96 were chosen, as they could both induce DTH reactive cells in naive mice, and as the idiotope defined by one of the mAb, 4.72, was expressed on DTH reactive cells in immune mice. Our first set of experiments addressed the question of tumor prevention, by giving mAb before tumor transplantation, while a second series of experiments dealt with therapy of already established tumors. When mice received mAb 4.72 before they were challenged with MCA-1490 cells, tumor outgrowth commonly was delayed by a few days. These antitumor effects did not improve by increasing mAb dose; in fact, an experiment with a 100-fold increase in mAb dose showed accelerated tumor growth.

In a second set of experiments, we investigated the therapeutic value of injecting mice with established satcomas intraperitoneally with the appropriate anti-idiotypic-mAb. Injection of mAb 4.72 (but not of mAb 5.96) limited the growth of sarcoma MCA-1490 and, more importantly, it induced the regression of 3 out of 10 such sarcomas and prolonged the survival of the treated mice. Injection of mAb 5.96 (but not of mAb 4.72) had a similar effect in mice with sarcoma MCA-1511, also inducing regression of 3 out of 10 sarcomas.

7. ANTI-IDIOTYPIC ANTIBODY SPECIFIC TO AN IDIOTYPE WHICH RECOGNIZES A HUMAN. MELANOMA-ASSOCIATED GD3 GANGLIOSIDE ANTIGEN

Mouse monoclonal antibody (mAb) MG-21 (Hellstrom et al., 1985, Proc. Natl. Acad. Sci. U.S.A. 82:1499–1502; see copending U.S. applications Ser. No. 831,684, filed Feb. 21, 1986, and Ser. No. 834,162 filed Feb. 26, 1986) recognizes a GD3 ganglioside antigen expressed on the surface of cells from most human melanomas and in trace amounts on normal cells (Dippold, W. G., et al., 1980, Proc. Natl. Acad. Sci. U.S.A. 77:6114–6118; Nudelman, E., et al., 1982, J. Biol. Chem. 257:12752–12756; Yeh, M. Y., et al., 1982, Int. J. Cancer 29:269–275). mAb MG-21 demonstrates complement-dependent cytotoxicity (CDC) to GD3-positive cells with human serum as the source complement, and antibody-dependent cellular cytotoxicity (ADCC) to GD3-positive cells with human lymphocytes (Hellstrom et al., 1985, Supra). The GD3 antigen to which MG-21 binds has been used with some success as the target for a passively administered mouse mAb, R24 (Houghton, A. N., et al., 1985, Proc. Natl. Acad. Sci. U.S.A. 82:1242–1246), whose specificity and biological activity is similar to that of MG-21. As described in the examples infra, we have used MG-21 (Ab1) as an immunogen to generate a mouse monoclonal anti-idiotypic antibody (Ab2), which was designated 2C1. This mAb, which is an IgG2a, was selected by its capacity to inhibit the binding of MG-21 to a GD3-positive melanoma cell line. mAb 2C1 was found to bind to MG-21 with high avidity, but not to any of six other mouse mAb. It could completely abrogate the binding of MG-21 to GD3-positive melanoma cells as well as to purified GD3, and it inhibited the CDC and ADCC properties of MG-21 in a dose-dependent fashion. By using mAb 2C1 as a probe, an assay was developed to monitor human antibodies to mAb MG-21 in patients receiving mAb MG-21 for therapeutic or diagnostic purposes. A detailed description of each step in this embodiment of the invention is presented in the subsections below.

7.1. Materials and Methods

7.1.1. Mice

Eight to twelve week-old BALB/c female mice were purchased from the Animal Facilities of the Fred Hutchinson Cancer Research Center (Seattle, Wash.).

7.1.2. Target Cells

Human melanoma cell line M-2669 clone 13 was used; for simplicity, it is referred to here as M-2669. It had been established from a metastatic melanoma and cloned (Beaumier, P. L., et al., 1986, J. Nucl. Med. 27;824–828). Cells from this clone strongly express the GD3 antigen defined by mAb MG-21 as determined by a binding assay (id.). The melanoma cells were grown in 6% $CO_2$ in air in RPMI 1640 culture medium (Gibco, Grand Island, N.Y.) containing 15% heat-inactivated fetal calf serum (Hyclone Laboratories, Inc., Logan, Utah) buffered with $NaHCO_3$ and supplemented with penicillin (100 U/ml), streptomycin (100 mg/ml) and L-glutamine (290 mg/liter).

7.1.3. Glycolipid

GD3 ganglioside antigen was purified from M-2669 clone 13 melanoma cells as described (Nudelman, E., et al., 1982, J. Biol. Chem. 257:12752–12756), and was provided by Dr. Sen-itiroh Hakomori at Fred Hutchinson Cancer Research Center (Seattle, Wash.).

7.1.4. Monoclonal Antibodies

MG-21 (Hellstrom, I., et 21., 1985, Proc. Natl. Acad. sol. U.S.A. 82:1499–1502) is an IgG3 antibody which binds to a GD3 ganglioside antigen expressed strongly on about 80–90% of human melanomas (Nudelman, E., et al., 1982, J. Biol. Chem. 257:12752–12756; Yeh, M. -Y., 1982, Int. J. Cancer 29:269–275). MG-2; can mediate CDC in the presence of human serum and ADCC in the presence of human peripheral blood lymphocytes (PBL), and it can inhibit the outgrowth of human melanoma xenografts in nude mice (Hellstrom, I., et al., 1985, Proc. Natl. Acad. Sci. U.S.A. 82:1499–1502).

mAb 2A-14 is an IgG3 which also binds to the GD3 ganglioside antigen, but to an epitope which by crossblocking experiments appears to be different from that recognized by MG-21.

mAb 96.5 is an IgG2a which binds to p97, a melanoma-associated cell surface glycoprotein (Brown, J. P., et al., 1981, J. Immunol. 127:539–546; see copending U.S. patent applications Ser. Number 827,313, filed Feb. 7, 1986 and Ser. Number 007,230, filed Jan. 27, 1987).

mAb L6 is an IgG2a which binds to a carbohydrate antigen expressed strongly on cells from most human carcinomas but not melanomas (Hellstrom, I., et al., 1986, Cancer Res. 46:3917–3923; see copending U.S. patent applications Ser. No. 684,759, filed Dec. 21, 1984 and Ser. Number 776,321, filed Oct. 18, 1985).

mAb L20 is in IgG1 which identifies a 110 kd protein expressed on the surface of cells from most human carcinomas but not melanomas (id.).

mAb 7T1.1 is an IgG3 immunoglobulin specific for blood group A antigen strongly expressed on many human carcinomas.

mAb 1G3.10 is an IgG3 antibody specific for blood group A-like antigen also expressed on many human carcinomas.

mAb 26.8, which was used as an Ab2 control, is an IgG1 which binds to an idiotope on mAb 96.5 specific for the p97 melanoma antigen. mAb 26.8 can inhibit the binding of mAb 96.5 to p97.

P1.17 is an IgG2a mouse myeloma protein which was obtained from the American Type Culture Collection (ATCC Accession No. TIB 10).

Antibodies were purified either from spent culture medium or ascitic fluid by affinity chromatography on protein A-Sepharose CL-4B as described by Ey et al. (1978, Immunochemistry 15:429–436).

7.1.5. Coupling of Antibody With Keyhole Limpet Hemocyanin

Antibody MG-21 was coupled to keyhole limpet hemocyanin (KLH) by chemical cross-linking in the presence of glutaraldehyde according to the procedures of Bona et al. (1979, J. Exp. Med. 149:815–823). In brief, i ml of mAb MG-21 solution (3.6 mg/ml) was mixed with i ml of KLH solution (3 mg/ml) in 0.1 M phosphate buffer, pH 7.5. Coupling was initiated by the addition of 1 ml of a 0.25% solution of glutaraldehyde (Sigma Chemical, St. Louis, Mo.). The mixture was shaken at room temperature for 1 hour. The reaction was stopped by adding 250 pl of 1M glycine. Antibody-KLH conjugate was stored frozen at −20° C. before use.

7.1.6. Production of Monoclonal Anti-Idiotypic Antibodies (Ab2) Specific For MG-21 (Ab1)

Two 8-week-old BALB/c female mice were immunized intraperitoneally (i.p.) with 100 µg of MG-21-KLH conjugate in complete Freund's adjuvant. Two weeks later, the same amount of conjugate was given i.p. in incomplete Freund's adJuvant. Another 8 weeks later, the mice were boosted again with conjugate in saline. Four days after the last immunization, spleens were removed and the harvested cells were fused with NS-1 mouse myeloma cells by use of polyethylene glycol. Hybridomas secreting anti-idiotypic antibodies specific for MG-21 were selected, grown in HAT medium, and cloned using established procedures (Yeh, M. -Y., et al., 1979, Proc. Natl. Acad. Sci. U.S.A. 76:2927–2931).

7.1.7. mAb (Ab1) Binding Inhibition Assay

Enzyme-linked immunosorbent assays (ELISAs) of antibody binding were used for the initial screening of hybridomas secreting anti-idiotypic antibodies. In this assay, hybridoma culture supernatants were tested for inhibition of binding of MG-21 ("Ab1") to M-2669 cells, as evidence for the presence of anti-idiotypic antibodies ("Ab2"). M-2669 melanoma cells, seeded into polyvinyl chloride plates ($10^5$ cells/well) and fixed with 0.5% glutaraldehyde, were used as targets. One hundred ul of mAbMG-21 (5 µg/ml) were mixed with equal volumes of hybridoma supernatants, incubated at 4° C. for 2–4 hours, and then added to the target cells. After another incubation for 1 hour at 37° C., the plates were washed three times with 0.05% Tween-20 in PBS (PBS-Tween buffer). The cells were then incubated with 100 ul of goat anti-mouse IgG antibody-peroxidase conjugate (Boehringer Mannheim Biochemicals, Indianapolis, Ind.) diluted 1/10,000 in PBS-Tween buffer at 37° C. for 30 minutes, and washed again. One hundred ul of o-phenylenediamine (OPD) containing 0.015% $H_2O_2$ in citrate phosphate, pH 5.0, were dispensed in each well as substrate for peroxidase. About 3–5 minutes later, 100 ul of 1.3 N $H_2SO_4$ were added for blocking the enzymesubstrate reaction. Absorbance was measured at 492 nm/630 nm dual wavelength for each well in a GSC microplate reader (Genetic System Corp., Seattle, Wash.).

To investigate the dose-dependency of the inhibitory effect of anti-idiotypic antibody (Ab2) on the binding of MG-21 (Ab1) to cells and GD3 antigen, 100 ul of a fixed concentration (5 µg/ml) of MG-21 were mixed with 100 ul of various concentrations of appropriate anti-idiotypic or control antibodies, incubated at 37° C. for 1 hour, and then added to wells precoated with M-2669 cells ($10^5$/well) or purified GD3 antigen (200 ng/50 µl/well). The remaining procedures were the same as those above.

7.1.8. Determination of Immunoglobin Isotype

Goat antisera to the specific class of mouse immunoglobulin were used (Southern Biotechnology Assoc., Birmingham, Al.). Fifty µl of each such anti-serum was diluted in PBS (1 µl/ml), plated into 96-well plates (Dynatech, Alexandria, Va.), and incubated overnight at 4° C. The plates were washed once with PBS-Tween buffer, and then incubated for 1 hour at room temperature with 100 µl per well of RPMI 1640 medium containing 15% fetal calf serum (FCS). After washing, 50 µl of hybridoma spent culture medium were added, followed by incubation of the plates at room temperature for 1 hour and one washing with PBS-Tween buffer. Subsequently, 50 µl of goat anti-mouse IgG antibody conjugate diluted 1/10,000 in PBS-Tween buffer were added to each well. The plates were incubated for 30 minutes at 37° C. and washed five times with PBS-Tween buffer, after which 100 µl of OPD substrate were added to each well. Five minutes later, the reaction was stopped by adding 100 µl of 1.3 N $H_2SO_4$, and the absorbance was measured in a GSC microplate reader.

7.1.9. Anti-Idiotypic Antibody (Ab2) Binding Assay

A binding assay was used to determine whether the ability of Ab2 to inhibit the binding of MG-21 (Ab1) was specific. Purified MG-21 at 0.5 µg/100 µl was added to coat each well of 96-well polyvinyl chloride plates (Costar, Cambridge, Mass.), after which 200 µl per well of RPMI 1640 medium containing 15% FCS was added as a "blocker" to prevent antibody binding to plastic. After washing, 100 µl of purified Ab2 or control immunoglobulin P1.17 were added at various concentrations. The plates were incubated at 37° C. for 30 minutes, and then washed three times with PBS-Tween buffer. One hundred µl of peroxidase-conjugated rabbit anti-mouse IgG which had the same isotype as the Ab2 were then added after dilution in PBS-Tween buffer. After incubation for 30 minutes at 37° C., followed by extensive washing, 100 µl of OPD substrate were added and incubated for 3–5 minutes in the dark. Finally, 100 µl of 1.3 N $H_2SO_4$ were added. The plates were read by a GSC microplate reader.

7.1.11. Radioiodination of Antibody and Direct $^{125}$I-Ab2 Binding Assay

One hundred µl of purified mAb were incubated with 500 uCi $Na^{125}I$ (Amersham Corporation, Arlington Heights, Ill.) and 40 ug of chloramine-T in 500 µl of PBS at 4° C. for three minutes. Labeled mAb was separated from free $^{125}I$ by gel filtration on a column of Sephadex G-25; the specific activity was approximately $4\times10^6$ cpm/µg. The labeled mAb was diluted in 15% FCS in PBS before use.

For a direct $^{125}$I-Ab2 binding assay, 100 µl of various purified mAb (50 µg/ml) in 15 mM $NaHCO_3$ at pH 9 were plated into 96-well plates (Dynatech, Alexandria, Va.) at 4° C. overnight. After washing, the wells were blocked by incubation overnight at 4° C. with 200 µl of RPMI 1640 medium containing 15% FCS. The plates were washed three times with PBS-Tween buffer, and $2.5\times10^5$ cpm of labeled Ab2 in 100 µl of 30% FCS were added to each well and incubated at room temperature for 1 hour. After thorough washing, the bound radioactivity was dissolved in 100µl of 2M NaOH, transferred to test tubes, and counted in a Gamma counter (Beckman, Irvine, Calif.).

7.1.11. Antibody-FITC Conjugation

Fluorescein isothiocyanate (FITC) was conjugated to mAb MG-21 as described by Goding (Goding, W., 1976, J. Immunol. Methods 13:215–226). Briefly, 2 mg of purified MG-21 was dialyzed overnight in 0.2M carbonate/bicarbonate buffer, pH 9.5. FITC (Molecular Probes Inc., Junction City, Org.) dissolved in dimethyl sulfoxide (1 mg/ml) was added at a ratio of 40 µg FITC/mg of antibody. The mixture was incubated at 37° C. for 45 minutes, after which conjugated mAb was separated from free FITC by passage through a G-25 Sephadex column equilibrated with PBS containing 0.1% $NaN_3$. The fluorescein/antibody conjugation ratio was about 3.5 to 4.0. The conjugated mAb was stored at −20° C. in PBS containing 1% bovine serum albumin (BSA).

7.1.12. Fluorescence Activated Cell Sorter Analysis

For binding inhibition analysis using a fluorescence activated cell sorter (FACS), 100 ul of FITC-conjugated MG-21 were incubated for 30 minutes at 37° C. with 100 µl of various concentrations of purified Ab2 or control antibodies in 10% normal mouse serum. The antibody mixtures were then added to test tubes containing 1×10⁶ paraformaldehyde-fixed M-2669 cells in 100 μl of PBS. After 30 minutes of incubation, the cells were washed two times with PBS, and then analyzed with a Coulter Epics C fluorescence activated cell sorter (Coulter Corporation, Hialeah, Fla.). Data were expressed as linear fluorescent equivalence (LFE), which represents relative fluorescent intensity.

7.1.13. Complete-Dependent Cytotoxicity Assay

To test whether Ab2 specific for MG-21 can inhibit complement-dependent cytotoxicity (CDC) of mAb MG-21, a 4-hour $^{51}$Cr-release assay (Hellstrom, I., et al., 1985, Proc. Natl. Acad. Sci. U.S.A. 82:1499–1502) was used. Briefly, 10⁶ target cells were labeled with 100 μCi of $^{51}$Cr for 2 hours at 37° C. After labelling, the cells were washed three times, resuspended in RPMI 1640 medium containing 15% FCS, and 20,000 labeled cells, suspended in 45μl of RPMI 1640 medium, and seeded into each well of Microtiter V-bottom plates (Dynatech Laboratories, Alexandria, Va.). Various concentrations of purified MG-21 were combined with different concentrations of purified Ab2 (or control mAb) to test for inhibition of CDC. They were added in 90 μl per well, followed by 65μl of undiluted unheated human serum per well. After incubation for 4 hours at 37° C., the plates were centrifuged at 400 ×g, 100 μl of supernatants from each well were removed, and the level of radioactivity was determined by a Gamma counter (Beckman, Irvine, Calif.). Spontaneous release was defined as the cpm released into the medium from target cells which had not been exposed to antibody or complement, and total release was estimated as the cpm released from target cells that were osmotically lysed. Percent cytotoxicity was calculated by the following formula:

$$\text{Percent cytotoxicity} = \frac{\text{Experimental release} - \text{Spontaneous release}}{\text{Total release} - \text{Spontaneous relase}} \times 100$$

7.1.14. Antibody-Dependent Cellular Cytotoxicity Assay

To test whether Ab2 can inhibit the antibody-dependent cellular cytotoxicity (ADCC) of mAb MG-21, a 4-hour release assay was employed. PBL from healthy human subjects were used as effector cells. They were separated on Ficoll-Hypaque and prescreened for low natural killer (NK) cell activity. Only lymphocytes with low NK activity (less than 10% $^{51}$Cr-release over four hours) were used. After labeling of the target cells, they were plated (2×10⁴ cells/50 μl) into Microtiter plates as for the CDC assay. Fifty μl of purified MG-21 and 50μl of purified Ab2 (or control) mAb were added at various concentrations, followed by 2×10⁶ lymphocytes per well in 50μl of medium; the ratio of lymphocytes to target cells was 100:1. The mixtures were incubated for 4 hours at 37° C. in a 6% $CO_2$ in air atmosphere. Subsequently, the plates were centrifuged, and 100 μl of supernatants were transferred from each well for radioactivity measurement. Percent cytotoxicity was calculated as for the CDC assay.

7.1.15. Competition Assay For Detecting ANTI-MG-21 Antibodies in Patient Sera A competition assay using monoclonal anti-idiotypic antibody (Ab2) as a probe was developed for detecting anti-MG-21 antibodies in the sera of patients treated with mAb MG-21. Briefly, 100 μl of Ab2 (5 μg/ml) in 15 mM $NaHCO_3$ buffer, pH 9, were added to each well of Falcon pro-bind assay plates (Becton Dickinson, Oxnard, Calif.), incubated at room temperature for 1 hour, and subsequently washed with PBS-Tween buffer. Seventy-five μl of mAb MG-21 (1 μg/ml) were preincubated for 45 minutes with equal volumes of sera from a patient or with pooled normal human serum; the sera were diluted 1:2.5, 1.:5 and 1:10 in PBS. Subsequently, 100 μl of the mixtures were added to the Ab2-precoated plates. After an additional incubation for 30 minutes at room temperature, the plates were washed twice with PBS-Tween buffer. One hundred μl of rabbit anti-mouse IgG3 antibody-peroxidase conjugate (Zymed Laboratories Inc., South San Francisco, Calif.), diluted 1:1,000 in PBS-Tween buffer, were added and incubated for 30 minutes at room temperature. After three washes with PBS-Tween buffer, the wells were filled with 100 μl of OPD substrate containing 0.015% $H_2O_2$ in citrate phosphate, pH 5.0. Five minutes later, 100 μl of 1.3 N $H_2SO_4$ were added, and the plates were read by a GSC microplate reader. Percentage of inhibition of MG-21 binding to mAb 2C1 was calculated by the following formula:

$$\text{Percent inhibition} = \left(1 - \frac{\text{OD in the presence of patient serum}}{\text{OD in the presence of normal human serum}}\right) \times 100$$

Serum samples from three of eight patients with advanced melanoma, which were enrolled in a phase I trial of mAb MG-21, were tested by this assay. Briefly, MG-21 in 5% human serum albumin had been infused to these patients over a 4–6 hour time period with the infusions being repeated daily for 7 days. The serum samples were taken prior to treatment and at various intervals after, and were stored at −80° C. until analysis.

7.2. Results

7.2.1. Selection of Hybridomas

Spleen cells from mice immunized with MG-21 were fused with NS-1 cells to generate hybridomas which could produce mAb to idiotypic determinants on MG-21; the latter mAb are referred to as Ab2. Two weeks after fusion, hybridoma supernatants were tested for antibodies inhibiting the binding of MG-21 to M-2669 cells. One hybridoma, 2Cl, which had such activity, was cloned and expanded. As shown in FIG. 7, supernatant of the 2C1 hybridoma strongly inhibited the binding of MG-21 to M-2669 cells but did not itself bind to M-2669 cells. Supernatant from the NS-1 myeloma was used as a control and did not inhibit the binding of MG-21.

Hybridoma 2C1 grew as an ascites tumor, when inoculated intraperitoneally into pristane-primed BALB/c mice. mAb 2C1 was found to be an IgG2a by solid phase enzyme immunoassay with goat anti-mouse Ig specific class antisera.

As shown in FIG. 8, mAb 2C1 gave strong binding to MG-21 when tested in an ELISA at concentrations between 0.08 μg/ml and 2 μg/ml with significant binding still being observed at 6.4 ng/ml. No binding was seen to P1.17, an IgG2a myeloma protein (FIG. 8).

7.2.2. mAb 2C1 is Specific For MG-21

To determine the degree of specificity of 2C1 for MG-21, a binding assay was performed using $^{125}$I-labeled $2C_1$. Six mouse mAbs, which had been generated against a variety of human tumors, were included as controls. As shown in FIG. 9, mAb 2C1 bound strongly to MG-21 but not to any of the six control mAbs, two of which (2A-14 and 96.5) were specific for melanoma-associated antigens that were different from the epitope recognized by MG-21. Of these two mAb, 2A-14 reacts with an epitope of the GD3 antigen which is different from that recognized by MG-21.

7.2.3. mAb 2C1 (Ab2) Inhibits the Binding of MG-21 (Ab1) to M-2669 Cells and GD3 Antigen in a Dose-Dependent Manner A binding assay was used to titrate how much mAb 2C1 was required as Ab2 to inhibit the binding of MG-21 (Ab1) to M-2669 cells. As shown in Table IX, mAb 2C1 completely inhibited the binding of MG-21 to M-2669 cells when present at a concentration equal to or greater than that of MG-21; two control immunoglobulins, mAb 26.8 and P1.17, gave no significant inhibition.

TABLE IX

DOSE-DEPENDENT INHIBITORY EFFECT OF mAb 2C1 ON THE BINDING OF mAb MG-21 TO M-2669 CELLS

| Antibody 1 concentration | Antibody 2 concentration | Absorbance at 492/630 nm[1] |
| --- | --- | --- |
| MG-21 (2.5 µg/ml) | None | 0.324 ± 0.015[2] |
| MG-21 (2.5 µg/ml) | mAb 2C1 (10 µg/ml) | 0.071 ± 0.029* |
| MG-21 (2.5 µg/ml) | mAb 2C1 (5 µg/ml) | 0.043 ± 0.026* |
| MG-21 (2.5 µg/ml) | mAb 2C1 (2.5 µg/ml) | 0.053 ± 0.002* |
| MG-21 (2.5 µg/ml) | mAb 2C1 (1.25 µg/ml) | 0.129 ± 0.019** |
| MG-21 (2.5 µg/ml) | mAb 2C1 (0.625 µg/ml) | 0.156 ± 00023** |
| MG-21 (2.5 µg/ml) | mAb 26.8 (10 µg/ml) | 0.305 ± 0.007 |
| MG-21 (2.5 µg/ml) | mAb 26.8 (5 µg/ml) | 0.329 ± 0.035 |
| MG-21 (2.5 µg/ml) | mAb 26.8 (2.5 µg/ml) | 0.315 ± 0.024 |
| MG-21 (2.5 µg/ml) | mAb 26.8 (1.25 µg/ml) | 0.337 ± 0.035 |
| MG-21 (2.5 µg/ml) | mAb 26.8 (0.625 µg/ml) | 0.330 ± 0.036 |
| MG-21 (2.5 µg/ml) | P1.17 (10 µg/ml) | 0.322 ± 0.049 |
| MG-21 (2.5 µg/ml) | P1.17 (5 µg/ml) | 0.368 ± 0.019 |
| MG-21 (2.5 µg/ml) | P1.17 (2.5 µg/ml) | 0.331 ± 0.019 |
| MG-21 (2.5 µg/ml) | P1.17 (1.25 µg/ml) | 0.318 ± 0.035 |
| MG-21 (2.5 µg/ml) | P1.17 (0.625 µg/ml) | 0.318 ± 0.031 |

[1]Data are presented as mean ± SE.
[2]Control
Differences statistically significant from control without Ab2, *, P less than 0.01; **, P less than 0.025.

In a parallel study, purified GD3, which is the antigen recognized by MG-21, was used instead of M-2669 cells. mAb 2C1 inhibited the binding of MG-21 to the purified GD3 ganglioside in a dose-dependent manner (Table X).

TABLE X

DOSE-DEPENDENT INHIBITORY EFFECT OF mAb 2C1 ON THE BINDING OF mAb MG-21 TO GD3 GANGLIOSIDE ANTIGEN

| Antibody 1 concentration | Antibody 2 concentration | Absorbance at 492/630 nm[1] |
| --- | --- | --- |
| MG-21 (2.5 µg/ml) | None | 0.486 ± 0.092[2] |
| MG-21 (2.5 µg/ml) | mAb 2C1 (25 µg/ml) | 0.085 ± 0.006* |
| MG-21 (2.5 µg/ml) | mAb 2C1 (12.5 µg/ml) | 0.073 ± 0.010* |
| MG-21 (2.5 µg/ml) | mAb 2C1 (6.25 µg/ml) | 0.075 ± 0.008* |
| MG-21 (2.5 µg/ml) | mAb 2C1 (3.125 µg/ml) | 0.379 ± 0.009 |
| MG-21 (2.5 µg/ml) | mAb 2C1 (1.563 µg/ml) | 0.502 ± 0.075 |
| MG-21 (2.5 µg/ml) | mAb 2C1 (0.782 µg/ml) | 0.482 ± 0.033 |
| MG-21 (2.5 µg/ml) | mAb 2C1 (0.391 µg/ml) | 0.533 ± 0.078 |

[1]Data are presented as mean ± SE.
[2]Control
Differences statistically significant from control without Ab2, *, P less than 0.01.

The inhibitory effect of mAb 2C1 on the binding of MG-21 to M-2669 cells was confirmed by FACS analysis using FITC-conjugated MG-21. Starting with 40 µg/ml of FITC-conjugated MG-21, which approximately corresponded to the saturation concentration, excess amounts of mAb 2C1 or control antibodies were added to M-2669 cells. FIG. 10 shows that 2C1 completely inhibited the binding of FITC-conjugated MG-21 to the tumor cells, while control antibodies had no effect.

7.2.4. Antibody 2C1 Inhibits CDC and ADCC Activity of MG-21 Against M-2669 Cells Previous experiments have shown that MG-21 gives strong CDC and ADCC with GD3-positive melanoma cells (Hellstrom, I., et al., 1985, Proc. Natl. Acad. Sci. U.S.A. 82:1499–1502). We now tested whether 2C1 had any effect on these activities. As shown in Table XI, CDC of MG-21 was completely abrogated by adding mAb 2C1 at a concentration greater than that of MG-21, but not by adding either of two control antibodies, mAb 26.8 or P1.17.

TABLE XI

INHIBITION OF CDC OF mAb MG-21 AGAINST M-2669 CELLS BY mAb 2C1

| Antibody 1 Final Concentration | Antibody 2 Final Concentration | Cytotoxicity[1] % |
| --- | --- | --- |
| MG-21 (5 µg/ml) | None | 100 (Control) |
| MG-21 (5 µg/ml) | mAb 2C1 (10 µg/ml) | 2* |
| MG-21 (5 µg/ml) | mAb 2C1 (1 µg/ml) | 84 |
| MG-21 (5 µg/ml) | mAb 2C1 (0.1 µg/ml) | 100 |
| MG-21 (5 µg/ml) | mAb 26.8 (10 µg/ml) | 100 |
| MG-21 (5 µg/ml) | mAb 26.8 (1 µg/ml) | 100 |
| MG-21 (5 µg/ml) | P1.17 (10 µg/ml) | 100 |
| MG-21 (5 µg/ml) | P1.17 (1 µg/ml) | 100 |
| MG-21 (1 µg/ml) | None | 64 (Control) |
| MG-21 (1 µg/ml) | mAb 2C1 (10 µg/ml) | 1* |
| MG-21 (1 µg/ml) | mAb 2C1 (1 µg/ml) | 0* |
| MG-21 (1 µg/ml) | mAb 2C1 (0.1 µg/ml) | 56 |
| MG-21 (1 µg/ml) | mAb 26.8 (10 µg/ml) | 69 |
| MG-21 (1 µg/ml) | mAb 26.8 (1 µg/ml) | 60 |
| MG-21 (1 µg/ml) | P1.17 (10 µg/ml) | 67 |
| MG-21 (1 µg/ml) | P1.17 (1 µg/ml) | 69 |

[1]Cytotoxicity was determined in a 4-hour $^{51}$Cr-release assay using normal human serum as a source of complement. No cytotoxicity was seen with human serum alone. Antibodies alone did not give any cytotoxicity. Significance was determined by student's t-test and is indicated by *, P less than 0.01.

Antibody 2C1 also completely inhibited the ADCC activity of MG-21 against M-2669 cells when its concentration was greater than that of MG-21, while no significant inhibition was seen with the two control antibodies (Table XII),

TABLE XII

INHIBITION OF ADDCC OF mAb MG-21 AGAINST M-2669 CELLS BY mAb 2C1

| Antibody 1 Final Concentration | Antibody 2 Final Concentration | Cytotoxicity[1] % |
| --- | --- | --- |
| MG-21 (5 µg/ml) | None | 40 (Control) |
| MG-21 (5 µg/ml) | mAb 2C1 (10 µg/ml) | 4* |
| MG-21 (5 µg/ml) | mAb 2C1 (1 µg/ml) | 16* |
| MG-21 (5 µg/ml) | mAb 2C1 (0.1 µg/ml) | 33 |
| MG-21 (5 µg/ml) | mAb 26.8 (10 µg/ml) | 44 |
| MG-21 (5 µg/ml) | mAb 26.8 (1 µg/ml) | 40 |
| MG-21 (5 µg/ml) | P1.17 (10 µg/ml) | 34 |
| MG-21 (5 µg/ml) | P1.17 (1 µg/ml) | 39 |
| MG-21 (1 µg/ml) | None | 32 (Control) |
| MG-21 (1 µg/ml) | mAb 2C1 (10 µg/ml) | 7* |
| MG-21 (1 µg/ml) | mAb 2C1 (1 µg/ml) | 3* |
| MG-21 (1 µg/ml) | mAb 2C1 (0.1 µg/ml) | 16* |

TABLE XII-continued

INHIBITION OF ADDCC OF mAb MG-21 AGAINST M-2669 CELLS BY mAb 2C1

| Antibody 1 Final Concentration | Antibody 2 Final Concentration | Cytotoxicity[1] % |
|---|---|---|
| MG-21 (1 μg/ml) | mAb 26.8 (10 μg/ml) | 26 |
| MG-21 (1 μg/ml) | mAb 26.8 (1 μg/ml) | 23 |
| MG-21 (1 μg/ml) | P1.17 (10 μg/ml) | 28 |
| MG-21 (1 μg/ml) | P1.17 (1 μg/ml) | 23 |

[1]Cytotoxicity was determined in a 4-hour $^{51}$Cr-release assay using normal human peripheral blood lymphocytes as effectors. The ratio of effector cells to target cells was 100:1. Antibodies alone gave no cytotoxicity and lymphocytes alone gave 6.9% cytotoxicity. Significant differences compared to control without Ab2 were calculated by student's t-test, *, P less than 0.01.

7.2.5. Detection of Anti-MG-21 Antibodies in Patient Sera Using mAb 2C1 as a Probe Since mAb 2C1 is specific for MG-21, it can be used as a reagent for detecting human anti-MS-21 antibodies in the sera of patients treated with MG-21. A competition assay was developed (see Section 7.1.15., supra), by which we tested whether sera from any of 3 patients inJeoted with MG-21 inhibited the binding of MG-21 to mAb 2C1. As shown in Table XIII, sera obtained from all these three patients 17, 18 or 21 days, respeotively, (or later) after administration of MG-21, strongly inhibited the binding of MG-21 to. mAb 2C1 with 20–83%. The pretreatment. sera gave less than 13% inhibition as compared to pooled normal human serum.

TABLE XIII

INHIBITION OF BINDING OF mAb MG-21 TO mAb 2C1 BY SERA FROM PATIENTS RECEIVING mAb MG-21

| Patient No. | Dose of MG-21/day for 7 Days* | Days After Start of mAb Treatment | % Inhibition of Binding 1:2.5** | 1:5 | 1:10 |
|---|---|---|---|---|---|
| 1 | 5 mg/M²/day | 0 | 0 | 0 | 0 |
| | | 14 | 58 | 53 | 33 |
| | | 18 | 60 | 58 | 43 |
| | | 24 | 65 | 62 | 47 |
| | | 28 | 83 | 87 | 85 |
| 2 | 5 mg/M²/day | 0 | 10 | 12 | 0 |
| | | 21 | 55 | 46 | 31 |
| | | 28 | 53 | 32 | 25 |
| | | 49 | 62 | 46 | 20 |
| | | 61 | 59 | 32 | 27 |
| 3 | 50 mg/M²/day | 0 | 6 | 13 | 2 |
| | | 18 | 28 | 21 | 20 |
| | | 28 | 30 | 30 | 26 |
| | | 45 | 45 | 31 | 15 |
| | | 66 | 77 | 60 | 45 |
| | | 127 | 73 | 50 | 43 |

*Patient received 4–6 hour infusion of MG-21 daily for 7 days in dose noted. Serum samples were drawn at various times after the start of treatment.
**Serum samples were diluted 1:2.5, 1:5 and 1:10 in PBS.

The anti-idiotypic mAb antibody 2C1, which we describe here, recognizes an tdiotype specific to a human melanoma-associated GD3 ganglioside antigen. mAb 2C1 was shown to bind to mAb MG-21 even at a low concentration (0.08 μg/ml), but not to other mAb of the same or different isotypes. It inhibited, in a dose-dependent manner, the binding of MG-21 to the GD3 ganglioside antigen as well as to GD3-positive M-2669 melanoma cells. Furthermore, mAb 2C1 completely abrogated the CDC and ADCC activities of mAb MG-21, as long as its concentration was greater than that of MG-21.

Using mAb 2C1 as a probe, we have developed an assay for human anti-MG-21 antibodies in the sera of patients treated with MG-21. Analogous assays may be developed for other types of anti-tumor antibodies. Since human antibodies binding to MG-21 were present at short times (14–21 days) after treatment of patients with MG-21, unless such antibodies are highly effective in inducing an immune response leading to tumor rejection, procedures minimizing such antibody development can be envisioned for use when prolonged treatment of patients by administered anti-tumor antibodies is desired.

8. MONOCLONAL ANTI-IDIOTYPIC ANTIBODIES RELATED TO THE P97 MELANOMA ANTIGEN

We have made monoclonal anti-idiotypic antibodies (Ab2) related to the p97 antigen of human melanoma. This was accomplished by immunizing BALB/c mice with 96.5, a monoclonal antibody (mAb) specific for epitope p97$^a$, hybridizing the mouse spleen cells with NS-1 myeloma cells, and selecting for hybridomas which made antibody that bound to Fab fragments prepared from mAb 96.5 (Fab 96.5). The Ab2 were tested for binding to mAb 96.5 and to mAb defining other epitopes of the p97 antigen, as well as for their ability to inhibit the binding between mAb 96.5 and p97. Three monoclonal Ab2 were identified which competitively inhibited the binding between p97 and mAb 96.5. When injected into either BALB/c or C3H/HeN mice, two of them induced Ab3 which expressed the same idiotype as mAb 96.5 and which were specific for p97. These two Ab2 thus behaved as "internal images" of p97.

8.1. Materials and Methods

8.1.1. Animals

Approximately 6–8 week-old female BALB/c and C3H/HeN mice were used throughout this study.

8.1.2. Human Melanoma Cells

Line SKMEL-28 was used as a source of p97 antigen-positive target cells. Each SK-MEL 28 cell expresses, at its surface, approximately 400,000 molecules of p97.

8.1.3. Mouse Melanoma Cells

Cells from the B16 (C57BL) mouse melanoma, which had been transfected with the p97 gene (Plowman, G. D., 1986, Characterization and expression of the melanotransferrin (p97) gene, Ph.D. dissertation, University of Washington) were used to produce soluble p97 antigen. We also employed a line of cells (2A) from the C3H/HeN mouse melanoma line K-1735-M2 (Fidlet, I. J. and Hart, I. R., 1981, Cancer Res. 41:3266–3267) which, after transfection with the gene for p97, express approximately 10$^6$ p97 molecules per cell. The K-1735-M2 cells, which entirely lack p97, are referred to as parental (par) cells, since the 2A line was derived from them.

8.1.4. Antibodies

Seven mAb to the human melanoma-associated antigen p97 (Brown, J. P., et al., 1981, J. Immunol. 127:1539–546) were used in the study. Three epitopes of p97 have been defined by using these mAb in competitive binding inhibition assays, namely p97$^a$ (by mAb 96.5 and 4.1), p97$^b$ (by mAb 118.1, 133.1, and 133.3), and p97$^c$ (by mAb 8.2 and 133.2). Hybridoma 96.5, which produces a mAb to epitope p97$^a$, was obtained bY fusing spleen cells from an immunized BALB/c mouse with NS-1 myeloma cells (id.). Fab fragments were made from mAb 96.5 by papain digestion and are referred to as Fab 96.5 (id.). mAb F6 is an IgG2a specific for a proteoglycan antigen on human melanoma cells. It was used to prepare Fab fragments (referred to as Fab F6) which were employed as controls.

In order to raise anti-Id, BALB/c mice were injected subcutaneously with 100 μg of purified mAb 96.5 which had been conjugated with keyhole limpet hemocyanin (KLH), and subsequently mixed with Freund's complete adjuvant (Bacto H37Ra, Difco Labs, Detroit, Mich.). One month later, they were injected intraperitoneally with the same amount of KLH-conjugated mAb 96.5 in Freund's incomplete adJuvant (Difco). The mice were subsequently injected with mAb 96.5 in saline at 2-week intervals for 1 or 2 more times. Three days after the last injection, they were killed and a spleen cell suspension was prepared and fused with NS-1 mouse myeloma cells, using standard techniques (Kohler, G. and Milstein, C., 1975, Nature 256:495–497).

8.1.5. Screening of Hybridomas

Primary screening was performed by an ELISA (Kohler, G. and Milsrein, C., 1975, Nature 256:495–497). Fab 96.5, at a concentration of 4 μg/ml in phosphate buffered saline (PBS), were plated onto Immunolon plates (Dynatech Laboratories, Chantilly Va.). The next day, the plates were washed with PBS containing 0.05% Tween 20 and "blocked" by incubation for i hour with PBS containing 0.05% Tween and 1% fetal calf serum (FCS). Supernatants (50 μl) from each well with growing hybridoma cells were added. One hour later, a mixture was.added, containing goat anti-mouse IgG1 (Zymed, San Francisco, Calif.) which had been coupled with horseradish peroxidase (HRP), 0.05% Tween 20, and 1% FCS in PBS. After a 1 hour incubation, antibody binding to the plated Fab 96.5 was detected by adding O-phenylene diamine (OPD) according to the directions of the manufacturer (Zymed). The plates were read in an automatic microplate reader (Genetic Systems Corporation, Seattle, Wash.) at an absorbance of 492 nm;/630 nm. Fab fragments from mAb F6 were employed as controls, and only those hybridomas which made mAb that bound to Fab 96.5, but not to Fab F6, were retained for further testing. The employed screening procedures detected only hybridomas making IgG1 antibodies.

To further test supernatants for activity, an assay was used in which the supernatants were diluted two-fold, combined with one part of mAb 96.5, and added to Immunolon wells onto which Fab 96.5 had been plated. After addition of goat anti-mouse IgG and OPD, the ability of the added mAb 96.5 to prevent binding of the supernatants to the plated Fab was assessed. This assay was also employed to test anti-Id for binding to mAb defining p97 epitopes other than $p97^a$.

Hybridomas which made antibodies binding to Fab 96.5 but not to Fab F6 were cloned twice by limiting dilution, after which they were expanded and injected into pristane-primed BALB/c mice for ascites production.

8.1.6. Studies on Purified Anti-Idiotypic Antibodies

Ab2 were purified by precipitation with saturated ammonium sulfate (Mishell, B. and Shiigi, S., 1979, in Select Methods in Cellular Immunology, W. H. Freemen & Co., pp. 278–281). To identify anti-Id which could interfere with the binding of mAb 96.5 to p97, SKMEL-28 melanoma cells were plated at $10^4$ cells/well. Purified Ab2 were mixed with mAb 96.5 (1 μg/ml). Inhibition of binding of mAb 96.5 to the melanoma cells was detected by adding a goat anti-mouse HRP conjugate as abovel a few tests of this type were also performed on hybridoma supernatants.

To study whether the purified Ab2 could block the antigen binding site of Fab 96.5, various concentrations of Ab2 were added to wells of Immunolon plates onto which Fab 96.5 had been plated. p97 antigen isolated from transfected B16 mouse melanoma cells was radioiodinated (Rose, T. M., et al., 1986, Proc. Natl. Acad. Sci. U.S.A. 83:1261–1265), $2 \times 10^5$ cpm of labelled p97 were added, and the number of counts bound per well was determined.

8.1.7. Competition of Radiolabelled P97 for Binding to Fab Fragments of mAb 96.5

Various concentrations of purified Ab2 were mixed with a constant amount of $^{125}$I-labelled p97 antigen, and the mixtures were added to plates which had been coated with Fab 96.5. After one hour, the plates were washed, 2 N NaOH was added, and the contents of the wells were counted in a gamma counter.

8.1.8. Searches For AB3 In Vivo

BALB/c and C3H/HeN female mice, 6–8 weeks old, were injected intraperitoneally (j.p.) with 50 μg of Ab2 conjugated to KLH and mixed with complete adJuvant. Five days later, they were boosted by an injection of Ab2 in incomplete adJuvant and subsequently injected with Ab2 in saline at 5-day intervals. After a total of 4 and 6 immunizations, respectively, the mice were bled. They continued to be boosted at 2-week intervals for several weeks. In some cases, the immunization protocol was initiated at 2-week intervals with 4–5 boosts.

Sera from the immunized mice were titered for the presence of antibodies binding to Ab2 and referred to as Ab3. This was done by mixing diluted sera with Ab2, and adding the mixture onto Immunolon plates which had been coated with Fab 96.5 (as Ab1), after which goat anti-mouse IgG1-HRP and OPD were added. Data were expressed as percent inhibition of the binding of Ab2 to Ab1. They were calculated by determining the O.D. (optical density) value for (Ab3+Ab2), dividing it by the O.D. value for Ab2 alone, and subtracting the quotient from 100.

The sera were also tested for Ab3 binding to the p97 antigen. Purified p97 was plated onto Immunolon plates at 5 ug/ml in PBS and left overnight. After blocking, diluted sera were added, followed by a goat antiserum to mouse immunoglobulin which reacted with IgG, IgM, and IgA, and was coupled to HRP.

A solid phase inhibition assay was also employed, in which the mouse sera were mixed with 2A mouse melanoma cells which express p97 at the cell surface, or with par mouse melanoma cells, which do not. The mixture was first incubated for i hour and then added to Immunolon plates coated with the p97 antigen. As above, binding was detected by adding OPD in the presences of anti-mouse-HRP conjugates.

8.2. Results 8.2.1. Generation Of Ab2 Binding To Idiotypic Determinants On mAb 96.5

BALB/c mice were immunized with mAb 96.5, their spleen cells fused, and hybridoma supernatants screened for IgG1 antibodies to mAb 96.5, as described supra. Approximately 3,000 hybridomas were obtained from 8 different fusions. Supernatants from 70 of these hybridomas were found to bind to Fab 96.5 and not to the control Fab F6; most of the hybridomas from which they were derived, therefore, were presumed to make Ab2. Seven of these hybridomas were cloned, and the mAb which they made were purified and tested for binding to Fab 96.5. As shown in FIG. 11, mAb made by all the seven hybridomas bound to Fab 96.5, although there was variation between Ab2 in the binding values observed at high antibody concentration. None of the mAb bound to Fab F6.

8.2.2. Tests on Ab2 Specificity For The Antigen-Binding Site Of mAb 96.5

We investigated whether any of the seven Ab2 on which data are presented in FIG. 11 identified the antigen-binding site of mAb 96.5. First, we measured the ability of the mAb to inhibit the binding of mAb 96.5 to the p97 antigen expressed by SK MEL-28 cells; this was carried out as described in Section 8.1.6. Three of the seven Ab2, #3, #5 and #7, strongly inhibited this binding, while two Ab2 (#4 and #6) gave a weak inhibition, and two Ab2 (#1 and #2) gave no inhibition (FIG. 12).

Second, we studied the ability of the seven Ab2 to compete with soluble p97 for binding to mAb 96.5. Various dilutions of each Ab2 were mixed with radioiodinated p97, and the binding of p97 to Fab 96.5 was determined in a solid phase assay (FIG. 13). Anti-Id #3, #5, and #7 competed with radioiodinated p97 while the four other anti-Id (#1, #2, #4, #6) did not compete. The results were thus similar to those presented in FIG. 12.

Third, we demonstrated that the same three Ab2 with the ability to compete with p97, namely #3, #5, and #7, can block the antigen-binding sites of Fab 96.5 so as to decrease 50–60% of the binding of radioiodinated p97 to Fab 96.5 (FIG. 14). One Ab2, #2, gave 25% inhibition of this binding, and the remaining three Ab2 (#1, #4, #6) gave 0–10% inhibition.

The data thus suggested that three Ab2, #3, #5, and #7, were capable of mimicking the p97$^a$ epitope as an "internal image". However, the possibility still existed that steric hindrance was responsible for the observed effects. We therefore tested the ability of the Ab2 to induce an Ab3 response in vivo, as described in Section 8.2.4, infra.

8.2.3. Analysis of the Binding of Ab2 to a Series of mAb Which Specify p97 Epitopoes Other Than p97$^a$ Seven mAb to p97 were selected for study. According to assays measuring competitive inhibition of mAb binding to p97-positive cells, the seven mAb identify three different epitopes on the p97 antigen (Brown, J. P., et al., 1981, J. Immunol. 127:53–546), namely p97$^a$ (mAb 4.1 and mAb 96.5), p97$^b$ (mAb 118.1, mAb 133.1, mAb 133.3, and mAb 8.2) and p97$^c$ (mAb 133.2). mAb 133.3 is an IgG2b, mAb 4.1 and 8.2 are IgG1, and the other mAb are IgG2a, except 4.1 and 8.2 which are IgG21.

In the experiment presented in FIG. 15, each of the 5 IgG2a mAb were mixed with the Ab2 to be tested, and added to plates coated with Fab 96.5, followed by addition of goat anti-mouse IgG1-HRP to detect the binding of the respective Ab2 to Fab 96.5. As shown in FIG. 15, mAb 133.3 inhibited the binding of six of the tested Ab2 (#1, #3, #4, #5, #6, and #7) to Fab 96.5 (FIG. 13); the inhibition was of approximately the same degree as that seen with mAb 96.5. The binding of #2, which like the other Ab2 had been selected for binding to mAb 96.5, was not inhibited. mAb 118.1, 133.1, and 133.2 did not inhibit the binding of any of the tested Ab2.

A different assay was used to analyze the degree of binding between the Ab2 and various anti-p97 mAb of the IgG1 isotype, and the effect of any such binding upon the subsequent binding of radiolabelled p97 by the anti-p97 mAb. The two IgG1 anti-p97 mAb, 4.1 and 8.2, were tested, as was mAb 96.5. Each Ab2 was plated, various concentrations of mAb 8.2, ; 4.1, or Ab 96.5 were added, and the binding of the anti-p97 mAb to radioiodinated p97 was measured (FIG. 16). Three Ab2, #3, #5, and #7, interfered with the binding of mAb 96.5 to p97 (in agreement with the results described in Section 8.2.2, supra), while four other Ab2, #1, #2, #4, and #6, did not interfere. None of the Ab2 bound to mAb 8.2 or mAb 4.1. The experiment was repeated, testing mAb 133.1 and mAb 133.3 in parallel with mAb 96.5, since the data presented in FIG. 15 showed that mAb 133.3 (but not 133.1) could bind to Ab2. FIG. 17 shows that all of the seven Ab2 tested bound to both mAb 96.5 and 133.3. In contrast, none of the Ab2 bound to mAb 133.1.

An assay was performed which demonstrated that six of the Ab2 (with the exception of #2) prevented mAb 133.3 from binding to SK MEL-2S melanoma cells. In addition, none of the Ab2 could inhibit mAb 4.1 or 8.2 from binding to SKMEL-28 cells. None of the seren Ab2 bound to P1.17, an IgG2a myeloma protein, or to the two mAb used as controls, L6 (an IgG2a anti-carcinoma antibody) or MPG24 (an IgG2a antibody to a melanoma-associated proteoglycan), or to a goat antiserum to mouse IgG2b (Table XIV).

TABLE XIV mAb 96.5 INHIBITS THE BINDING OF SOME Ab2 TO Fab 96.5*

| Ab2 Number | Inhibitor | | | | | |
| --- | --- | --- | --- | --- | --- | --- |
| | PBS | 96.5 | P1.17 | MPG24 | L6 | Goat Anti-Mouse IgG2b |
| #1 | 0.961 | 0.125 | 0.941 | 0.993 | 0.876 | 1.026 |
| #2 | 1.074 | 0.514 | 0.942 | 1.064 | 0.953 | 1.049 |
| #3 | 0.655 | 0.084 | 0.586 | 0.618 | 0.567 | 0.623 |
| #4 | 0.649 | 0.066 | 0.629 | 0.674 | 0.611 | 0.743 |
| #5 | 0.555 | 0.061 | 0.521 | 0.557 | 0.506 | 0.541 |
| #6 | 0.447 | 0.091 | 0.436 | 0.443 | 0.418 | 0.551 |
| #7 | 0.554 | 0.074 | 0.515 | 0.577 | 0.504 | 0.627 |

*As detected by an ELISA, in which various inhibitors at 80 µg/ml were mixed with Ab2 (0.4 µg/ml) and added to plates coated with Fab 96.5. HRP-conjugated goat anti-mouse IgG1 was added to the plates and incubated for 1 hour, followed by addition of OPD. OD was measured at 492 nm.

Taken together, our findings indicate that the seven Ab2 tested could bind to mAb 133.3, perhaps at its antigen-binding site, with the exception of #2 which does not bind to mAb 133.3 at its antigen-binding site. (#2 does however bind to mAb 133.3, apparently at other than its antigen-binding site; see FIG. 17.)

8.2.4. Induction of an Ab3 Response

The seven Ab2 were tested for their ability to induce an Ab3 antibody response in mice. In the first sets of experiments, syngeneic (BALB/c) mice were immunized with Ab2. For most of these experiments, the Ab2 were conjugated with KLH.

After the immunization with Ab2, sera of the mice were tested for the presence of Ab3 detectable by its ability to bind to Ab2. Several dilutions of the mouse sera were mixed with the respective Ab2, and added to immunolon plates coated with Fab 96.5 (as Ab1). Goat anti-mouse IgG1-HRP was then used to detect the binding of the Ab2 to the Fab 96.5 (Table XV).

TABLE XV

INHIBITION OF THE BINDING OF Ab2 TO Fab 96.5 (AS Ab1) BY SERA FROM BALB/c MICE WHICH HAD BEEN INJECTED WITH THE RESPECTIVE Ab2*

| Ab2 Number | % Inhibition | |
|---|---|---|
| | 1st Bleeding | 2nd Bleeding |
| #1 | 90 | 96 |
| | 100 | 99 |
| #2 | 96 | 97 |
| | 95 | 98 |
| #3 | 85 | 100 |
| | 83 | 98 |
| #4 | 82 | 96 |
| | 86 | 87 |
| #5 | 74 | 92 |
| | 75 | 94 |
| #6 | 0 | 89 |
| | 25 | 50 |
| #7 | 73 | 91 |
| | 77 | 92 |

*Sera were diluted 1:10. The respective Ab2 was conjugated to KLH prior to injection into mice. Data are given for each of 2 mice/group and for 2 subsequent bleedings of the mice.

As shown in Table XV, serum derived solely from the first bleeding inhibited the binding of Ab2 to Fab 96.5. The amount of inhibitory activity increased after a second boost.

We next tested whether sera from the immunized mice could bind to p97 (like an Ab1). Soluble p97 antigen was plated, and diluted mouse sera added (after blocking), followed by goat anti-mouse IgG-HRP. Sera from mice immunized with either of two Ab2, #3 or #7, bound to p97, while sera from mice immunized with any of the other five Ab2, including #5, did not bind to p97 (FIG. 18). As a positive control, we titrated the binding to p97 of either mAJ3 96.5 or a mouse anti-p97 serum, and compared the binding observed with that seen using sera from mice immunized with either Ab2 #3 or #5. The data showed that the latter sera contained p97-specific Ab3 in a concentration of approximately 1–5 µg/ml. The ability of Ab2 #3 or #7 to induce an Ab1-like Ab3 response thus indicated that these Ab2 were internal image antibodies.

To further test the specificity of the Ab3 for p97, sera from Ab2-immunized mice were absorbed with 1×10⁶ cells from either the p97-positive mouse melanoma line 2A or from its p97-negative parent (as a control), before the sera were added to p97 which had been coated onto plates. The binding of the Ab3 to p97 was then detected by using a goat antimouse IgG-PLRP conjugate. As shown in FIG. 19 (Panels A and B), sera from mice immunized with either Ab2 #3 or #7 contained Ab3 which bound to p97, and this Ab3 activity was removed by absorption with 2A cells but not by absorption with par cells. There was a lower amount of binding to p97 with sera from mice immunized with either Ab2 #4 or #5, and this binding was also inhibited by absorption with 2A cells (FIG. 19, Panels C and D). Neither normal mouse serum nor serum from mice immunized with P1.17 (as a control) contained antibodies which bound to p97. While the binding of purified mAb 96.5 to p97 could be completely abrogated by absorption with 2A cells (FIG. 20), the binding of serum antibodies from mice immunized with p97 was only partially inhibited, as was the Ab3 activity of sera from mice immunized with either Ab2 #3 or #7.

An Ab3 response was also detected in C3H/HeN mice after immunization with Ab2 conjugated to KLH. Serum from the immunized C3H/HeN mice bound to soluble p97 antigen in a solid phase ELISA (FIGS. 21, 22). Absorption of the mouse sera with either 2A or par cells before they were tested for binding to soluble p97 verified that the binding was to p97.

Experiments were also done in which BALB/c and C3H/HeN mice were immunized with an Ab2 which had not been conjugated to KLH. Sera of these mice were found to contain antibodies which bound to Fab 96.5. To determine whether these antibodies were Ab2 which still remained in the circulation, or whether any Ab4 had been induced, an ELISA was performed with HRP conjugates which could identify not only IgG1 (the isotype of the Ab2), but also IgG2b and IgG3. The findings suggested that the mouse sera contained Ab4 which could bind to AB1 and belonged to the IgG2b and IgG3 classes.

8.3. Discussion

We have made a series of mouse mAb to idiotypic determinants on mAb 96.5, which defines p97$^a$, an epitope of the p97 melanoma antigen, and have analyzed them with respect to specificity and ability to induce an Ab3 response in mice. Seven Ab2 were studied in some detail. Four of these Ab2 did not appear to identify the region of mAb 96.5 involved in binding p97, since they neither appreciably inhibited the binding between mAb 96.5 and p97, nor was their binding to mAb 96.5 inhibited by soluble p97. However, three of the Ab2, referred to as #3, #5, and #7, respectively, prevented the binding between soluble p97 antigen and mAb 96.5, and soluble p97 prevented the binding between Fab 96.5 and these Ab2.

mAb 133.3 behaved similarly to mAb 96.5 when tested in binding assays with the seven Ab2, while mAb 4.1 did not. This was unexpected, since mAb 133.3 has been reported to identify a different epitope (p97$^b$) than mAb 96.5, while mAb 4.1 has been reported to be specific for the same epitope (p97$^a$) (Brown, J. P., et al., 1981, J. Immunol. 127:539–546) as mAb 96.5. The reasons for the discrepancy between results obtained using an assay for competitive inhibition of mAb binding to target cells (id.), and our findings, obtained with an assay measuring the binding between AB1 and Ab2, are unknown.

The antigen binding inhibition data were consistent with the view that three of our Ab2, #3, #5, and #7, were of the "internal image" type. The data did not, however, exclude alternative explanations such as steric hindrance. We therefore investigated whether any of these three Ab2 could induce an immune response in mice. Since humoral antibody responses can generally be studied more easily and precisely than cell-mediated responses, we searched for Ab3 which could bind to p97.

Two Ab2, #3 and #7, induced an Ab1-like Ab3 response in both BALB/c and C3H/HeN mice, thus indicating that they are internal image antibodies. A third Ab2, #5, whose behavior was similar to #3 and #7 when tested in vitro, did not induce an Ab1-like Ab3 response. The binding of the Ab3 to p97 was competitively inhibited by absorption with 2A cells, which express p97, but not with cells from the p97-negative par line. The fact that a response was also observed in the allogeneic C3H/HeN strain indicates that the response was not controlled by Th genes, but more likely induced by the Ab2 acting as an "internal image" of the p97 antigen (Lee, V. K., et al., 1986, Blochim. Biophys. Acta 865:127–139).

To obtain solely an Ab1-like response in vivo, the conjugation of an Ab2 to KLH was necessary. When KLH was not used, the sera of the immunized mice contained both antibodies of th& IgG1 isotype of the Ab2 and antibodies which were of other isotypes (IgG2b, IgG3), and which may have been Ab4. If Ab4 were, indeed, generated, an Ab3 response may have occurred at some point.

9. ANTI-IDIOTYPIC ANTIBODIES SPECIFIC FOR ANTI-CARCINOMA ANTIBODY L6

Murine monoclonal antibody (mAb) L6 (Ab1) is an IgG2a specific for a tumor-associated carbohydrate antigen which is found at the surface of cells from many different human carcinomas (Hellstrom, I., et al., 1986, Cancer Res.. 3917–3923). Anti-idiotypic mAb (Ab2) against L6 have been made. Twenty-four Ab2 were obtained which bound to Fab fragments prepared from L6 but not to Fab prepared from a control IgG2a. Eight of these 24 mAb could bind at high concentrations to one of two mAb which were independently derived but have the same specificity as L6. Fourteen of the 24 Ab2 could inhibit the binding of L6 to antigen on cells. Six of these 14 Ab2 were unable to bind to Fab fragments prepared from L6 and already bound to L6 antigen-positive cells. Using cloned variable region gene segments, it was found that two of these 6 Ab2 could specifically recognize the L6 heavy chain variable region associated with an irrelevant light chain, while the remaining 4 recognize a combinatorial determinant, requiring L6 heavy and light chain variable regions to be associated. In contrast, all of S tested Ab2 which bound to L6 Fab attached to cells, could also bind to the isolated light chain variable region. The 6 Ab2 which did not bind to L6 Fab fragments attached to cells were injected into BALB/c and C3H/HeN mice. Two of them (possibly more) induced polyclonal antibodies (Ab3) which expressed the same idiotype as L6, bound to L6-positive tumor cells and competed with L6 for its antigen-binding site.

9.1. Materials and Methods

9.1.1. Animals

Six-to-eight week old BALB/c and C3H/HeN female mice were obtained from the Animal Facilities at the Fred Hutchinson Cancer Research Center. They were used throughout the study unless otherwise indicated.

9.1.2. Cell Lines

Human colon carcinoma line H-3347 (Hellstrom, I., et al., 1986, Proc. Natl. Acad. Sci. U.S.A. 83:7059–7063) expresses high levels of the antigen defined by L6. The CEM human T cell line, which does not bind L6, was included as a negative control.

9.1.3. Antitumor Antibodies ("AB1")

Monoclonal antibody L6 (IgG2a) was employed as the antitumor mAb (Ab1) in this study. Its development and characterization is described elsewhere (Hellstrom, I., et al., 1986, Cancer Res. 46:3917–3923; Hellstrom, I., et al., 1986, Proc. Natl. Acad. Sol. U.S.A. 83:7059–7063). mAb F26 (IgG1) and 012/28–24 (IgG2a) are made by hybridomas which resulted from the fusion of spleen cells from BALB/c mice immunized with carcinoma tissue; hybridization and selection was similar to that resulting in L6. The latter two mAb compete with L6 for binding to carcinoma cells. mAb 96.5 (Brown, J. P., et al., 1981, J. Immunol. 127:539–546) and myeloma protein P1.17 (American Type Culture Collection Accession No. TIB 10), which are both IgG2a, were used as controls. Fab fragments were made from L6 and 96.5 by papain digestion (id.), and are termed Fab L6 and Fab 96.5, respectively.

9.1.4. Generation of Anti-Idiotypic Antibodies (AB2)

A protocol was used which had been successfully employed to generate Ab2 relating to a different tumor antigen, p97 (see Section 8, supra). BALB/c mice were immunized with 100 μg of L6 which had been coupled to keyhole limpet hemocyanin (KLH) as described (Streicher, H. Z., et al., 1986, J. Immunol. 136:1007–1014). The first immunization was given subcutaneously in complete H37Ra adjuvant (Difco, Detroit, Mich.), and a second dose was given in incomplete Freund's adjuvant intraperitoneally (i.p.) 4 weeks later. Two to four subsequent immunizations were done i.p. in saline at two-week intervals.

Spleens were removed 3 days after the last boost, and the spleen cells were fused with NS-1 myeloma cells by centrifugation with polyethylene glycol. After 10 days, the hybridomas were screened by an ELISA against Fab fragments which had been prepared from L6 (referred to as L6 Fab) and were coated onto 96-well Immunolon II plates (Dynatech, Chantlily, Va.). The binding to L6 Fab was detected by separately using each of three different reagents: a rabbit antiserum to mouse IgG1 which had been coupled to horseradish peroxidase (HRP) (referred to as IgG1-HRP), a HRP-conjugated rabbit antiserum to mouse IgG3 (referred to as anti-mouse IgG3-HRP), or protein A coupled to HRP ("protein A-HRP"); these reagents were obtained from Zymed (South San Francisco, Calif.). Antibodies binding to Fab L6 were tested for binding to Fab 96.5 to exclude nonspecific binders. Hybridomas appearing to produce mAb to the idiotype of L6 were cloned twice by limited dilution, followed by testing of all subclones.

9.1.5 ; AB2 Purification

Four-to-six week old male BALB/c mice were primed with pristane. Ten days later, they were injected with $5 \times 10^6$ Ab2-producing hybridoma cells and ascites was collected 3 to 8 weeks subsequently. Ascites containing IgG2a and IgG2b antibodies was purified over protein A columns (Brown, J. P., et al., 1981, J. Immunol. 127:539–546), and IgG1-containing ascites was purified by ammonium sulfate precipitation, followed by DEAE-Sephacel (Pharmacia, Uppsale, Sweden) chromatography. Purified Ab2 were tested for binding to Fab L6 as well as for inhibition of the binding of L6 to H-3347 cells (as described below).

9.1.6. Inhibition Assay to Detect AB2 Binding to the Paratope Region of L6

An assay was used similar to one previously employed in the p97 system (see Section 8,supra). Supernatants containing Ab2, or purified Ab2 were mixed with mAb L6 for a final concentration of 0.1–0.4 μg/L6 per ml. The mixture was incubated in a 96-well tissue culture plate (Falcon, Beoton Dickinson, Oxnard, Calif.) for 30 minutes at room temperature, after which it was added to glutaraldehyde-fixed H-3347 carcinoma cells which had been attached to the wells of a 96-well plate. Binding of L6 to the H-3347 cells was detected by an ELISA using a goat antiserum to mouse IgG coupled to HRP, or protein A coupled to HRP. Data were expressed as percent inhibition of the binding of L6 to the cells in the presence of the Ab2.

9.1.7. Blocking Assay to Detect Competition Between AB2 and Antigen for L6 Binding Sites Thirty μg/ml of Fab L6 were added to $5 \times 10^5$ H-3347 carcinoma cells in a propylene tube. After a 30 minute incubation at 4° C., the cells were washed to remove any unbound Fab. Purified Ab2 were labelled with flourescein isothiocyanate (FITC). Various concentrations of the labelled Ab2 were added to the propylene tube, followed by incubation at 4° C. for 30 minutes and washing. Ab2 binding was detected using an EPIC-C model flourescein-activated cell sorter (FACe), as previously described (Hellstrom, I., et al., 1986, Cancer Res. 46:3917–3923). This experiment was also performed with phycoerythrin (PE) labelled L6 instead of unlabelled L6 Fab fragments.

9.1.8. Clonging of L6 Heavy and Light Chain Variable Region Gene Segments

DNA was isolated as described in principle by Blin and Stafford (1976, Nucl. Acids Res. 3:2303–2308) and in more detail by Ledbetter et al. (1987, Mol. Immunol. 24:1255–1261). It was digested with either EcoRI or HindIII and size fractionated on sucrose gradients (Maniatie, T., et al., 1982, Molecular Cloning, A Laboratory Manual, Cold Spring Harbor Laboratory, N.Y.). Gradient fractions containing specific variable (V) regions were identified by Southern blot analysis (Southern, E. M., 1975, J. Mol. Biol. 98:503–507). The expressed alleles were identified by virtue of their lack of detection in Southern Blot analysis of non-producing L6 sublines. EcORI-digested DNA containing the expressed L6 heavy chain V region gene segment was cloned into the EMBL3 lambda phage vector (Promega Biotech, Madison, Wis.) with Gigapack packaging extracts (Stratagene, La Jolla, Calif.), plated, and screened using an XbaI/EcoRI fragment containing the murine heavy chain enhancer.

A 2.3 kb HindIII fragment spanning the murine heavy chain enhancer was cloned into a pSV2-gpt vector (Mulligan, R. C. and Berg, P., 1980, Science 209:1422–1427) containing the human C exons as a 10.5 kb Ba.mHI fragment derived from the HG3A phage clone (Ellison, J. W., et al., 1982, Nucl. Acids Res. 10:4071–4079). The expressed variable heavy chain gene segment was then transferred into the vector as a 10.5 kb EcoRI fragment.

Gradient fractions containing HindIII-digested DNA with the expressed L6 light chain were cloned into the XbaI site of Lambda Zap (Stratagene) by filling in the HindIII overhangs with the dinucleotide AG and the XbaI overhangs with CT thus leaving compatible overhangs for cloning. The resulting library was screened with a I kb PstI/HindIII fragment from the intron separating JK and CK in the pBR322 clone containing the 9.5 kb BamHI fragment with the expressed K gene from MPC11 (Kelley, D. E., et al., 1982, Cell 29:681–689). For the chimerio light chain expression construct, a 1 kb HindIII/XmnI fragment containing the murine K enhancer (from MPC11) was cloned upstream of a 2.7 kb EcoRI fragment encoding the human CK exon (Heiter, P. A., et al., 1982, J. Biol. Chem. 257:1516–1522) in a pUC-gpt vector. The expressed L6 VK gene segment was then transferred into this vector as an EcoRI-NotRI fragment linkered into the unique PstI site.

The chimerio light chain and heavy chain gene constructs were transfected into the mouse myelcma cell line Ag 8.653 using a BioRad electroporator per the manufacturer's instructions, with subsequent selection on 0.5 μg/ml mycophenolic acid. Similar transfections were performed using only the chimerio light chain gene construct and the SP2/0 mouse myeloma cell line, or with the chimerio heavy chain construct and the JSSSL murine myeloma which expresses a murine lambda I light chain. Cell lines expressing the chimerio proteins were identified by ELISA. Chimerio L6 antibody was purified over protein A-Sepharose and biotinylated as described previously (Pohlit, H. M., et al., 1979, in Immunological Methods, I. Lefkovits and B. Pernis, eds., Academic Press, New York, pp. 181–194).

9.1.9. Assays For L6 Anti-Idiotype Variable Region Specificity

Competition assays were performed by coating Immulon II plates with 100 μl of rat anti-mouse kappa chain mAb 187.1 (provided by Dr. Dale Yelton, Oncogen), followed by three washes, and then supernatant from cultures of the L6 anti-idiotypic mAb. The plates were then washed-again, and 100 μl of unlabelled competitor was added at a concentration of 6 μg/ml. The unlabelled competitors were either culture supernatants. from transfectants expressing the L6 chimeric variable heavy chain associated with the J558L light chains, or the L6 chimetic variable light chain only, or media spiked with purified chimeric L6 mAb or PW P3281BS (a control, irrelevant human IgG1 antibody). After 30 minutes at 37° C., 50 μl of a 1 μg/ml solution of purified, biotinylated, chimetic L6 antibody was added to the. 100 μl volume already present in the well. This was allowed to incubate for an additional hour at 37° C., then the plate was washed, incubated with Avidin-HRP (TAGO, Burlingame, Calif.).(1:1000 dilution for 30 minutes at room temperature), washed again, and developed with TMB chromogen in buffered substrate (Genetics Systems, Seattle, Wash.). The data was expressed as % inhibition, with no competitor (media only) taken to be 100% with the background value (no Ab2) subtracted.

9.1.10. Induction of an AB3 Response

Six-to-eight week old BALB/c and C3H/HeN females were immunized with 50 μg Ab2 which had been conjugated with KLH (Streicher, H. Z., et al., 1986, J. Immunol. 136:1007–1014) A similar second immunization was done one week after the first one, followed by a third and fourth immunization performed at 1-week intervals with the Ab2 given in phosphate buffered saline (PBS), and subsequent immunizations were done at 2-week intervals with the Ab2 in PBS. All immunizations were done i.p. After 4 weeks, the mice were bled periodically and their sera were tested for the presence of (polyclonal) Ab3.

9.1.11. Purification of Polyclonal AB3

Sera from mice immunized with Ab2 were collected between 6 and 20 weeks after the first immunization and pooled. Ten mg of the respective Ab2 were conjugated to 1 ml of cyanogen. bromide-activated Sepharose 4B (Pharmacia, Piscataway, N.J.), and chromatography was done according to the manufacturer's instructions, so as to enrich for Ab3 which could bind to the respective Ab2.

9.1.12. Measurement of the Ability of AB3 to Inhibit the Binding of AB2 to L6 Fab A previously described assay was used (see Section S, supra). Sera or purified Ab3 to be tested for Ab3 were mixed with a fixed concentration (2.0 μg/ml) of purified Ab2 and added to an Immunolon II plate whose wells had been coated with Fab L6; mAb L6 and PBS were used as positive and negative controls, respectively. Following 30 minutes of incubation, the binding of Ab2 to Fab L6 was detected by an ELISA using a rabbit anti-mouse IgG1 HRP/protein A-HRP cocktail. Data were expressed as percent inhibition of the binding of Ab2 to Fab L6 by the Ab3 serum.

9.1.13. Assay for Binding of AB3 to Cells

Various dilutions of mouse serum to be tested for Ab3 or purified polyclonal Ab3 (in 50 μl amounts) were incubated at 4° C. with $5 \times 10^5$ H-3347 cells for 30 minutes in polypropylene tubes. Culture medium, serum from mice immunized with mAb 96.5 or with P1.17, and normal mouse serum were used as negative conbrols. Cells were washed twice in media. Binding of Ab3 to target cells was detected by a goat antimouse IgG labelled with FITC (Tago, Burlingame, Calif.); 50 μl was added to the mixture of mouse serum and tumor cells and incubated for 30 minutes. After washing twice in media, the cells were analyzed using FACS. CEM cells, which do not express the antigen defined by L6, were used as a negative target cell control.

9.2 Results

9.2.1. Generation of Anti-Idiotypic mAb (AB2) to L6 (AB1)

Hybridomas producing anti-idiotypic mAb were obtained immunizing RALB/c mice with L6 and fusing their spleen cells with myeloma NS-1, followed by screening of the hybridoma supernatants for binding to Fab L6. Cells from wells with supernatants binding to Fab L6 were cloned twice and the clones tested for their ability to make mAb binding to Fab L6 and not to Fab 96.5 (used as a negative control). From 8 fusions, 24 hybridomas which made mAb to Fab L6 were isolated, stabilized and used for ascites production; they represented several different isotypes (Table XVI).

TABLE XVI

ANTI-IDIOTYPIC mAb TO mAb L6

| Anti-idiotypic hybridoma | Anti-idiotypic mAb (Ab2) | Binding to paratope region of L6* | Isotype |
| --- | --- | --- | --- |
| 4/1-6-1 | L6 anti-Id 1 | Yes | IgG2b |
| 4/2-4-1 | L6 anti-Id 2 | Yes | IgG2b |
| 4/3-2-1 | L6 anti-Id 3 | Yes | IgG2a |
| 4/5-1-1 | L6 anti-Id 4 | Yes | IgG2b |
| 5/4-2-2 | L6 anti-Id 5 | No | IgG3 |
| 6/14-2-2 | L6 anti-Id 6 | Yes | IgG1 |
| 6/13-3-1 | L6 anti-Id 7 | Yes | IgG1 |
| 6/20-4-5 | L6 anti-Id 8 | Yes | IgG1 |
| 7/10-2-3 | L6 anti-Id 9 | Yes | IgG1 |
| 5/14-2-6 | L6 anti-Id 10 | Yes | IgG1 |
| 5/15-3-1 | L6 anti-Id 11 | Yes | IgG1 |
| 10/24-1-5 | L6 anti-Id 12 | Yes | IgG1 |
| 10/20-2-3-1 | L6 anti-Id 13 | Yes | IgG1 |
| 11/48-3-14 | L6 anti-Id 14 | Yes | IgG1 |
| 11/75-1-3 | L6 anti-Id 15 | Yes | IgG2a |
| 11/81-1-2 | L6 anti-Id 16 | No | IgM |
| 11/80-3-8 | L6 anti-Id 17 | No | IgM |
| 10/30-1-6-28 | L6 anti-Id 18 | No | IgG3 |
| 10/36-1-1 | L6 anti-Id 19 | No | IgG3 |
| 11/5-31-2-4 | L6 anti-Id 21 | No | IgG3 |
| 11/26/2-4 | L6 anti-Id 22 | No | IgG3 |
| 11/27-5-5-4 | L6 anti-Id 23 | No | IgG3 |
| 9/66-11-2 | L6 anti-Id 24 | No | IgG3 |
| 10/46-6-4 | L6 anti-Id 25 | No | IgG3 |

*Defined as the ability to inhibit mAb L6 from binding to its target antigen on H-3347 carcinoma cells.

Ab2 purified from the ascites was used for further testing (see below).

9.2.2. Characterization of AB2 Binding to Idiotopes on L6

An initial screening identified 14 of 24 hybridomas tested which made Ab2 inhibiting 90–100% of the binding of L6 (tested at 0.2–0.4 μg/ml) to carcinoma cells and were further tested for the ability to inhibit the binding of L6 to its target antigen on cells. Such inhibition is expected to occur if the Ab2 reacts with the idiotope region of L6. An ELISA was used for this purpose, utilizing glutaraldehydefixed H-3347 cells as a source of antigen. As shown in FIG. 23, the binding of L6 (0.2 μg/ml) to carcinoma cells was inhibited when Ab2 was added at a concentration of 0.5 μg/ml and 5 μg/ml. Two of the inhibiting Ab2 were IgG2a, 3 were IgG2b, and the remaining 9 were IgG1, while none of 7 IgG3 or 2 IgM antibodies was inhibitory.

The 14 Ab2 which could inhibit the binding of L6 in the above-described solid-phase assay were labelled with FITC for analysis. Each conjugate was analyzed by an ELISA for the ability to bind to Fab L6 as well as the ability to prevent L6 from binding to antigen-positive carcinoma cells. This was done to ascertain that the labelled antibodies behaved exactly like unlabelled antibodies. When the FITC-labelled Ab2 were added to the Fab L6, which had been added in a saturation dose, to H-3347 carcinomas cells, it was found that 8 of the 14 Ab2 could still bind to the Fab L6, while the binding of 6 Ab2 was completely inhibited (FIG. 24). When PE-labelled L6 was used instead of Fab L6 in this assay, it was found that the L6 remained bound to the cells and was not displaced in the presence of the 6 non-binding Ab2 (FIG. 25).

The 6 Ab2 which inhibited the binding of L6 to its target antigen, and which were unable to bind to previously bound Fab L6 or cells, were selected for further testing. The studies reported in the following sections were performed on samples of these 6 Ab2 and primarily aimed to identify Ab2 capable of acting as "internal images" of the LS-defined antigen.

9.2.3. Specificity of the L6-Generated AB2

There are two mAb, F2-6 and 012/28214, which have the same specificity as L6 when tested on the FACS in competitive binding inhibition assays. Samples of these two mAb were mixed with various concentrations of Ab2 to test whether the latter could inhibit the binding of the two ("L6-look-alike") mAb to carcinoma cells. None of the 14 Ab2 tested inhibited the binding of 012/28-24 to the L6-defined antigen, when assayed similarly as shown for L6 in FIG. 26. Eight of the fourteen Ab2 tested could inhibit binding of F26 at high concentrations, 20 to 200 μg/ml inhibiting 1 μg/ml of F26. This suggests that 012/28-24 has a different idiotype from that of LS, and that F26 and L6 may have overlapping idiotopes.

9.2.4. AB2 Epitope Specificity

The epitope specificity of the L6 anti-idiotypic monoclonal antibodies was demonstrated in competition experiments in which either L6, the chimeric L6 heavy chain associated with the J558L murine lambda i light chain, the free chimeric L6 light chain, or an irrelevant human IgG1, was tested for their ability to compete for each anti-idiotypic antibody's binding to biotinylated chimeric L6 (FIG. 27). Each of the 14 Ab2 were shown to specifically recognize the cloned L6 V regions by virtue of their ability to bind the biotinylated chimeric L6 molecule. The binding was shown to be inhibitable by unlabelled chimeric L6, but not an irrelevant human IgG1. Eight Abs could be inhibited to an appreciable degree by the free chimeric L6 light chain (#1, #2, #4, #6, #7, #8, #9, and #15) but not by the chimeric heavy chain associated with mouse lambda 1, and therefore the eight Abs recognize an L6 light chain variable region. These eight are the Ab2 which are able to bind the L6 Fab bound to cells. Two of the Ab2 (#12 and #13) were inhibitable by the L6 chimeric heavy chain associated with the J558L light chain, but not by the free chimeric light chain, and they thus recognize an L6 heavy chain variable region-associated determinant. The remainder of the Ab2 (#3, #10, #11, and #14) were not inhibitable by either of the cloned V regions separately, and must therefore, be specific for a combinatorial determinant formed only by the assembly of the appropriate V regions. These results were also confirmed through direct binding studies.

9.2.5. Induction of AB3

Five of the 6 Ab2 which appeared to be binding-site-related were conjugated to KLH and used to immunize BALB/c and C3H/HeN mice, as described in Section 9.1.4. The mice were periodically bled and boosted, and their sera were analyzed.

A binding inhibition assay was first performed to determine whether the immunized mice appeared to make any Ab3 which could be identified by its ability to bind specifically to Ab2. Various dilutions of sera from the mice were mixed with Ab2 (1.0 μg/ml), the mixtures were applied to plates coated with Fab L6, and the binding of Ab2 to the Fab L6 was determined by an ELISA. Results were expressed as percent inhibition of the binding of Ab2 to Fab L6 in the presence of the given mouse serum. As shown in FIG. 28, the binding of Ab2 (1.0 μg/ml) to Fab L6 was inhibited over 90% at a 1:200 dilution of several of the immune mouse sera. The affinity purified antisera were found to inhibit binding of Ab2 in the same assay. This was seen for all the Ab2 tested and indicates that Ab3 were produced to the Ab2 paratope region. The induction of Ab3 anti-idiotypic to Ab2 was similar in BALB/c and C3H/HeN mice. 9.2.6. Ability of AB3 to Bind to the Antigen Defined by L6

If an Ab2 acts as an "internal image" of the L6 antigen, it should be able to invoke an Ab3 that binds specifically to the antigen defined by L6 (Ab1). To test the antigen specificity of the Ab3 generated in mice immunized with Ab2, various dilutions of the affinity purified immune mouse sera were tested for binding to cells from the L6-positive carcinoma lines H-3347; CEM cells to which L6 does not bind were used as the negative control. Sera from C3H/HeN mice (FIG. 29) which had been immunized with Ab2 #11 and #12 and sera from BALB/c mice (FIG. 30) immunized with Ab2 #14 bound to the carcinoma cells.

9.3. Discussion

We have generated monoclonal anti-idiotypic antibodies (Ab2) to a mouse mAb, L6, which binds to a carbohydrate antigen expressed on many human carcinomas. The Ab2 were first screened for binding to Fab L6 fragments, followed by screening for their ability to inhibit the binding of L6 to its target antigen on carcinoma cells. Out of a total of 24 Ab2 initially selected for binding to Fab L6, 14 Ab2 inhibited the binding of L6 to antigen-positive carcinoma cells. Six of the latter Ab2 were unable to bind to L6 Fab fragments previously bound to antigen on cells, suggesting that they identify a region of L6 which is associated with its antigen-binding site. When these 6 Ab2 were tested for binding to cloned L6 light and heavy chain variable regions, 4 Ab2 bound only to a combination of the appropriate V regions, while 2 Ab2 recognized the variable heavy chain region associated with an irrelevant variable light chain, and none could bind free chimetic L6 light chains. In contrast, all of 8 tested Ab2 which bound to Fab' L6 attached to cells could also bind to free chimetic L6 light chains.

An Ab1-like response in vivo was obtained only when using those Ab2 which did not bind to Fab L6 attached to cells and which bound to either a combinatorial or a heavy chain variable region-associated determinant. In contrast, of those Ab2 which bound to Fab L6 attached to carcinoma cells and to isolated chimetic L6 light chains, all failed to induce an Ab1-like Ab3 response in mice.

Ab2 #11, #12, and #14 behaved as "internal image" Ab2 in several different types of assays.

Two Ab2 (#11, #12) could induce an Ab1-like Ab3 response in mice. Sera from mice immunized with any of these Ab2 were able to bind with the same specificity as L6 to carcinoma cells. Since an Ab3 response was induced in allogeneic C3H/HeN mice, it was not allotype restricted, as would have been expected if the Ab2 had served as an immune regulator (Lee, V. K., et al., 1986, Biochim. Biophys. Acta 865:127–139). Rather, the Ab2 behaved as an "internal image" (Urbain, J., et al., 1982, Ann. Immunol. 133D179–189; Lee, V. K., et al., 1986, Blochim. Biophys. Acta 865:127–139) of the L6-defined antigen. It was also found that one Ab2 (#14) could induce an Ab1-like Ab3 response in the syngeneic system.

10. DEPOSIT OF MICROORGANISMS

The following hybridoma cell lines, producing the indicated monoclonal antibody, have been deposited with the American Type Culture Collection, 12301 Parklawn Drive, Rockville, Md., 20852 and have been assigned the listed accession number.

| Hybridoma | Monoclonal Antibody (Ab2) | Related Antigen | Date of Deposit | Accession Number |
|---|---|---|---|---|
| Cell line 2C1 | 2C1 | human melanoma-associated GD3 ganglioside antigen | 7-17-87 | Hb 9484 |
| Cell line #3 (24.89/1.3 cl.5) | #3 | human melanoma-associated p97 antigen | 8-13-87 | HB 9498 |
| Cell line #7 (24.6/28.2 cl.1) | #7 | human melanoma-associated p97 antigen | 8-13-87 | HB 9497 |
| 5/15-3-1 | #11 | human carcinoma-associated L6 antigen | 9-18-87 | HB 9544 |
| 10/24-1-5 | #12 | human carcinoma-associated L6 antigen | 4-1-88 | HB 9681 |
| 11/48-3-14 | #14 | human carcinoma-associated L6 antigen | 4-1-88 | HB 9680 |
| 4/1-6-1 | #1 | human carcinoma-associated L6 antigen | 9-18-87 | HB 9546 |
| 6/14-2-2 | #6 | human carcinoma-associated L6 antigen | 9-18-87 | HB 9545 |

The cell line, L6, was deposited at the ATCC on Dec. 6, 1984, and received accession number HB 8677.

The present invention is not to be limited in scope by the cell line deposited since the deposited embodiment is intended as a single illustration of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

What is claimed is:

1. A monoclonal anti-idiotypic antibody, the antigen-combining site of which specifically binds to the idiotype of monoclonal antibody L6 as deposited with the ATCC and assigned accession number HB8677.

2. The monoclonal anti-idiotypic antibody of claim 1 wherein the anti-idiotypic antibody is monoclonal antibody #11, as deposited with the ATCC and assigned accession number HB 9544.

3. The monoclonal anti-idiotypic antibody of claim 1 wherein the anti-idiotypic antibody is monoclonal antibody #12, as deposited with the ATCC and assigned accession number HB 9681.

4. The monoclonal anti-idiotypic antibody of claim 1 wherein the anti-idiotypic antibody is monoclonal antibody #14, as deposited with the ATCC and assigned accession number HB 9680.

5. The Fv, Fab, Fab' or F(ab')$_2$ fragment of the monoclonal anti-idiotypic antibody of claim 1, 2, 3 or 4.

* * * * *